US008076287B2

(12) United States Patent
Zazopoulos et al.

(10) Patent No.: US 8,076,287 B2
(45) Date of Patent: Dec. 13, 2011

(54) CYCLIC HEXADEPSIPEPTIDES, PROCESSES FOR THEIR PRODUCTION AND THEIR USE AS PHARMACEUTICALS

(75) Inventors: Emmanuel Zazopoulos, Montreal (CA); James B. McAlpine, Montreal (CA); Arjun H. Banskota, Halifax (CA); Mahmood Piraee, Cambridge (GB)

(73) Assignee: Thallion Pharmaceuticals Inc., Montreal, Quebec (CA)

( * ) Notice: Subject to any disclaimer, the term of this patent is extended or adjusted under 35 U.S.C. 154(b) by 566 days.

(21) Appl. No.: 12/294,213

(22) PCT Filed: Mar. 28, 2007

(86) PCT No.: PCT/US2007/007620
§ 371 (c)(1),
(2), (4) Date: Feb. 6, 2009

(87) PCT Pub. No.: WO2007/126849
PCT Pub. Date: Nov. 8, 2007

(65) Prior Publication Data
US 2009/0215789 A1    Aug. 27, 2009

Related U.S. Application Data

(60) Provisional application No. 60/786,691, filed on Mar. 29, 2006.

(51) Int. Cl.
*A61K 38/12*    (2006.01)
(52) U.S. Cl. ...... 514/2.4; 514/19.3; 514/19.4; 514/19.5; 514/21.1
(58) Field of Classification Search .................. None
See application file for complete search history.

(56) References Cited

FOREIGN PATENT DOCUMENTS
EP        0 995 758 A1    4/2000

OTHER PUBLICATIONS

Tajiri et al, Amylase Inhibitors Produced by Streptomyces-SP No. 280, Agricultural and Biological Chemistry, vol. 47, No. 4, 1983, pp. 671-680.

*Primary Examiner* — Christina Bradley
(74) *Attorney, Agent, or Firm* — Roylance, Abrams, Berdo & Goodman, L.L.P.

(57) ABSTRACT

The present invention provides cyclic hexadepsipeptides and their pharmaceutically acceptable salts, solvates and prodrugs, and methods for obtaining the compounds, by fermentation, optionally followed by post-biosynthesis chemical modification. The present invention further provides uses of cyclic hexadepsipeptides, and their pharmaceutically acceptable salts, solvates and prodrugs as pharmaceuticals, in particular to their use as antibacterial, antifungal or antineoplastic agents, and to pharmaceutical compositions comprising a cyclic hexadepsipeptide, or a pharmaceutically acceptable salt, solvate or prodrug thereof, together with a carrier.

10 Claims, 3 Drawing Sheets

Figure 1

| RT | Resp | Ar/Ht | RFact | ECL | Peak Name | % | Comment 1 | Comment 2 |
|---|---|---|---|---|---|---|---|---|
| 1.817 | 4.158E+8 | 0.032 | --- | 6.987 | SOLVENT PEAK | --- | < min rt | |
| 2.109 | 12208 | 0.024 | --- | 7.596 | | --- | < min rt | |
| 2.444 | 4113 | 0.027 | --- | 8.296 | | --- | < min rt | |
| 3.163 | 451 | 0.023 | --- | 9.798 | | --- | | |
| 4.803 | 968 | 0.040 | 1.078 | 11.999 | 12:0 | 0.31 | ECL deviates -0.001 | Ref 0.003 |
| 5.483 | 630 | 0.034 | 1.049 | 12.614 | 13:0 ISO | 0.20 | ECL deviates 0.002 | Ref 0.005 |
| 5.579 | 814 | 0.034 | 1.045 | 12.701 | 13:0 ANTEISO | 0.26 | ECL deviates 0.000 | Ref 0.003 |
| 6.727 | 10443 | 0.040 | 1.008 | 13.617 | 14:0 ISO | 3.16 | ECL deviates -0.001 | Ref 0.000 |
| 6.987 | 779 | 0.054 | --- | 13.813 | | --- | | |
| 7.232 | 5692 | 0.041 | 0.994 | 13.998 | 14:0 | 1.70 | ECL deviates -0.002 | Ref 0.000 |
| 8.166 | 27006 | 0.043 | 0.973 | 14.621 | 15:0 ISO | 7.89 | ECL deviates 0.000 | Ref 0.001 |
| 8.302 | 46066 | 0.043 | 0.970 | 14.712 | 15:0 ANTEISO | 13.41 | ECL deviates 0.001 | Ref 0.002 |
| 8.734 | 2669 | 0.044 | 0.962 | 15.000 | 15:0 | 0.77 | ECL deviates 0.000 | Ref 0.001 |
| 9.479 | 6191 | 0.047 | 0.949 | 15.457 | 16:1 ISO H | 1.76 | ECL deviates -0.004 | |
| 9.755 | 52191 | 0.045 | 0.945 | 15.626 | 16:0 ISO | 14.80 | ECL deviates 0.000 | Ref 0.000 |
| 10.064 | 37990 | 0.049 | 0.940 | 15.816 | 16:1 CIS 9 | 10.72 | ECL deviates -0.001 | |
| 10.364 | 83190 | 0.048 | 0.936 | 15.999 | 16:0 | 23.37 | ECL deviates -0.001 | Ref -0.001 |
| 11.073 | 5195 | 0.047 | 0.927 | 16.416 | 16:0 9? Methyl | 1.45 | ECL deviates 0.000 | |
| 11.180 | 1038 | 0.043 | 0.926 | 16.479 | Sum in feature 5 | 0.29 | ECL deviates 0.003 | 17:1 ISO I/ANTEI B |
| 11.255 | 3681 | 0.053 | 0.925 | 16.523 | 17:1 ANTEISO C | 1.02 | ECL deviates -0.002 | |
| 11.436 | 8299 | 0.048 | 0.923 | 16.630 | 17:0 ISO | 2.30 | ECL deviates 0.001 | Ref 0.000 |
| 11.595 | 30226 | 0.048 | 0.921 | 16.723 | 17:0 ANTEISO | 8.36 | ECL deviates 0.001 | Ref 0.000 |
| 11.711 | 3430 | 0.049 | 0.920 | 16.791 | 17:1 CIS 9 | 0.95 | ECL deviates -0.001 | |
| 12.066 | 2193 | 0.046 | 0.916 | 17.000 | 17:0 | 0.60 | ECL deviates 0.000 | Ref -0.001 |
| 12.775 | 992 | 0.045 | 0.910 | 17.408 | 17:0 10Methyl | 0.27 | ECL deviates -0.002 | |
| 12.877 | 1276 | 0.044 | 0.909 | 17.466 | 18:1 ISO H | 0.35 | ECL deviates 0.006 | |
| 13.161 | 1154 | 0.051 | 0.907 | 17.630 | 18:0 ISO | 0.31 | ECL deviates -0.002 | Ref -0.003 |
| 13.399 | 3916 | 0.048 | 0.905 | 17.767 | 18:1 CIS 9 | 1.06 | ECL deviates -0.002 | |
| 13.492 | 11506 | 0.052 | 0.905 | 17.820 | Sum in feature 7 | 3.12 | ECL deviates -0.002 | 18:1 CIS 11/t 9/t 6 |
| 13.806 | 5818 | 0.051 | 0.903 | 18.001 | 18:0 | 1.58 | ECL deviates 0.001 | Ref -0.001 |
| 19.279 | 466 | 0.089 | --- | 21.181 | | --- | > max rt | |
| 19.445 | 572 | 0.057 | --- | 21.278 | | --- | > max rt | |
| 19.481 | 129 | 0.026 | --- | 21.299 | | --- | > max rt | |
| 19.676 | 516 | 0.096 | --- | 21.413 | | --- | > max rt | |
| 19.744 | 501 | 0.081 | --- | 21.453 | | --- | > max rt | |
| 19.848 | 99 | 0.018 | --- | 21.513 | | --- | > max rt | |
| --- | 1038 | --- | --- | --- | Summed feature 5 | 0.29 | 17:1 ISO I/ANTEI B | 17:1 ANTEISO B/i I |
| --- | 11506 | --- | --- | --- | Summed feature 7 | 3.12 | 18:1 CIS 11/t 9/t 6 | 18:1 TRANS 9/t6/c11 |
| --- | --- | --- | --- | --- | | --- | 18:1 TRANS 6/t9/c11 | |

ECL Deviation: 0.002  Reference ECL Shift: 0.002  Number Reference peaks: 15
Total Response: 353804  Total Named: 352574
Percent Named: 99.65%  Total Amount: 333197

Matches:
Library           Sim Index      Entry Name
ACTIN1 3.80           0.001              *Streptomyces halstedii scabies*
                      0.000              *Streptoverticillium cinnamoneum*
                      0.000              *Streptomyces violaceusniger violaceusniger*

FIGURE 2

| Alignment: | 500 C18571 280 con |
|---|---|
| 5.00 % 500 | *Streptomyces cremeus* |
| 5.20 % 500 | *Streptomyces polychromogenes* |
| 5.20 % 500 | Streptomyces omiyaensis |
| 5.40 % 500 | Streptomyces netropsis |
| 5.40 % 500 | Streptomyces candidus |
| 5.40 % 500 | Streptomyces lavendulae lavendulae |
| 5.40 % 500 | Streptomyces narbonensis |
| 5.60 % 500 | Streptomyces griseinus |
| 5.60 % 500 | Streptomyces olivoviridis |
| 5.80 % 500 | Streptomyces cavourensis |

CYCLIC HEXADEPSIPEPTIDES, PROCESSES FOR THEIR PRODUCTION AND THEIR USE AS PHARMACEUTICALS

This application is a U.S. national stage application under 35 U.S.C. §371 of PCT/US2007/007620, filed on Mar. 28, 2007, which claims priority to U.S. Provisional patent application number 60/786,691, filed Mar. 29, 2006 the disclosure of which is incorporated herein in its entirety.

FIELD OF THE INVENTION

This invention relates to cyclic hexadepsipeptides and their pharmaceutically acceptable salts, solvates and prodrugs, and to methods for obtaining the compounds, by fermentation optionally followed by post-biosynthesis chemical modification. The present invention further relates to the use of cyclic hexadepsipeptides, and their pharmaceutically acceptable salts, solvates and prodrugs as pharmaceuticals, in particular to their use as antibacterial, antifungal or antineoplastic agents, and to pharmaceutical compositions comprising a cyclic hexadepsipeptide, or a pharmaceutically acceptable salt, solvate or prodrug thereof, together with a carrier.

BACKGROUND OF THE INVENTION

The euactinomycetes are a subset of a large and complex group of Gram-positive bacteria known as actinomycetes. Over the past few decades these organisms, which are abundant in soil, have generated significant commercial and scientific interest as a result of the large number of therapeutically useful compounds, particularly antibiotics, produced as secondary metabolites. The intensive search for strains able to produce new antibiotics has led to the identification of hundreds of new species.

Many of the euactinomycetes, particularly *Streptomyces* and the closely related *Saccharopolyspora* genera, have been extensively studied. Both of these genera produce a notable diversity of biologically active metabolites. Because of the commercial significance of these compounds, much is known about the genetics and physiology of these organisms. A number of cyclic hexadepsipeptides have been isolated from *Streptomyces* species. For example, aurantimycins (Gräfe, U. et al. (1995), *J. of Antibiotics*, Vol. 48, no. 2, 119-125); azinothricin (Maehr, H. et al. (1986), *J. of Antibiotics*, Vol 39, no 1, 17-25); GE3 and GE3B (Sakai, Y. et al. (1997), *J. of Antibiotics*, vol 50, no 8, 659-664); and polyoxypeptins A and B (Umezawa K. et al. (1998), *Tet. Lett.*, Vol 39, 1389-92; Umezawa K. et al. (1999), *J. Org. Chem.*, Vol 64, no 9, 3034-8; and Umezawa K. et al. (1998), *Adv. Enzyme Regul.*, vol 39, 145-156; and WO 98/56809, Takeuchi et al.).

Although many biologically active compounds have been identified from bacteria, there remains the need to obtain novel compounds with enhanced properties. Thus, there exists a considerable need to obtain pharmaceutically active compounds in a cost-effective manner and with high yield. The present invention solves these problems by providing new therapeutic compounds and methods to generate these novel compounds by fermentation and optional post-biosynthetic chemical modifications.

SUMMARY OF THE INVENTION

In one aspect, invention provides a cyclic hexadepsipeptide represented by a compound of Formula I:

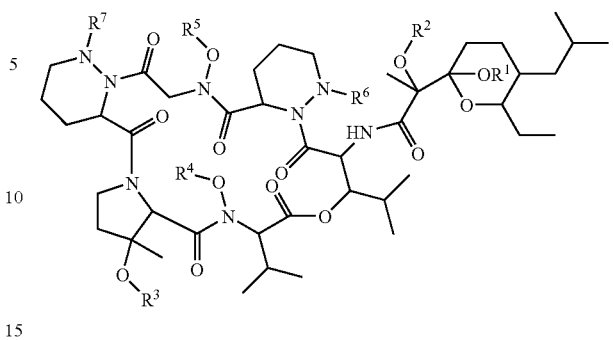

Formula I wherein, $R^1$, $R^2$ and $R^3$ are each independently selected from H, $R^8$ and $C(O)R^9$;

$R^4$ and $R^5$ are each independently selected from H, $C_{1-6}$alkyl, $C_{1-6}$alkenyl, and $C_{1-6}$alkynyl;

$R^6$ and $R^7$ are each independently selected from H, $R^{10}$ and $C(O)R^{11}$;

$R^8$ and $R^{10}$ are each independently selected form $C_{1-6}$alkyl, $C_{1-6}$alkenyl, $C_{1-6}$alkynyl, $C_{3-10}$cycloalkyl, and $C_{3-10}$heterocycloalkyl;

$R^9$ and $R^{11}$ are each independently selected from H, $C_{1-6}$alkyl, $C_{1-6}$alkenyl, $C_{1-6}$alkynyl, $C_{3-10}$cycloalkyl, $C_{3-10}$heterocycloalkyl, $C_{6-10}$aryl, and $C_{5-10}$heteroaryl, or $C(O)R^9$ and $C(O)R^{11}$ may each independently be a C-coupled amino acid;

wherein, when any of $R^1$, $R^2$, $R^3$, $R^4$, $R^5$, $R^6$, $R^7$, $R^8$, $R^9$, $R^{10}$ and $R^{11}$ comprises an alkyl, alkenyl, alkynyl, aryl, heteroaryl, cycloalkyl, or heterocycloalkyl group, then the alkyl, alkenyl, alkynyl, aryl, heteroaryl, cycloalkyl, or heterocycloalkyl group is optionally substituted with substituents selected from acyl, amino, acylamino, acyloxy, carboalkoxy, carboxy, carboxyamido, cyano, halo, hydroxyl, nitro, thio, $C_{1-6}$alkyl, $C_{2-7}$alkenyl, $C_{2-7}$alkynyl, $C_{3-10}$cycloalkyl, $C_{3-10}$heterocycloalkyl, $C_{6-10}$aryl, $C_{5-10}$heteroaryl, alkoxy, aryloxy, sulfinyl, sulfonyl, oxo, guanidino and formyl;

or an ether, an ester, an N-alkylated or N-acylated derivative, or a pharmaceutically acceptable salt, solvate or prodrug thereof.

In one embodiment, $R^1$ is H, and all other groups are as previously disclosed. In another embodiment, $R^2$ is H, and all other groups are as previously disclosed. In another embodiment, $R^1$ to $R^5$ are all H, and all other groups are as previously disclosed. In another embodiment, $R^4$ and $R^5$ are both H, and all other groups are as previously disclosed. In another embodiment, $R^1$ to $R^3$ are all H, and all other groups are as previously disclosed. In another embodiment, $R^1$ to $R^7$ are all H, and all other groups are as previously disclosed. In another embodiment, $R^6$ and $R^7$ are both H, and all other groups are as previously disclosed. In another embodiment, $R^1$ to $R^3$ are all $C(O)CH_3$, and all other groups are as previously disclosed. In another embodiment, $R^6$ and $R^7$ are both $C(O)CH_3$, and all other groups are as previously disclosed. In another embodiment, $R^1$ to $R^3$ are all $CH_3$, and all other groups are as previously disclosed. In another embodiment, $R^6$ and $R^7$ are both $CH_3$, and all other groups are as previously disclosed. The invention encompasses all esters, ethers, N-alkylated or N-acylated derivatives, and pharmaceutically acceptable salts, solvates and prodrugs of the foregoing compounds.

In another embodiment, the cyclic hexadepsipeptide is represented by any one of Compounds 1 to 30:
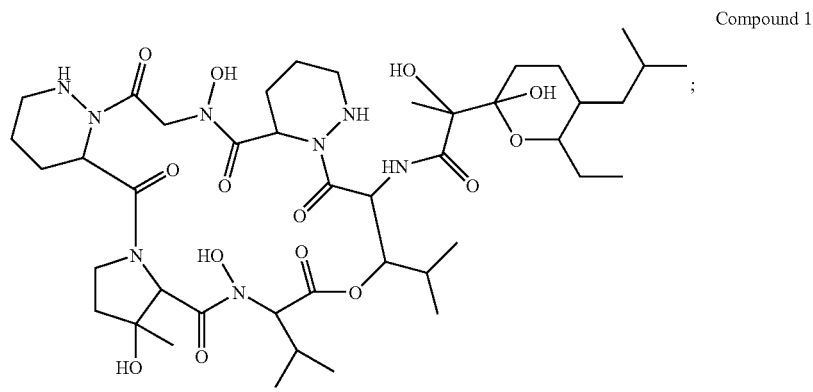
Compound 1
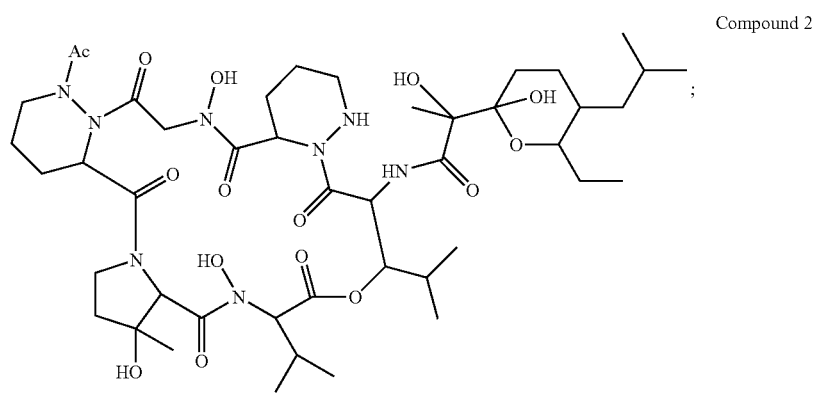
Compound 2
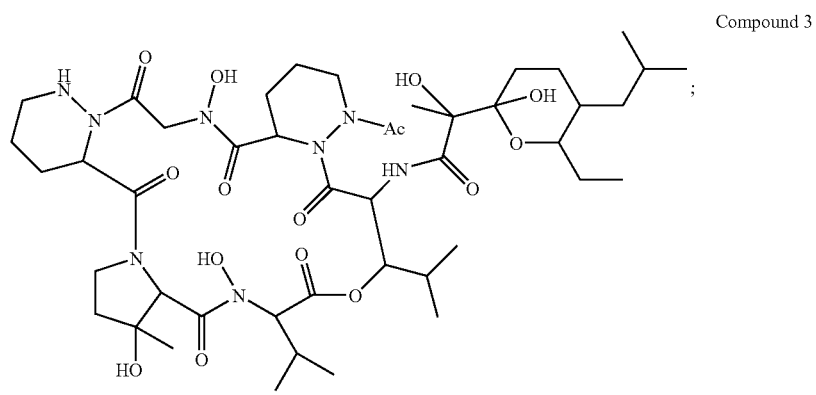
Compound 3
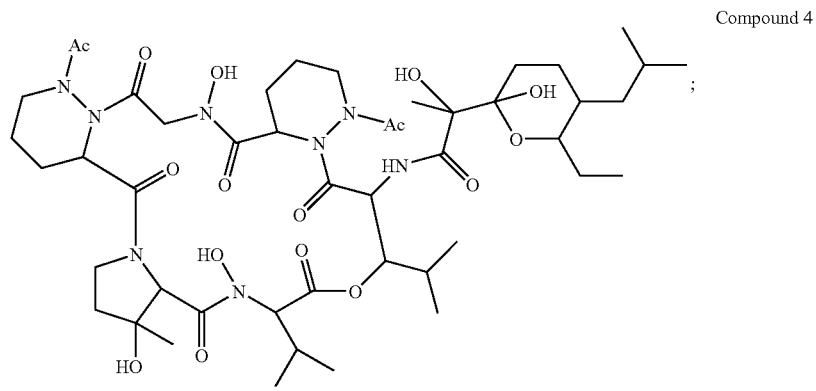
Compound 4

Compound 5
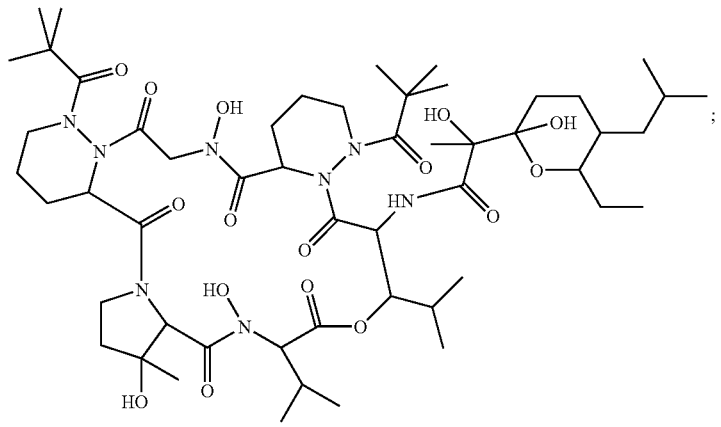
Compound 6
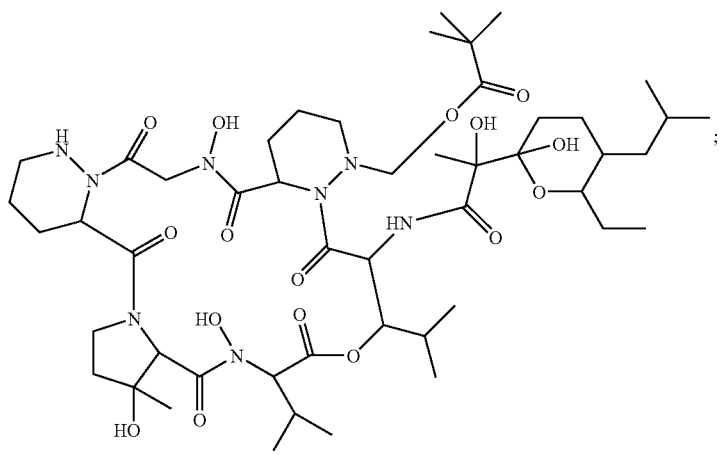
Compound 7
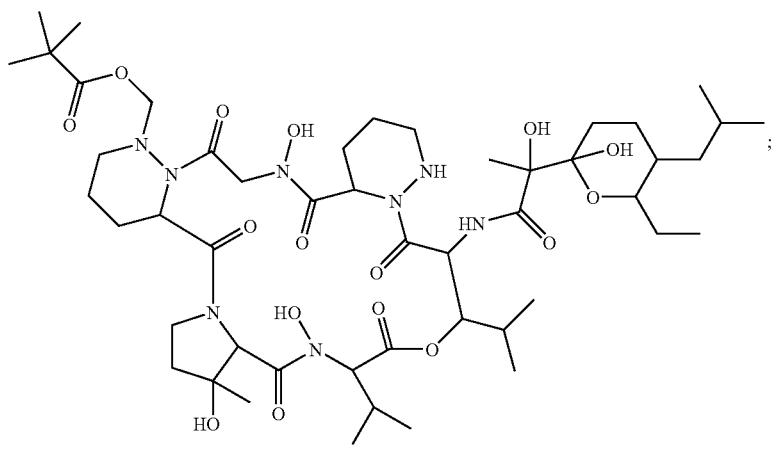

Compound 8
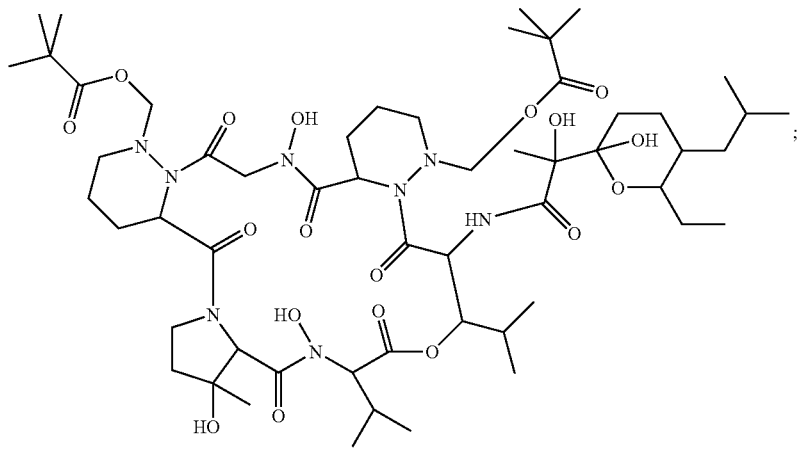
Compound 9
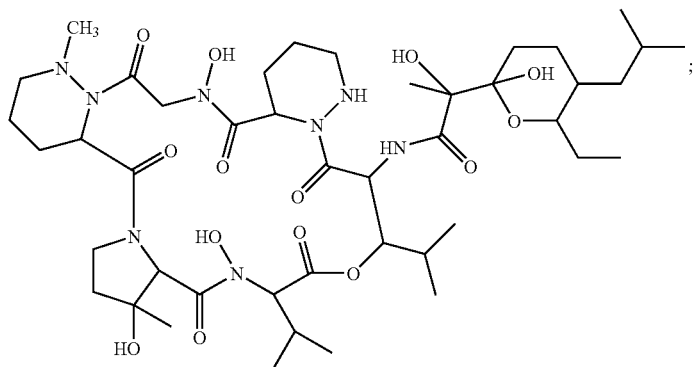
Compound 10
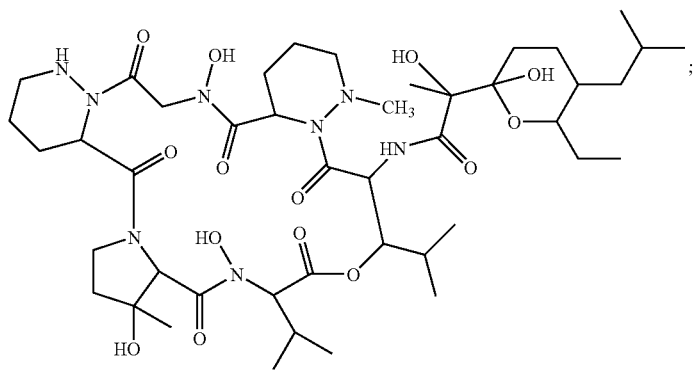
Compound 11
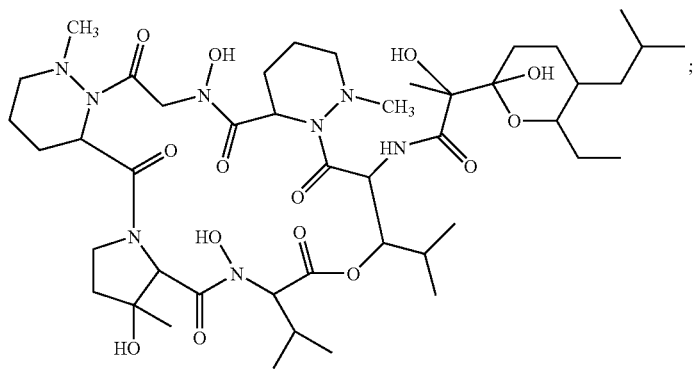

-continued
Compound 12
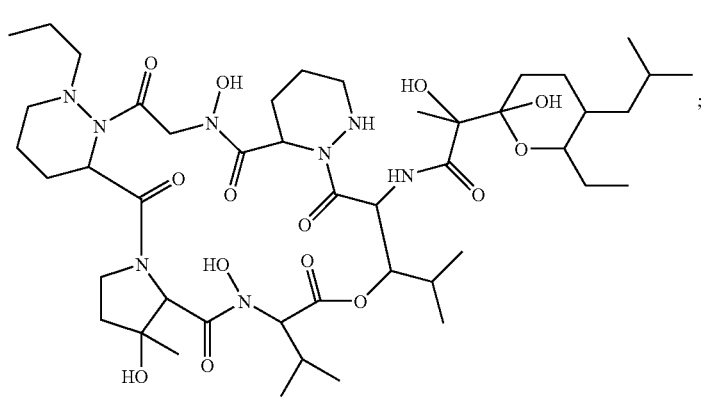
Compound 13
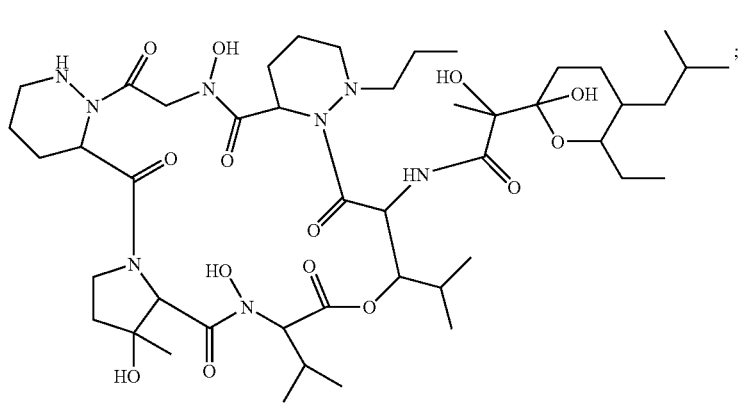
Compound 14
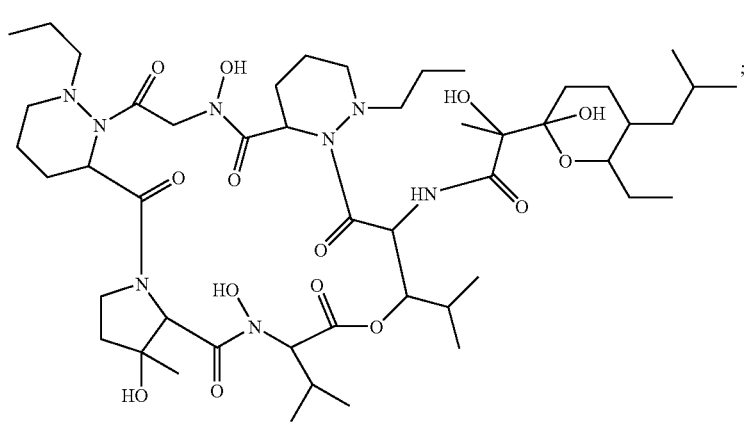
Compound 15
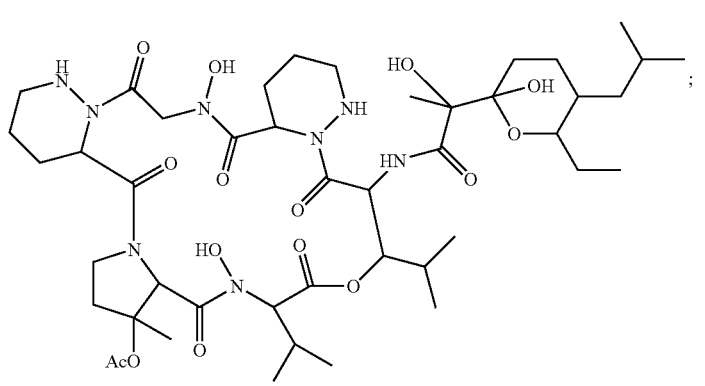

-continued
Compound 16
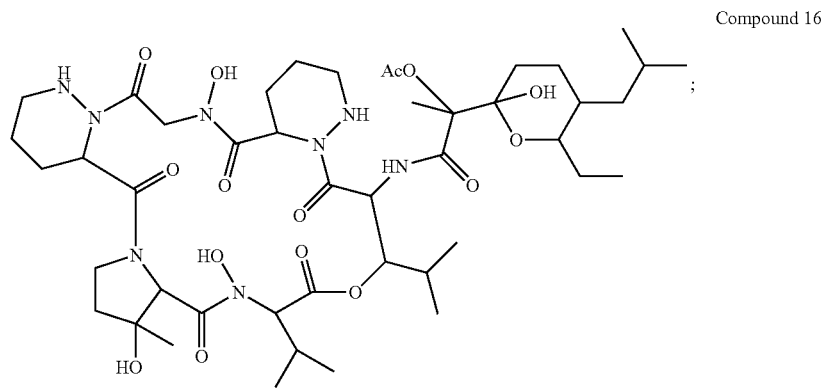
Compound 17
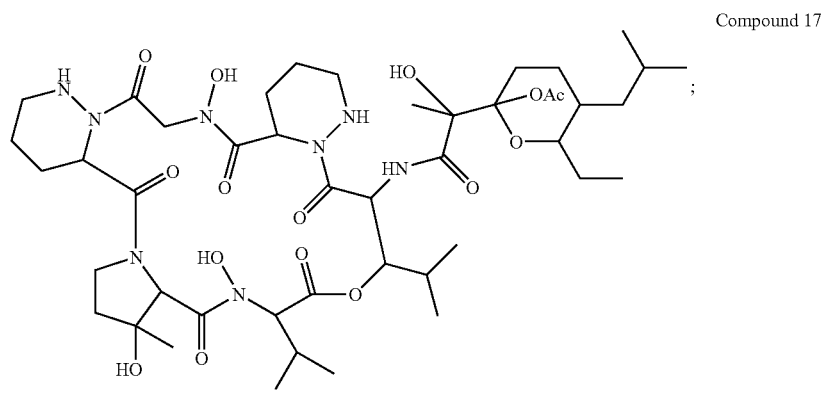
Compound 18
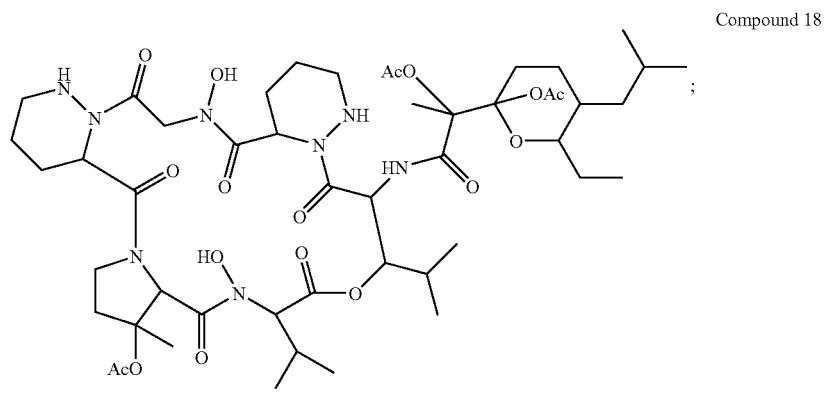
Compound 19
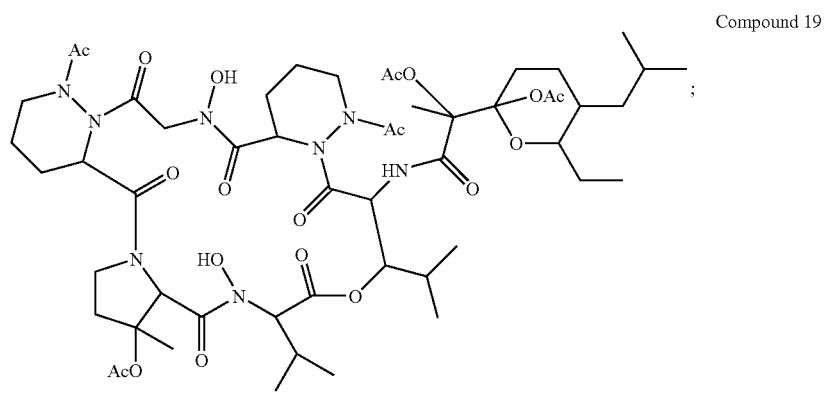

-continued
Compound 20
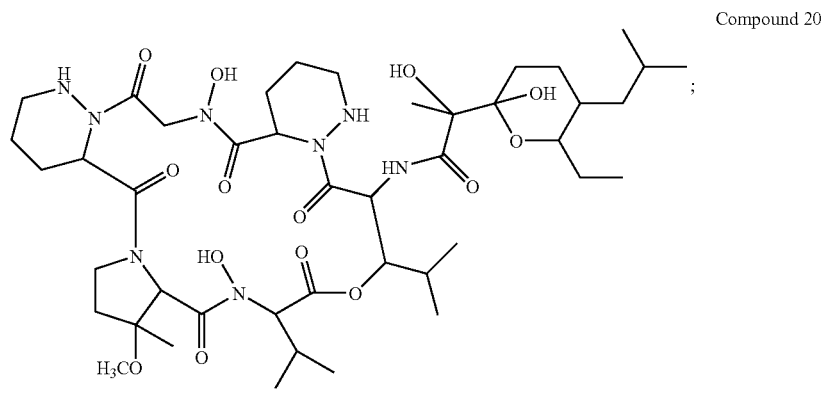
Compound 21
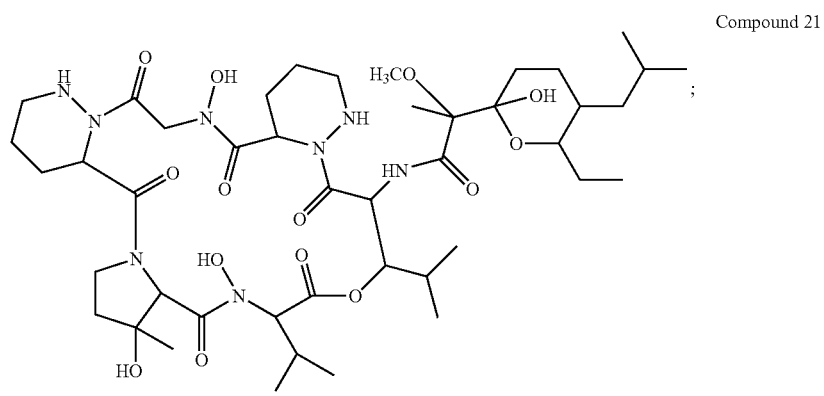
Compound 22
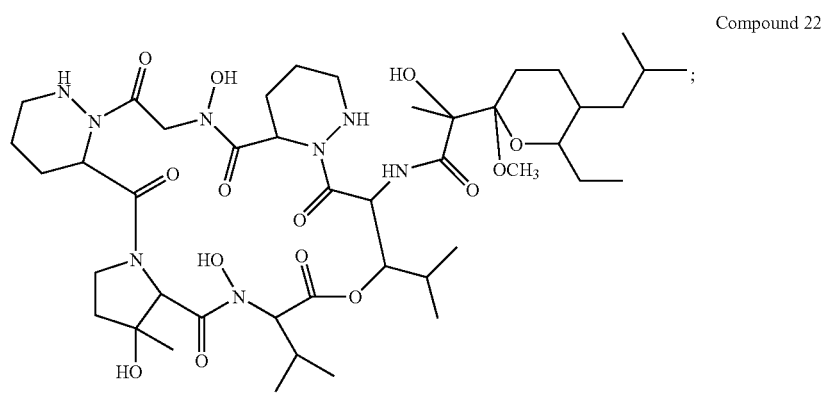
Compound 23
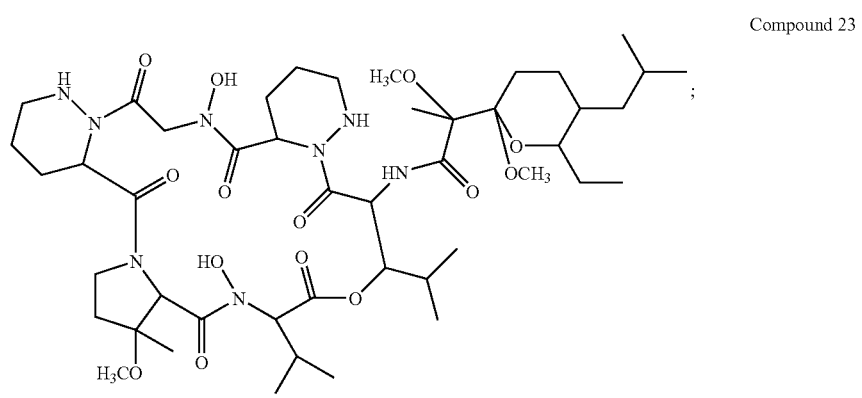

Compound 24
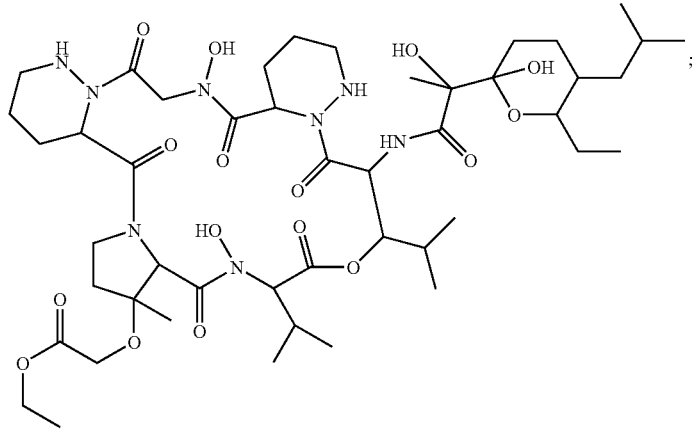
Compound 25
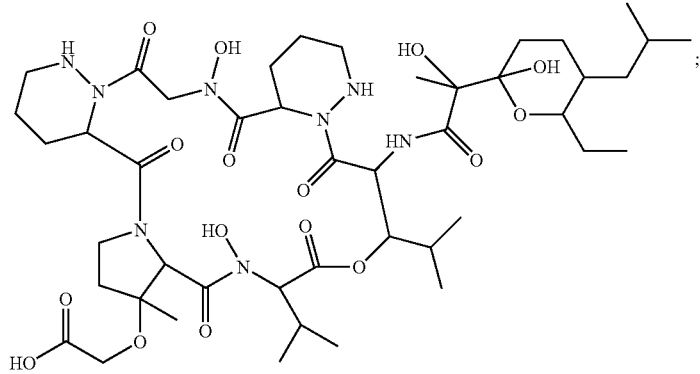
Compound 26
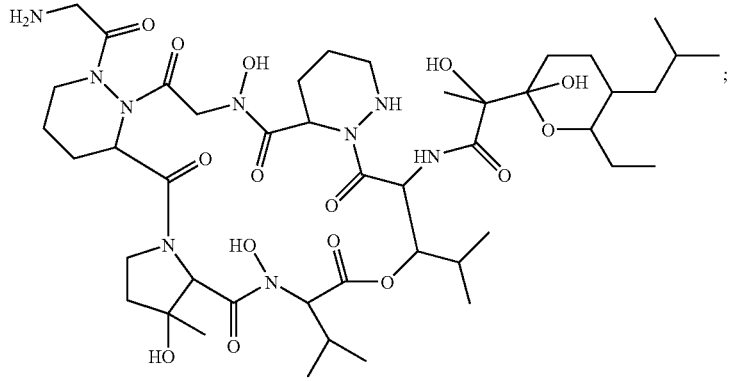
Compound 27
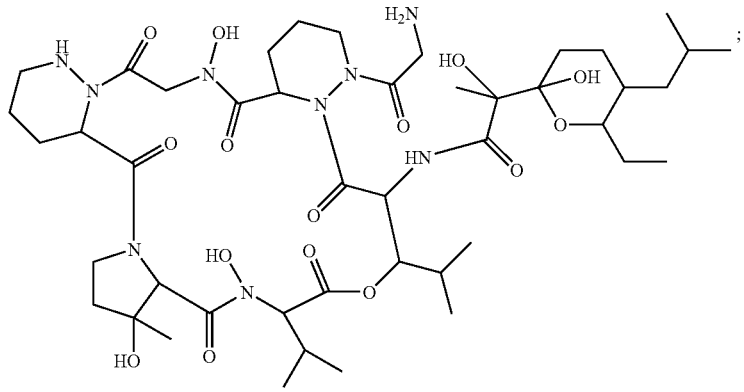

Compound 28

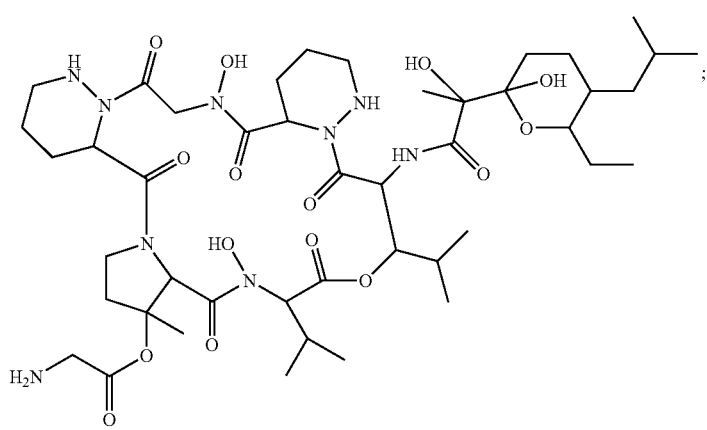

Compound 29

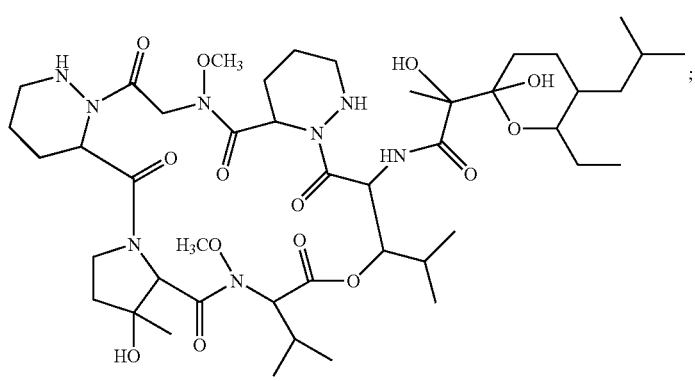

Compound 30

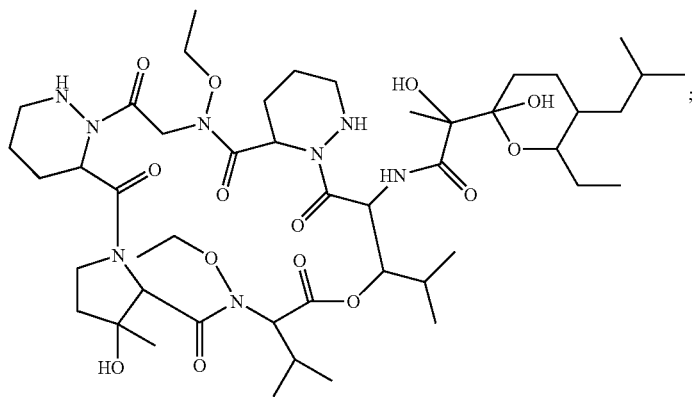

wherein "Ac" refers to acetyl. The invention further provides ethers, esters, N-alkylated or N-acylated derivatives, or pharmaceutically acceptable salts, solvates or prodrugs of any one of Compounds 1 to 30. Certain embodiments may exclude one or more of the compounds of the invention.

The invention further encompasses a cyclic hexadepsipeptide obtained by a method comprising the steps of: (a) cultivating a *Streptomyces* sp. strain, wherein the cultivation is performed under aerobic conditions in a nutrient medium comprising at least one source of carbon atoms and at least one source of nitrogen atoms; and b) isolating a cyclic hexadepsipeptide from the bacteria cultivated in step (a); or ma method comprising steps (a) and (b), and step (c) chemically modifying the compound isolated in (b). In one embodiment, the strain is *Streptomyces* sp. strain Eco180. In one embodiment the cyclic hexadepsipeptide isolated in (b) is Compound 1. In another embodiment, the cyclic hexadepsipeptide produced in step (c) is a compound of Formula I. In a further embodiment, the cyclic hexadepsipeptide produced in step (c) is any one of Compounds 2 to 30.

The invention further encompasses a process or method for making a cyclic hexadepsipeptide compound, comprising cultivation of a *Streptomyces* sp. strain in a nutrient medium comprising at least one source of carbon atoms and at least one source of nitrogen atoms, isolation and purification of the compound. In one embodiment, the *Streptomyces* sp. is *Streptomyces* sp. Eco180, or a cyclic hexadepsipeptide-producing mutant or variant thereof. In one embodiment, the cultivation occurs under aerobic conditions. In another embodiment, the carbon atom and nitrogen atom sources are chosen from the components shown in Table 1. In another embodiment, the cultivation is carried out at a temperature ranging from 18° C. to 40° C. In a further embodiment, the temperature range is 25° C. to 32° C. In another embodiment, the cultivation is carried out at a pH ranging from 6 to 9. In a yet another embodiment, the process further comprises the step of chemically modifying the isolated compound. In a subclass of this embodiment, the chemical modification step comprises at least one N-alkylation, N-acylation, O-alkylation, or O-acylation step.

The invention further provides *Streptomyces* sp. Eco180, having IDAC accession number 220905-01, or a cyclic hexadepsipeptide-producing mutant or variant thereof.

The invention further relates to a pharmaceutical composition comprising a therapeutically effective amount of a compound of Formula I, or a pharmaceutically acceptable salt or prodrug thereof, together with a pharmaceutically acceptable carrier. The invention further encompasses the use of a compound of Formula I, or a pharmaceutically acceptable salt or prodrug thereof as an antineoplastic agent for the treatment of a proliferative disorder, pre-cancerous or cancerous condition in a mammal. The invention further encompasses the use of a compound of Formula I, or a pharmaceutically acceptable salt or prodrug thereof in the preparation of a medicament for the treatment of a neoplastic, pre-cancerous or cancerous condition in a mammal. In one embodiment, the compound is any one of Compounds 1 to 30, or a pharmaceutically acceptable salt, solvate or prodrug thereof. In another embodiment, the compound is Compound 1, or a pharmaceutically acceptable salt, solvate or prodrug thereof.

The invention further encompasses a commercial package comprising a compound of Formula I, or a pharmaceutically acceptable salt or prodrug thereof, together with instructions for use in the treatment of a neoplasm or a pre-cancerous or cancerous condition. In one embodiment, the compound is any one of Compounds 1 to 30, or a pharmaceutically acceptable salt, solvate or prodrug thereof. In another embodiment, the compound is Compound 1, or a pharmaceutically acceptable salt, solvate or prodrug thereof.

The invention further encompasses a method of inhibiting the growth of a neoplastic cell, the method comprising contacting the cancer cell with a compound of Formula I, or a pharmaceutically acceptable salt or prodrug thereof, such that growth of the neoplastic cell is inhibited. In one embodiment, the compound is any one of Compounds 1 to 30, or a pharmaceutically acceptable salt, solvate or prodrug thereof. In another embodiment, the compound is Compound 1, or a pharmaceutically acceptable salt, solvate or prodrug thereof.

The invention further encompasses a method of inhibiting the growth of a neoplastic cell, or a method of treating a neoplastic, pre-cancerous or cancerous condition in a mammal, the method comprising administering a compound of Formula I, or a pharmaceutically acceptable salt or prodrug thereof, to a mammal comprising a neoplastic cell, such that growth of the neoplastic cell is inhibited in the mammal. In one embodiment, the cancer cell, neoplastic, pre-cancerous or cancerous condition, in the above-mentioned uses and methods, is selected from leukemia, melanoma, breast cancer, lung cancer, pancreatic cancer, ovarian cancer, renal cancer, colon or colorectal cancer, prostate cancer, and CNS cancer. In another embodiment, the cancer cell, and pre-cancerous or cancerous condition, in the above-mentioned methods and uses, is selected from leukemia, breast cancer, prostate cancer, and CNS cancer.

The invention also provides methods of inhibiting bacterial cell growth, which comprise contacting said bacterial cell with a compound of Formula I, or a pharmaceutically acceptable salt or prodrug thereof. The invention further encompasses methods for treating a bacterial infection in a subject, comprising administering to the subject suffering from said bacterial infection, a therapeutically effective amount of a compound of Formula I, or a pharmaceutically acceptable salt or prodrug thereof. The invention further provides use of a compound of Formula I as an antibacterial agent, or in the manufacture of a medicament for the treatment of bacterial infections. In one embodiment, the compound is selected from Compounds 1 to 30, or a pharmaceutically acceptable salt or prodrug thereof. In another embodiment, the compound is Compound 1, or a pharmaceutically acceptable salt or prodrug thereof.

In one embodiment, the bacterial infection or organism involved in any of the above-mentioned uses and methods, is selected from: *Streptococcus pneumoniae, Streptococcus pyogenes, Enterococcus faecalis, Enterococcus faecium, Klebsiella pneumoniae, Enterobacter* spp., *Proteus* spp., *Pseudomonas aeruginosa, Serratia marcescens, Staphylococcus aureus, Coagulase negative Staphylococcus, Haemophilus infuenzae, Bacillus anthracis, Mycoplasma pneumoniae,* and *Staphylococcus epidermidis.*

The invention further provides the use of a compound of Formula I, or a pharmaceutically acceptable salt or prodrug thereof, as an anti-fungal agent, and for the treatment of fungal infections. The invention also provides a method of inhibiting fungal growth, and treating a fungal infection, comprising the step of contacting the fungal growth with a compound of Formula I, or a pharmaceutically acceptable salt or prodrug thereof. In one embodiment, the compound is any one of Compounds 1 to 30, or a pharmaceutically acceptable salt or prodrug thereof. In another embodiment, the compound is Compound 1, or a pharmaceutically acceptable salt or prodrug thereof.

BRIEF DESCRIPTION OF THE FIGURES

FIG. 1: shows results of the fatty acid analysis of *Streptomyces* sp. strain Eco180 (Accession No. IDAC 220905-01). Analysis was conducted using gas chromatography on fatty acid methyl esters (FAME).

FIG. 2: illustrates the 16S ribosomal RNA analysis *Streptomyces* sp. strain Eco180 (Accession No. IDAC 220905-01). Alignment of 16S ribosomal RNA sequences demonstrates the phylogenetic relatedness of *Streptomyces* sp. strain Eco180 (indicated as C18571 280 con) to other *Streptomyces* strains.

DETAILED DESCRIPTION OF THE INVENTION

Figure 3:
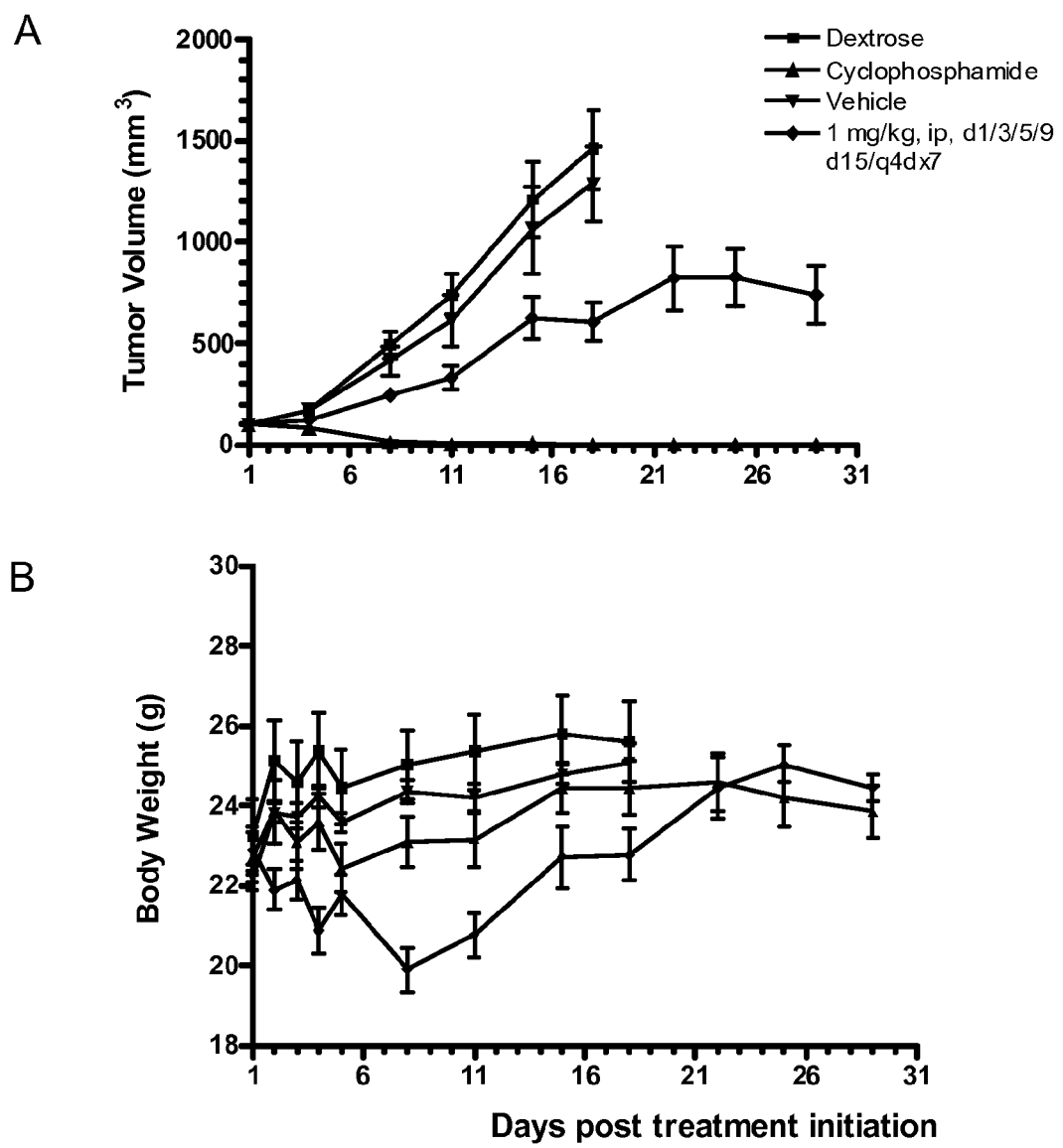
FIG. 3: (a) shows inhibition of tumor growth resulting from bolus i.p. administration of 1 mg/kg of Compound 1 to human MX-1 breast carcinoma xenograft in mice compared with negative control (dextrose and Vehicle) and positive control (cyclophosphamide); (b) shows the mean body weight of each of Groups 1 to 4 during the treatment.

The present invention relates to novel cyclic hexadepsipeptides, herein referred as the compounds of Formula I. The invention further relates to pharmaceutically acceptable salts, solvates and prodrugs of cyclic hexadepsipeptide compounds.

The invention also relates to methods for producing cyclic hexadepsipeptides, by fermentation and isolation and by optional chemical modification of the cyclic hexadepsipeptide obtained from fermentation and isolation. In a subclass of this embodiment, the compound produced is a compound of Formula I, or a compound selected from Compounds 1 to 30.

The present invention also relates to pharmaceutical compositions comprising a compound selected from the compounds of Formula I, Compounds 1 to 30, and their pharmaceutically acceptable salts, solvates and prodrugs. The compounds are useful as pharmaceuticals, in particular for use as inhibitors of neoplastic cell growth and as antibacterial or antifungal agents.

The following detailed description discloses how to make and use the cyclic hexadepsipeptides and compositions containing these compounds to inhibit tumor growth, or a bacterial or fungal infection.

I. Definitions

All technical and scientific terms used herein have the same meaning as commonly understood by one of ordinary skill in the art to which this invention belongs. For convenience, the meaning of certain terms and phrases used in the specification, examples, and appended claims, are provided below.

As used herein, the terms "compound(s) of the invention", "cyclic hexadepsipeptide(s)", "cyclic hexadepsipeptide compound(s)", and equivalent expressions refer to a class of cyclic compounds composed of a total of six amino acids and hydroxy acids in peptide and ester bonds respectively, namely the compounds of Formula I, and pharmaceutically acceptable salts, solvates and prodrugs thereof. The term includes a compound of Formula I, a compound selected from Compounds 1 to 30, or a pharmaceutically acceptable salt, solvate or prodrug of any of the above compounds. As used herein, the term "cyclic hexadepsipeptides" includes compounds of this class that can be used as intermediates in chemical syntheses and variants containing different isotopes than the most abundant isotope of an atom (e.g, D replacing H, $^{13}C$ replacing $^{12}C$, etc). The compounds of the invention are also sometimes referred to as "active ingredients".

As used herein, the term "chemical modification" refers to one or more steps of modifying a cyclic hexadepsipeptide compound, referred to as "starting material", by chemical synthesis. Preferred compound used as starting materials in a chemical modification process is Compound 1. Examples of chemical modification steps include N-alkylations, N-acylations, O-alkylations (etherifications), and O-acylations (esterifications). Chemical modification steps are also defined in the Schemes of Section 111B, and exemplified in Example 8.

The term "ether" refers to a cyclic hexadepsipeptide obtained by the replacement of a hydrogen atom from an hydroxyl by an $R^8$ replacement group by an O-alkylation reaction as defined in Scheme 1 (a) below. More particularly, the term "ether" encompasses ethers of any one of the β-OH of the 3-OH, MePro residues and the α and β-OH of the Acyl side chain (see Example 3 for atom numbering).

The term "ester" refers to a cyclic hexadepsipeptide obtained by the replacement of a hydrogen atom from an hydroxyl by a $C(O)R^9$ replacement group by an O-acylation reaction as defined in Scheme 1(b) below, wherein $C(O)R^9$ can also be a C-coupled amino acid. The term ester also encompasses ester equivalents including, without limitation, carbonate, carbamate, phosphonate or phosphate ester, sulfonate or sulfate ester, and the like. More particularly, the term "ester" encompasses esters of any one of the β-OH of the 3-OH,MePro residues and the α and β-OH of the Acyl side chain (see Example 3 for atom numbering).

The term "N-alkylated derivative" refers to a cyclic hexadepsipeptide obtained by the replacement of a hydrogen atom of a nitrogen atom by an $R^{10}$ replacement group by an N-alkylation reaction as defined in Scheme 2(a) below. More particularly, the term "N-alkylated derivative" encompasses substituted derivatives of the δ-NH amine of Pip1 and/or Pip2 residues (see Example 3 for atom numbering).

The term "N-acylated derivative" or "amide" refers to a cyclic hexadepsipeptide obtained by the replacement of a hydrogen atom from a nitrogen atom by a $C(O)R^{11}$ replacement group by an N-acylation reaction as defined in Scheme 2(b) below, wherein $C(O)R^{11}$ can also be a C-coupled amino acid. The term also encompasses amide equivalents including, without limitation, carbamates, ureas, guanidines, sulfonamides, and the like. More particularly, the term "amide" encompasses amides of the δ-NH amine of Pip1 and/or Pip2 residues (see Example 3 for atom numbering).

As used herein, abbreviations have their common meaning. Unless otherwise noted, the abbreviations "Ac", "Me", "Et", "Pr", "i-Pr", "Bu", "Bz", "Bn" and "Ph", respectively refer to acetyl, methyl, ethyl, propyl (n- or iso-propyl), iso-propyl, butyl (n-, iso-, sec- or tert-butyl), benzoyl, benzyl and phenyl. Abbreviations in the specification correspond to units of measure, techniques, properties or compounds as follows: "RT" and "Rt" mean retention time, "min" means minutes, "h" means hour(s), "μL" means microliter(s), "mL" means milliliter(s), "mM" means millimolar, "M" means molar, "mmole" means millimole(s), "eq" means molar equivalent(s). "High Pressure Liquid Chromatography" or "High Performance Liquid Chromatography" are abbreviated HPLC.

The term "alkyl" refers to linear or branched, saturated hydrocarbon groups. Examples of saturated alkyl groups include, without limitation, methyl, ethyl, n-propyl, isopropyl, sec-butyl, iso-butyl, n-butyl, pentyl, isoamyl, hexyl, heptyl, and the like. Alkyl groups may optionally be substituted with substituents selected from acyl, amino, acylamino, acyloxy, carboalkoxy, carboxy, carboxyamido, cyano, halo, hydroxyl, nitro, thio, alkyl, alkenyl, alkynyl, cycloalkyl, heterocycloalkyl, aryl, heteroaryl, alkoxy, aryloxy, sulfinyl, sulfonyl, oxo, guanidino and formyl.

The term "$C_{1-n}$alkyl", wherein n is an integer from 2 to 12, refers to an alkyl group having from 1 to the indicated "n" number of carbons. The $C_{1-n}$alkyl can be a straight or branched chain.

The term "alkenyl" refers to linear or branched hydrocarbon groups having from one to three carbon-carbon double bonds. Examples of alkenyl groups include, without limitation, vinyl, 1-propene-2-yl, 1-butene-4-yl, 2-butene-4-yl, 1-pentene-5-yl and the like. Alkenyl groups may optionally be substituted with substituents selected from acyl, amino, acylamino, acyloxy, carboalkoxy, carboxy, carboxyamido, cyano, halo, hydroxyl, nitro, thio, alkyl, alkenyl, alkynyl, cycloalkyl, heterocycloalkyl, aryl, heteroaryl, alkoxy, aryloxy, sulfinyl, sulfonyl, formyl, oxo and guanidino. The double bond portion(s) of the unsaturated hydrocarbon chain may be either in cis or trans configuration.

The term "$C_{2-n}$alkenyl", wherein n is an integer from 3 to 12, refers to an alkenyl group having from 2 to the indicated "n" number of carbons. The $C_{2-n}$alkenyl can be a straight or branched chain.

The term "alkynyl" refers to linear or branched hydrocarbon groups having at least one carbon-carbon triple bond. Examples of alkynyl groups include, without limitation, ethynyl, 1-propyne-3-yl, 1-butyne-4-yl, 2-butyne-4-yl, 1-pentyne-5-yl and the like. Alkynyl groups may optionally be substituted with substituents selected from acyl, amino, acylamino, acyloxy, carboalkoxy, carboxy, carboxyamido, cyano, halo, hydroxyl, nitro, thio, alkyl, alkenyl, alkynyl, cycloalkyl, heterocycloalkyl, aryl, heteroaryl, alkoxy, aryloxy, sulfinyl, sulfonyl, formyl, oxo and guanidine.

The term "$C_{2-n}$alkynyl", wherein n is an integer from 3 to 12, refers to an alkynyl group having from 2 to the indicated "n" number of carbons. The $C_{2-n}$alkynyl can be a straight or branched chain.

The term "cycloalkyl" or "cycloalkyl ring" refers to cyclic hydrocarbon groups comprising a saturated or partially unsaturated (non-aromatic) carbocyclic ring in a single or fused carbocyclic ring system having from three to fifteen ring members. Examples of cycloalkyl groups include, without limitation, cyclopropyl, cyclobutyl, cyclopentyl, cyclohexyl, cycloheptyl, cyclopentene, and cyclohexene. Cycloalkyl groups may optionally be substituted with substituents selected from acyl, amino, acylamino, acyloxy, carboalkoxy, carboxy, carboxyamido, cyano, halo, hydroxyl, nitro, thio, alkyl, alkenyl, alkynyl, cycloalkyl, heterocycloalkyl, aryl, heteroaryl, alkoxy, aryloxy, sulfinyl, sulfonyl and formyl.

The term "$C_{3-n}$cycloalkyl", wherein n is an integer from 4 to 15, refers to a cycloalkyl group having from 3 to the indicated "n" number of carbons.

The term "heterocycloalkyl", "heterocyclic" or "heterocycloalkyl ring" refers to a cycloalkyl group, as defined above, further containing one to four hetero atoms or hetero groups selected from O, N, NH, $NR^x$, $PO_2$, S, SO or $SO_2$ in a single or fused heterocyclic ring system having from three to fifteen ring members. Examples of a heterocycloalkyl, heterocyclic or heterocycloalkyl ring include, without limitation, pyrrolidino, tetrahydrofuranyl, dihydrofuran, tetrahydrodithienyl, tetrahydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3,1,0]hexanyl, 3-azabicyclo[4,1,0]heptanyl, 3H-indolyl, quinolizinyl, and the like. The foregoing heterocycloalkyl groups, as derived from the compounds listed above, may be C-attached or N-attached where such is possible. Heterocycloalkyl, heterocyclic or heterocycloalkyl ring may optionally be substituted with substituents selected from acyl, amino, acylamino, acyloxy, oxo, thiocarbonyl, imino, carboalkoxy, carboxy, carboxyamido, cyano, halo, hydroxyl, nitro, thio, alkyl, alkenyl, alkynyl, cycloalkyl, heterocycloalkyl, aryl, heteroaryl, alkoxy, aryloxy, sulfinyl, sulfonyl and formyl.

The term "$C_{3-n}$heterocycloalkyl", wherein n is an integer from 4 to 15, refers to an heterocycloalkyl group having from 3 to the indicated "n" number of atoms in the cycle and at least one hetero group as defined above.

The term "aryl" or "aryl ring" refers to common aromatic groups having "(4n+2)π electrons", wherein n is an integer from 1 to 3, in a conjugated monocyclic or polycyclic system and having from six to fourteen ring atoms. Aryl may be directly attached, or connected via a $C_{1-3}$alkyl group (also referred to as aralkyl). Examples of aryl include, without limitation, phenyl, benzyl, phenethyl, 1-phenylethyl, tolyl, naphthyl, biphenyl, terphenyl groups, and the like. Aryl may optionally be substituted with one or more substituent group selected from acyl, amino, acylamino, acyloxy, azido, alkylhio, carboalkoxy, carboxy, carboxyamido, cyano, halo, hydroxyl, nitro, thio, alkyl, alkenyl, alkynyl, cycloalkyl, heterocyclyl, aryl, heteroaryl, alkoxy, aryloxy, sulfinyl, sulfonyl and formyl.

The term "$C_{5-m}$aryl", wherein "m" is an integer from 5 to 14, refers to an aryl group having from 5 to the indicated "m" number of atoms, including carbon, nitrogen, oxygen and sulfur. The $C_{5-m}$aryl can be mono or polycyclic.

The term "heteroaryl" or "heteroaryl ring" refer to aryl rings, as defined above, further containing one to four heteroatoms selected from oxygen, nitrogen, sulfur or phosphorus. Examples of heteroaryl include, without limitation, pyridyl, imidazolyl, pyrimidinyl, pyrazolyl, triazolyl, tetrazolyl, furyl, thienyl, isooxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl groups. Heteroaryl may optionally be substituted with one or more substituent group selected from acyl, amino, acylamino, acyloxy, azido, alkylhio, carboalkoxy, carboxy, carboxyamido, cyano, halo, hydroxyl, nitro, thio, alkyl, alkenyl, alkynyl, cycloalkyl, heterocyclyl, aryl, heteroaryl, alkoxy, aryloxy, sulfinyl, sulfonyl and formyl. Heteroaryl may be directly attached, or connected via a $C_{1-3}$alkyl group (also referred to as heteroaralkyl). The foregoing heteroaryl groups, as derived from the compounds listed above, may be C-attached or N-attached where such is possible.

The term "$C_{5-n}$heteroaryl", wherein n is an integer from 5 to 14, refers to an heteroaryl group having from 5 to the indicated "n" number of atoms, including carbon, nitrogen, oxygen and sulphur atoms. The $C_{5-n}$heteroaryl can be mono or polycyclic.

The terms "halo" or "halogen" refers to bromine, chlorine, fluorine or iodine substituents.

The term "amino acid" refers to an organic acid containing an amino group. The term includes both naturally occurring and synthetic amino acids; therefore, the amino group can be but is not required to be, attached to the carbon next to the acid. A C-coupled amino acid substituent is attached to the heteroatom (nitrogen or oxygen) of the parent molecule via its carboxylic acid function. C-coupled amino acid forms an ester with the parent molecule when the heteroatom is oxygen, and an amide when the heteroatom is nitrogen. Examples of amino acids include, without limitation, alanine, valine, leucine, isoleucine, proline, phenylalanine, tryptophan, methionine, glycine, serine, threonine, cysteine, asparagine, glutamine, tyrosine, histidine, lysine, arginine, aspartic acid, glutamic acid, desmosine, ornithine, 2-aminobutyric acid, cyclohexylalanine, dimethylglycine, phenylglycine, norvaline, norleucine, hydroxylysine, allo-hydroxylysine, hydroxyproline, isodesmosine, allo-isoleucine, ethylglycine, beta-alanine, aminoadipic acid, aminobutyric acid, ethyl asparagine, and N-methyl amino acids. Amino acids can be pure L or D isomers or mixtures of L and D isomers.

The compounds of the present invention can possess one or more asymmetric carbon atoms and can exist as optical isomers forming mixtures of racemic or non-racemic compounds. The compounds of the present invention are useful as single isomers or as a mixture of stereochemical isomeric forms. Diastereoisomers, i.e., nonsuperimposable stereochemical isomers, can be separated by conventional means such as chromatography, distillation, crystallization or sublimation. The optical isomers can be obtained by resolution of the racemic mixtures according to conventional processes, including chiral chromatography (e.g. HPLC), immunoassay techniques, or the use of covalently (e.g. Mosher's esters) or non-covalently (e.g. chiral salts) bound chiral reagents to respectively form a diastereomeric ester or salt, which can be further separated by conventional methods, such as chromatography, distillation, crystallization or sublimation. The chiral ester or salt is then cleaved or exchanged by conventional means, to recover the desired isomer(s).

The purity of a compound or refers to the compound prior to its formulation in a pharmaceutical composition. The purity is referred to by "percent purity" and is a measure of the amount of the compound relative to the presence of components other then the compound. The purity may be measured by means including nuclear magnetic resonance (NMR)

spectroscopy, liquid chromatography/mass spectrometry (LC/MS), and liquid chromatography/UV spectroscopy (LC/UV).

The term "isolated" refers to a compound or product which has been removed from its original environment (e.g. reaction mixture, production culture or fermentation), which may be in a solid, semi-solid or oily form and refers to a compound or product that is at least 5%, 10%, 30%, 50%, 70%, 90%, 95% (% by weight) of the compound present in the mixture, provided that the mixture comprising the compound of the invention has demonstrable (i.e. statistically significant) biological activity such as cytotoxic or antibacterial activity when tested in conventional biological assays known to a person skilled in the art.

The term "crude" refers to a mixture of a compound that contains at least 50% of the compound by weight. The term "pure" or "purified" refers to substantially pure or essentially pure compound. The term "substantially pure" refers to a sample having at least 95%, by weight of the compound. The term "essentially pure" refers to a sample having at least 97% weight of the compound.

The term "pharmaceutically acceptable salt" refers to non-toxic salts synthesized from a compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, methanol, ethanol, isopropanol, or acetonitrile are preferred. Another method for the preparation of salts is by the use of ion exchange resins. The term "pharmaceutically acceptable salt" includes both acid addition salts and base addition salts, either of the parent compound or of a prodrug or solvate thereof. The nature of the salt is not critical, provided that it is pharmaceutically acceptable. Exemplary acids used in acid addition salts include, without limitation, hydrochloric, hydrobromic, hydroiodic, nitric, carbonic, sulfuric, sulfonic, phosphoric, formic, acetic, citric, tartaric, succinic, oxalic, malic, glutamic, propionic, glycolic, gluconic, maleic, embonic (pamoic), methanesulfonic, ethanesulfonic, 2-hydroxyethanesulfonic, pantothenic, benzenesulfonic, toluenesulfonic, sulfanilic, mesylic, cyclohexylaminosulfonic, stearic, algenic, β-hydroxybutyric, malonic, galactaric, galacturonic acid and the like. Suitable pharmaceutically acceptable base addition salts include, without limitation, metallic salts made from aluminium, calcium, lithium, magnesium, potassium, sodium and zinc or organic salts, such as those made from N,N'-dibenzylethylenediamine, chloroprocaine, choline, diethanolamine, ethylenediamine, N-methylglucamine, lysine, procaine and the like. Additional examples of pharmaceutically acceptable salts are listed in Berge et al (1977), *Journal of Pharmaceutical Sciences*, vol 66, no 1, pp 1-19, the content of which is incorporated herein by reference in its entirety. Preferred salts of Compound 1 are acid addition salts, such as acid addition salts of the nitrogen atom of the δ-NH amine of Pip1 and/or Pip2 residues (for example, δ-NH becomes δ-NH$_2^+$X$^-$, wherein X may be, for example, sulfate, chloride, acetate, and the like) (see Example 3 for atom numbering).

The term "solvate" refers to a physical association of a compound of this invention with one or more solvent molecules, whether organic or inorganic. This physical association includes hydrogen bonding. In certain instances the solvate will be capable of isolation. "Solvate" encompasses both solution-phase and isolable solvates. Exemplary solvates include hydrates, ethanolates, methanolates, hemiethanolates, and the like.

The term "pharmaceutically acceptable prodrug" means any pharmaceutically acceptable ester, salt of an ester or any other derivative of a compound of this invention, which upon administration to a recipient, is capable of providing, either directly or indirectly, a compound of this invention or a biologically active metabolite or residue thereof. Particularly favored salts or prodrugs are those with improved properties, such as solubility, efficacy, or bioavailability of the compounds of this invention when such compounds are administered to a mammal (e.g., by allowing an orally administered compound to be more readily absorbed into the blood) or which enhance delivery of the parent compound to a biological compartment (e.g., the brain or lymphatic system) relative to the parent species. As used herein, a prodrug is a drug having one or more functional groups covalently bound to a carrier wherein metabolic or chemical release of the drug occurs in vivo when the drug is administered to a mammalian subject. Pharmaceutically acceptable prodrugs of the compounds of this invention include derivatives of hydroxyl groups such as, without limitation, acyloxymethyl, acyloxyethyl and acylthioethyl ethers, esters, amino acid esters, phosphate esters, sulfonate and sulfate esters, and their metal salts, and the like; and derivatives of the amino groups such as, without limitation, alkyl carbamates and other carbamates, and amides, such as amino acid amides.

II. Compounds of the Invention

In one aspect, the invention relates to novel cyclic hexadepsipeptides, referred to herein as the compounds of the invention, and to pharmaceutically acceptable salts, solvates and prodrugs thereof.

Compound 1, may be characterized by any one of its physicochemical and spectral properties, such as mass and NMR spectra, detailed in Example 3.

In another aspect, compounds of the invention are characterized by the general Formula I:

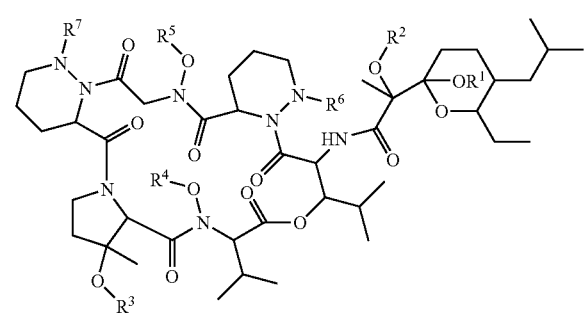

Formula I wherein, $R^1$, $R^2$ and $R^3$ are each independently selected from H, $R^8$ and $C(O)R^9$;

$R^4$ and $R^5$ are each independently selected from H, $C_{1-6}$alkyl, $C_{1-6}$alkenyl, and $C_{1-6}$alkynyl;

$R^6$ and $R^7$ are each independently selected from H, $R^{10}$ and $C(O)R^{11}$;

$R^8$ and $R^{10}$ are each independently selected form $C_{1-6}$alkyl, $C_{1-6}$alkenyl, $C_{1-6}$alkynyl, $C_{3-10}$cycloalkyl, and $C_{3-10}$heterocycloalkyl;

$R^9$ and $R^{11}$ are each independently selected from H, $C_{1-6}$alkyl, $C_{1-6}$alkenyl, $C_{1-6}$alkynyl, $C_{3-10}$cycloalkyl, $C_{3-10}$heterocycloalkyl, $C_{6-10}$aryl, and $C_{5-10}$heteroaryl, or $C(O)R^9$ and $C(O)R^{11}$ may each independently be a C-coupled amino acid;

wherein, when any of $R^1$, $R^2$, $R^3$, $R^4$, $R^5$, $R^6$, $R^7$, $R^8$, $R^9$, $R^{10}$ and $R^{11}$ comprises an alkyl, alkenyl, alkynyl, aryl, heteroaryl, cycloalkyl, or heterocycloalkyl group, then the alkyl, alkenyl, alkynyl, aryl, heteroaryl, cycloalkyl, or heterocycloalkyl group is optionally substituted with substituents selected from acyl, amino, acylamino, acyloxy, carboalkoxy, carboxy, carboxyamido, cyano, halo, hydroxyl, nitro, thio, $C_{1-6}$alkyl, $C_{2-7}$alkenyl, $C_{2-7}$alkynyl, $C_{3-10}$cycloalkyl, $C_{3-10}$heterocycloalkyl, $C_{6-10}$aryl, $C_{5-10}$heteroaryl, alkoxy, aryloxy, sulfinyl, sulfonyl, oxo, guanidino and formyl;

or a pharmaceutically acceptable salt, solvate or prodrug thereof.

In one embodiment, $R^1$ is H, and all other groups are as previously disclosed. In another embodiment, $R^2$ is H, and all other groups are as previously disclosed. In another embodiment, $R^1$ to $R^5$ are all H, and all other groups are as previously disclosed. In another embodiment, $R^4$ and $R^5$ are both H, and all other groups are as previously disclosed. In another embodiment, $R^1$ to $R^3$ are all H, and all other groups are as previously disclosed. In another embodiment, $R^1$ to $R^7$ are all H, and all other groups are as previously disclosed. In another embodiment, $R^6$ and $R^7$ are both H, and all other groups are as previously disclosed. In another embodiment, $R^1$ to $R^3$ are all $C(O)CH_3$, and all other groups are as previously disclosed. In another embodiment, $R^6$ and $R^7$ are both $C(O)CH_3$, and all other groups are as previously disclosed. In another embodiment, $R^1$ to $R^3$ are all $CH_3$, and all other groups are as previously disclosed. In another embodiment, $R^6$ and $R^7$ are both $CH_3$, and all other groups are as previously disclosed. The invention encompasses all esters, ethers, N-alkylated or N-acylated derivatives, and pharmaceutically acceptable salts, solvates and prodrugs of the foregoing compounds.

In another embodiment, the cyclic hexadepsipeptide is represented by any one of Compounds 1 to 30:

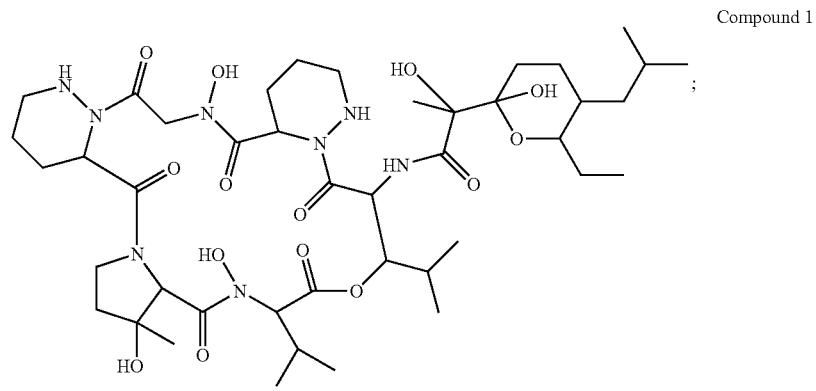

Compound 1

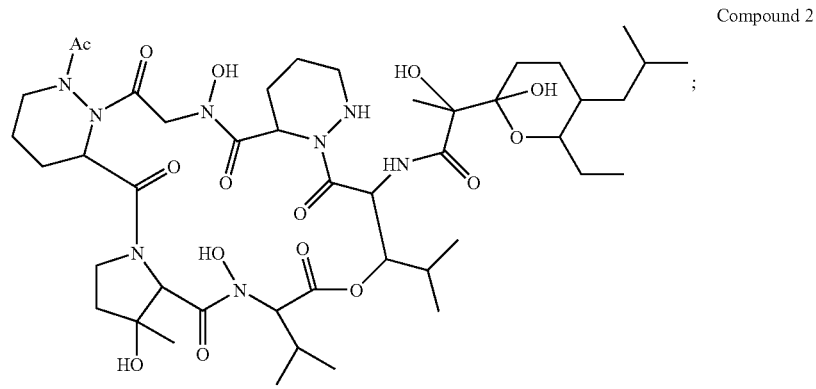

Compound 2

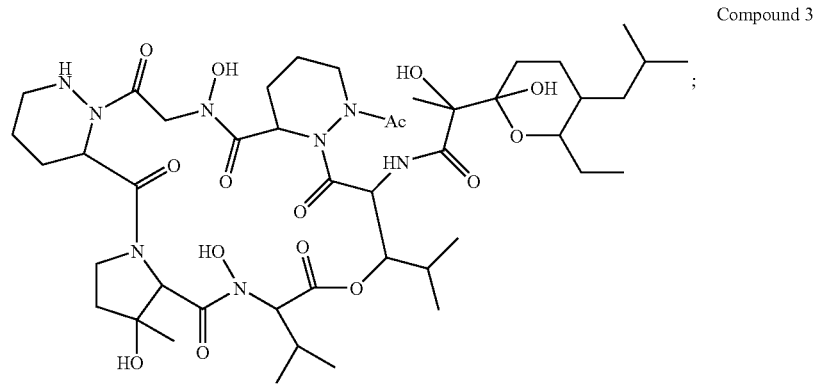

Compound 3

-continued
Compound 4
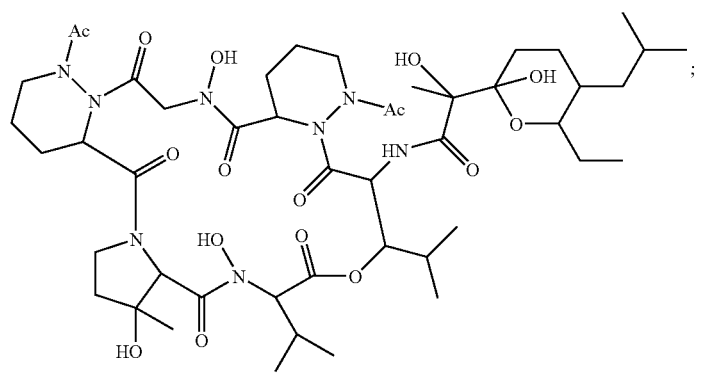
Compound 5
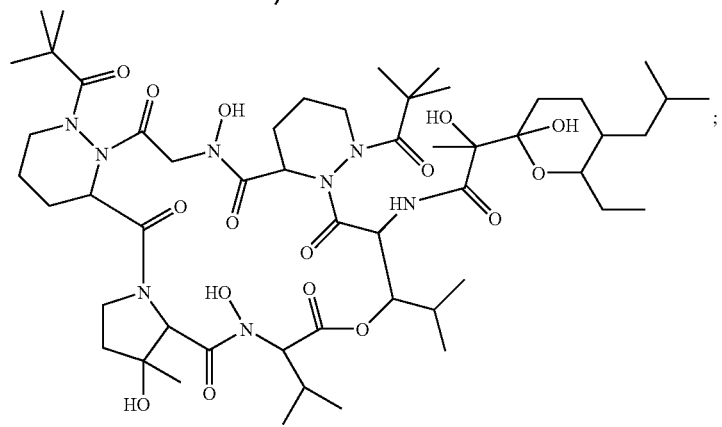
Compound 6
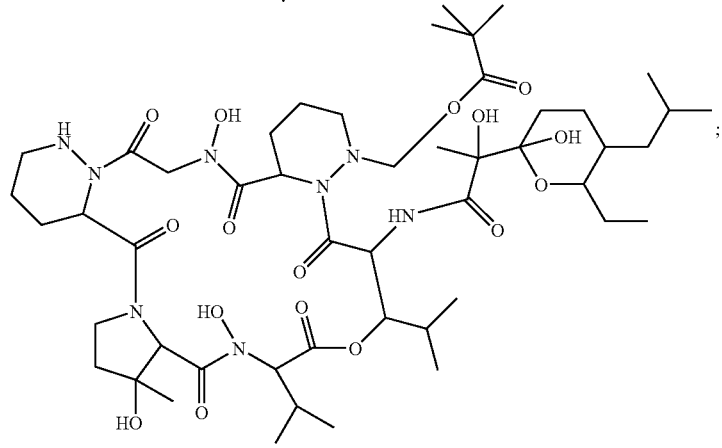
Compound 7
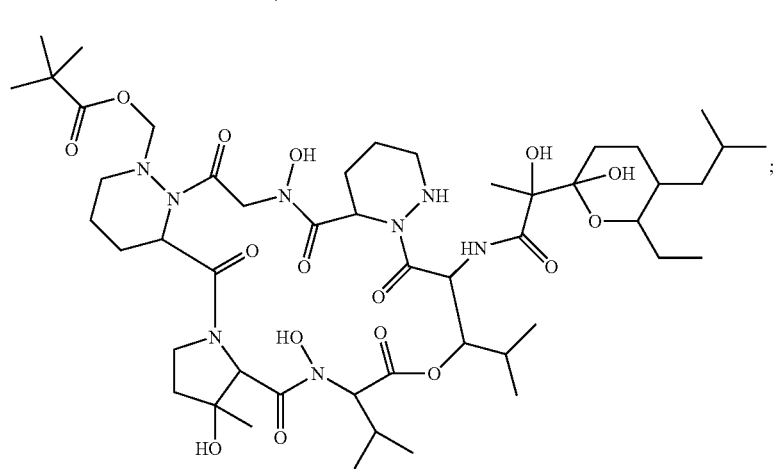

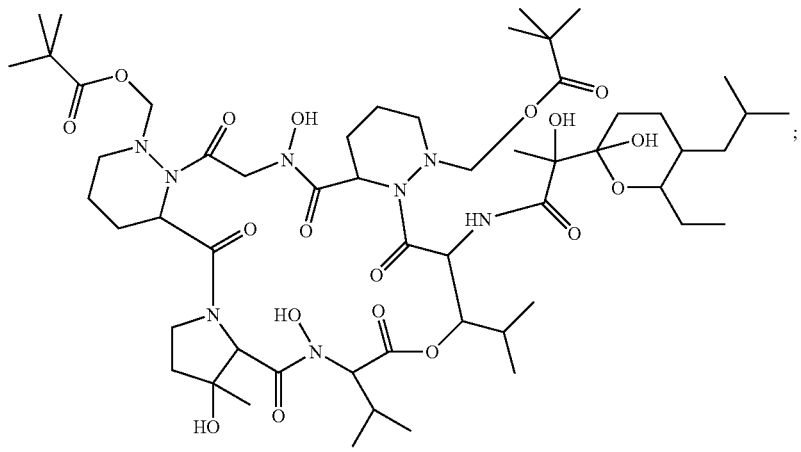
Compound 8
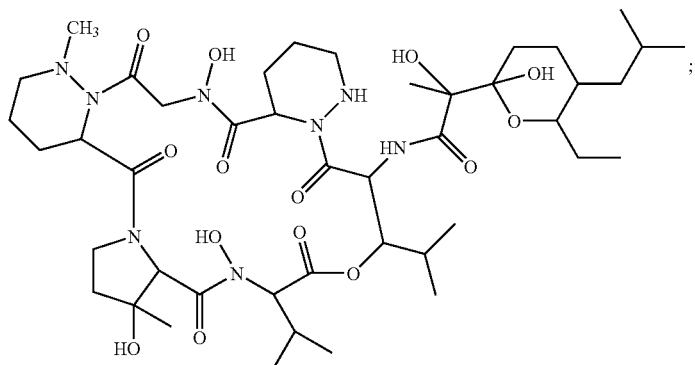
Compound 9
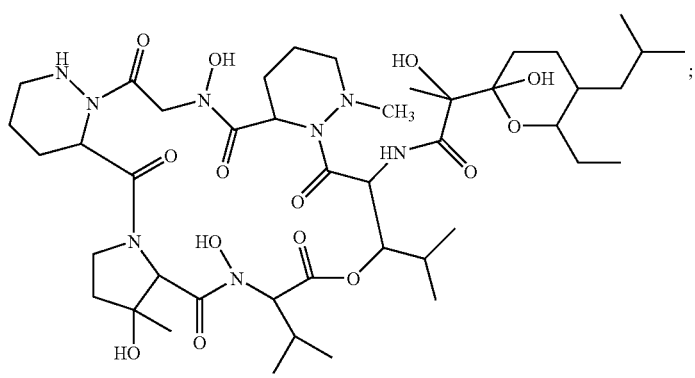
Compound 10
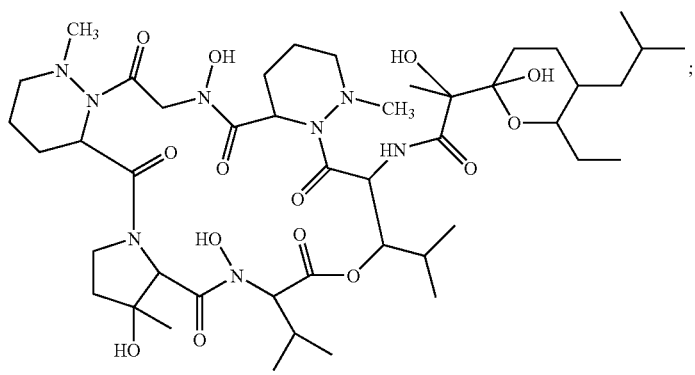
Compound 11

Compound 12
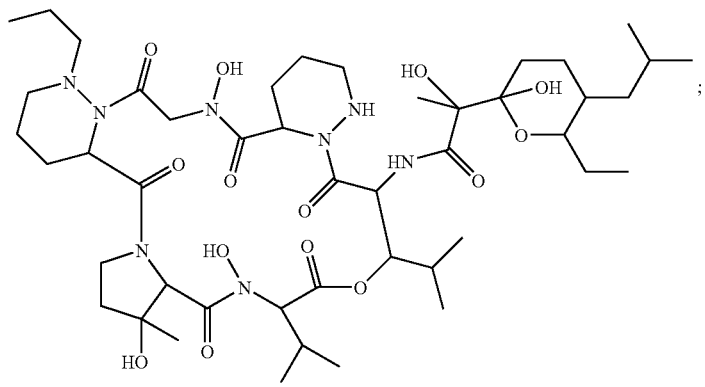
Compound 13
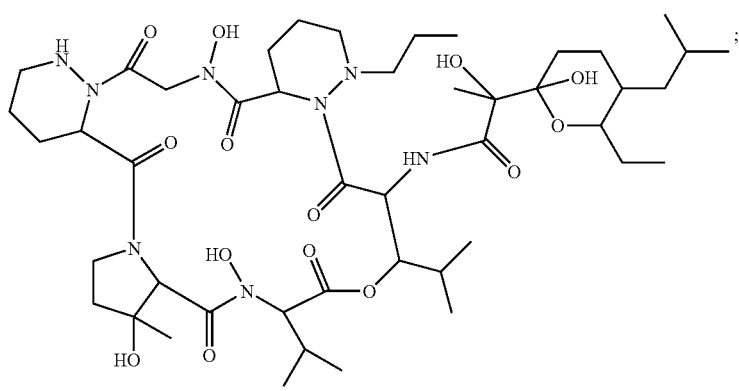
Compound 14
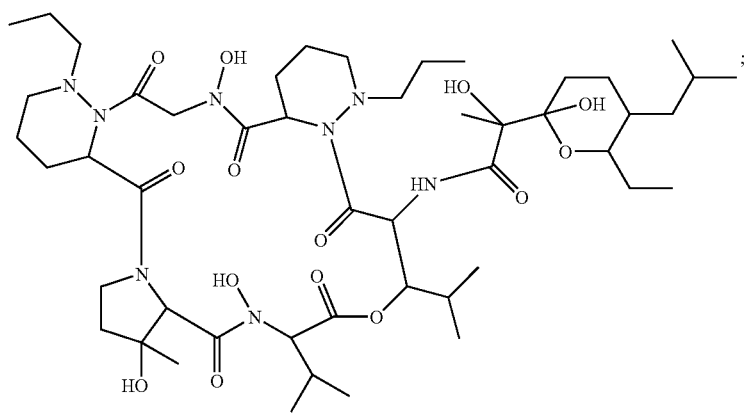
Compound 15
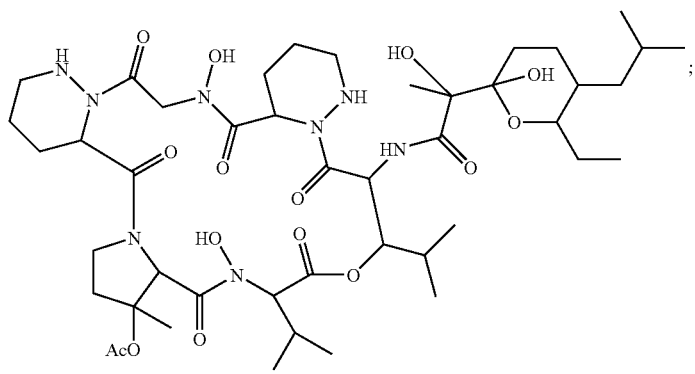

-continued
Compound 16
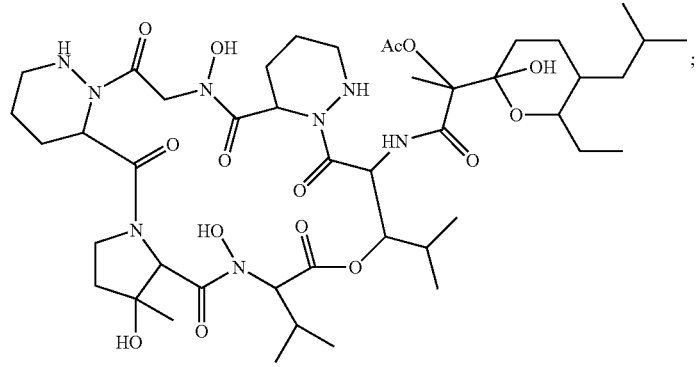
Compound 17
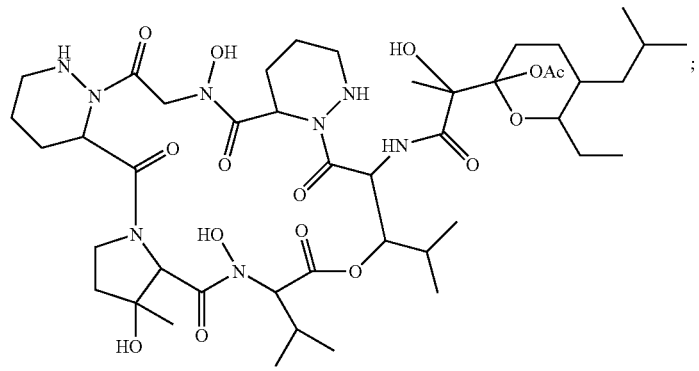
Compound 18
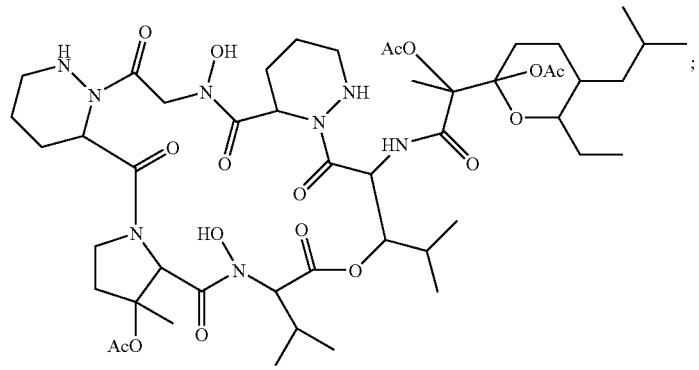
Compound 19
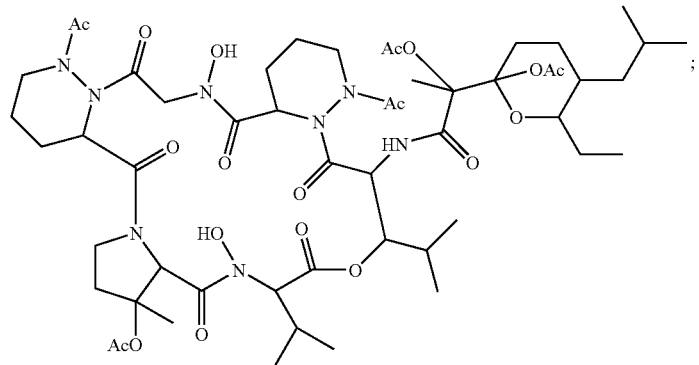

-continued
Compound 20
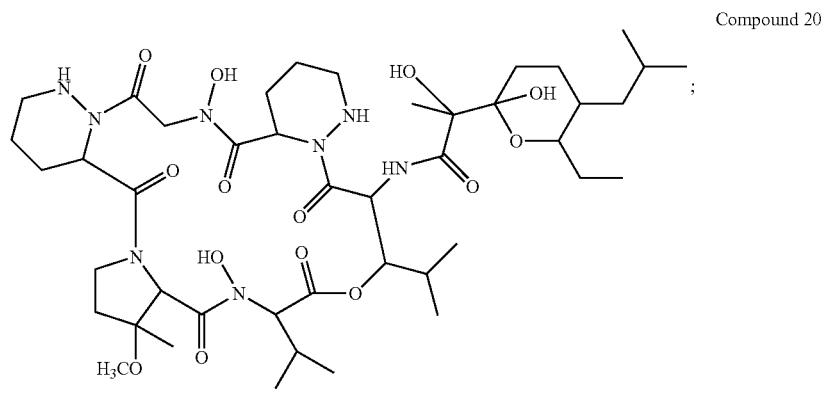
Compound 21
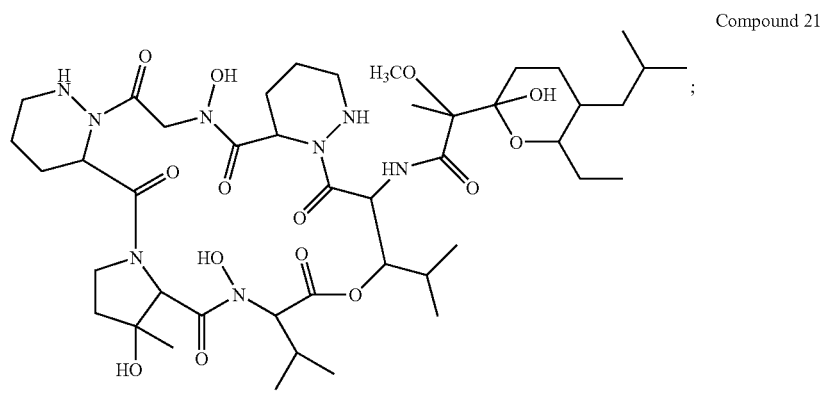
Compound 22
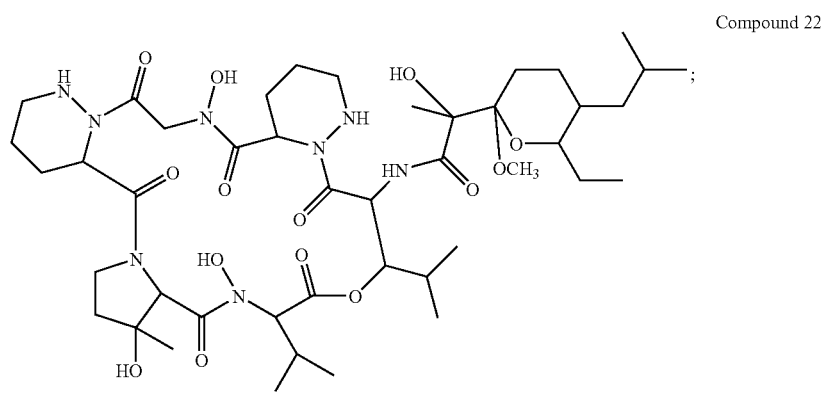
Compound 23
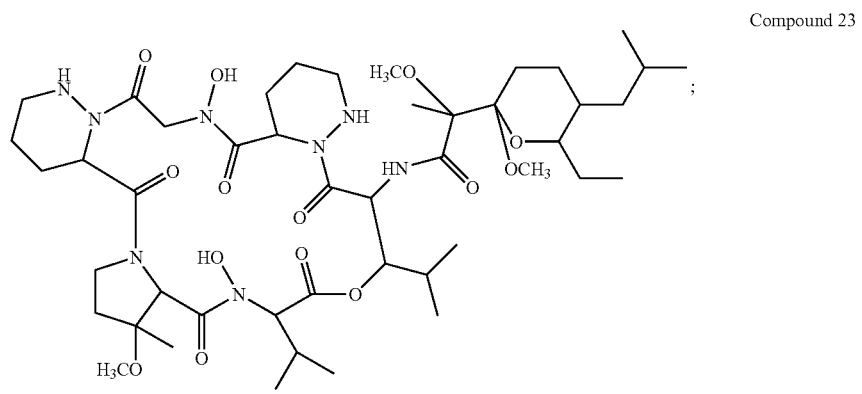

-continued
Compound 24
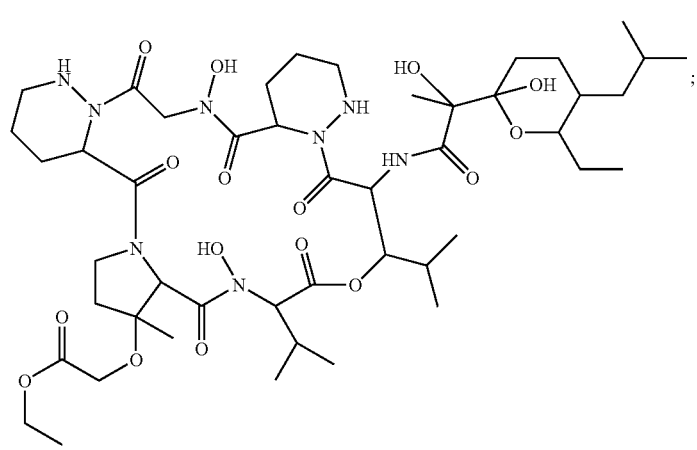
Compound 25
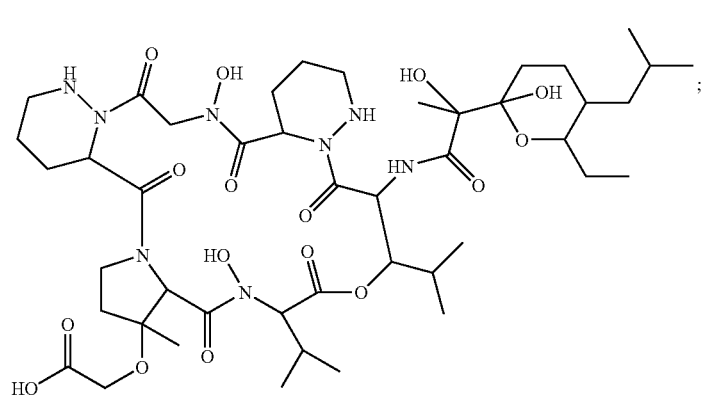
Compound 26
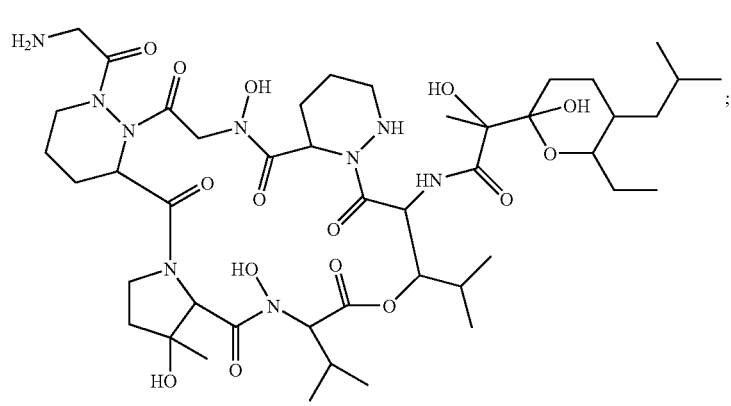
Compound 27
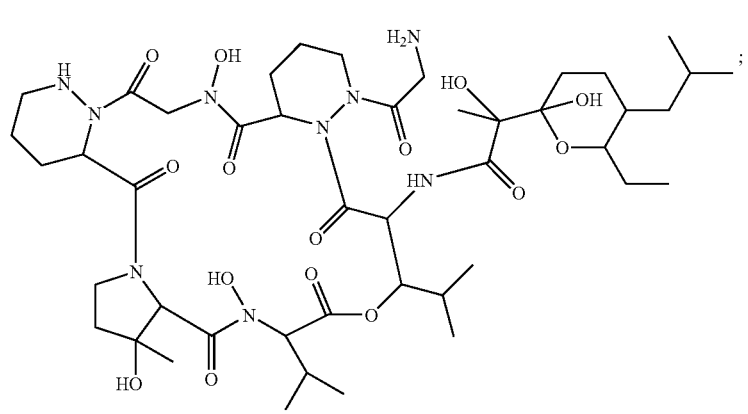

-continued

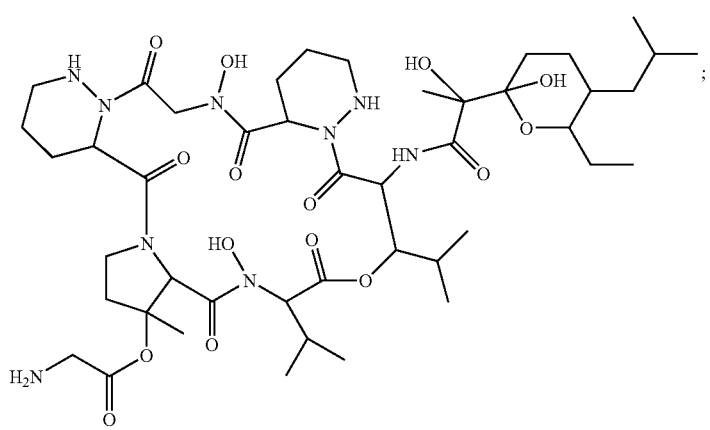

Compound 28

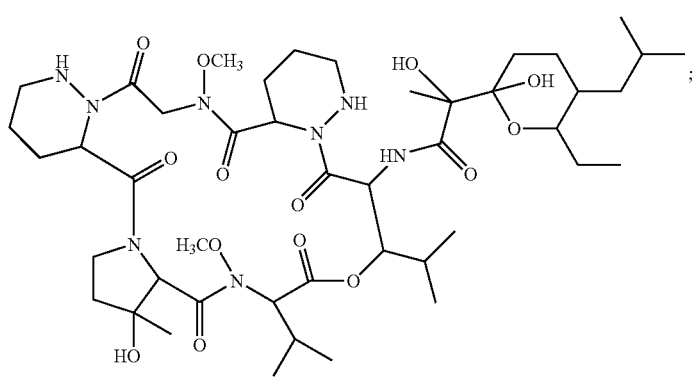

Compound 29

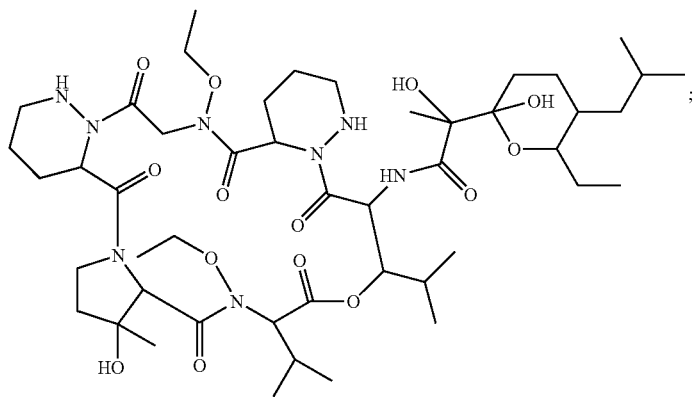

Compound 30 or an ether or ester, an N-alkylated or N-acylated derivative, or a pharmaceutically acceptable salt, solvate or prodrug, or salt of a prodrug of any one of Compounds 1 to 30.

Prodrugs of the compounds of the invention include compounds wherein one or more of the hydroxy or amine groups, or any other hydroxyl or amine group on the molecule is bounded to any group that, when administered to a mammalian subject, is cleaved to form the free hydroxyl group. Examples of prodrugs of hydroxyls include, but are not limited to, acetate, formate, hemisuccinate, benzoate, dimethylaminoacetate and phosphoryloxycarbonyl derivatives of hydroxy functional groups; dimethylglycine esters, aminoalkylbenzyl esters, aminoalkyl esters or carboxyalkyl esters of hydroxy functional groups. Carbamate and carbonate derivatives of the hydroxy groups are also included. Carbamates, such as alkyl carbamates, and amides, such as amino acid amides, of the amino groups are also encompassed by the invention. Derivatizations of hydroxyl groups also encompassed, are (acyloxy)methyl and (acyloxy)ethyl ethers, wherein the acyl group contains an alkyl group optionally substituted with groups including, but not limited to, ether, amino and carboxylic acid functionalities, or where the acyl group is an amino acid ester. Also included are phosphate and phosphonate esters, sulfate esters, sulfonate esters, which are in alkylated (such as bis-pivaloyloxymethyl (POM) phosphate trimester or —P(O)O$_2$Et$_2$) or in the salt form (such as sodium phosphate ester (—P(O)O$^-$$_2$Na$^+$$_2$)). For further examples of prodrugs used in anticancer therapy and their metabolism, see Rooseboom et al (2004), *Phamacol. Rev., vol* 56, 53-102, incorporated herein by reference. When the prodrug contains an acidic or basic moiety, the prodrug may also be prepared as its pharmaceutically acceptable salt.

The compounds of this invention may be formulated into pharmaceutical compositions comprised of a compound of the invention, in combination with a pharmaceutically acceptable carrier, as discussed in Section IV below.

III. Methods of Producing Cyclic Hexadepsipeptides

A. Fermentation

The terms "cyclic hexadepsipeptide-producing microorganism" and "producer of cyclic hexadepsipeptide," as used herein, refer to a microorganism that carries genetic information necessary to produce a cyclic hexadepsipeptide compound, whether or not the organism naturally produces the compound. The terms apply equally to organisms in which the genetic information to produce the cyclic hexadepsipeptide compound is found in the organism as it exists in its natural environment, and to organisms in which the genetic information is introduced by recombinant techniques.

Compound is produced by isolation of the fermentation broth of *Streptomyces* sp. strains. A preferred producer of cyclic hexadepsipeptides include microbial strain *Streptomyces* sp. Eco180 strain, sometimes referred to as strain 280, deposited on Sep. 22, 2005 with the International Depository Authority of Canada (IDAC), Bureau of Microbiology, Health Canada, 1015 Arlington Street, Winnipeg, Manitoba, Canada R3E,3R2, under Accession No. IDAC 220905-01. It is to be understood that the production of Compound 1 is not limited to the use of the particular strain Eco180. Rather, other cyclic hexadepsipeptide-producing organisms may be used, such as mutants or variants of Eco180 that can be derived from this organism by known means such as X-ray irradiation, ultraviolet irradiation, treatment with nitrogen mustard, phage exposure, antibiotic resistance selection and the like; or through the use of recombinant genetic engineering techniques. For examples, see *Manual of Industrial Microbiology and biotechnology*, Demain and Solomon, American Society for Microbiology, Washington D.C., 1986; Hesketh et al. (1997), *J. Antibiotics*, vol 50, no 6, 532-535; and Hosoya et al. (1998), *Antimicrobial Agents and Chemotherapy*, vol 42, no 8, 2041-2047), the content of which are incorporated herein by reference in their entirety.

The cyclic hexadepsipeptide compound may be biosynthesized by various microorganisms. Microorganisms that may synthesize the cyclic hexadepsipeptide compound include but are not limited to bacteria of the order Actinomycetales, also referred to as actinomycetes. Non-limiting examples of members belonging to the genera of Actinomycetes include *Nocardia, Geodermatophilus, Actinoplanes, Micromonospora, Nocardioides, Saccharothrix, Amycolatopsis, Kutzneria, Saccharomonospora, Saccharopolyspora, Kitasatospora, Streptomyces, Microbispora, Streptosporangium*, and *Actinomadura*. The taxonomy of actinomycetes is complex and reference is made to Goodfellow, *Suprageneric Classification of Actinomycetes* (1989); *Bergey's Manual of Systematic Bacteriology*, Vol. 4 (Williams and Wilkins, Baltimore, pp. 2322-2339); and to Embley and Stackebrandt, "The molecular phylogeny and systematics of the actinomycetes," *Annu. Rev. Microbiol.* (1994) 48:257-289, for genera that may synthesize the compounds of the invention. The content of which references is incorporated by reference in their entirety.

Cyclic hexadepsipeptide-producing microorganisms are cultivated in culture medium containing known nutritional sources for actinomycetes. Such media having assimilable sources of carbon, nitrogen, plus optional inorganic salts and other known growth factors, at a pH of about 6 to about 9. Suitable media include, without limitation, the growth media provided in Table 1. Microorganisms are cultivated at incubation temperatures of about 18° C. to about 40° C. for about 3 to about 40 day

TABLE 1

Examples of Growth Media (AA to GA) for Production of Compound 1

| | AA | AB | BA | CA | CB | CI | DA | DY | DZ | EA | ES | ET | FA | GA*[4] |
|---|---|---|---|---|---|---|---|---|---|---|---|---|---|---|
| PH*[5] | | | | 7 | 7 | 7 | 7 | 7 | 7 | 7 | | | 7.0 | |
| Glucose | 10 | | 10 | 10 | | | 10 | | 5 | 5 | 40 | | 10 | 10 |
| Sucrose | 15 | | | | 20 | | | | | | | | | 103 |
| Mannitol | | 25 | | | | | | | | | | | | |
| Lactose | | | | | | | | | | 50 | | | | |
| Cane molasses | | | | 15 | 5 | | 10 | | 10 | | | 60 | 15 | |
| Soluble starch | | 25 | 10 | | | | 5 | | 15 | | | 20 | | |
| Corn starch | | | | | | | | 10 | | | | | | |
| Corn dextrin | 40 | | | | | | | | | | | | | |
| Potato dextrin | | | | 40 | | 20 | 20 | | | | | | 40 | |
| Corn steep solid | | | | | | | 5 | | | 5 | | | | |
| Dried yeast | | | | | | | | | | | 5 | | | |
| Yeast extract | | | | | | | | | | | | | | 5 |
| Pharmamedia ™ | | | | | | | | 5 | | | | | | |
| Glycerol | | 25 | | | | 20 | 10 | | | 15 | | | | |
| N-Z Amine A | 10 | | | 10 | | | | | | | | | 10 | |
| Soybean powd. | | | 15 | | | | | | | | | | | |
| Soybean flour | | | | | | | 5 | | | 10 | | | | |
| Fish meal | | | | | | 10 | | | 10 | | | 20 | | |
| Bacto-peptone | | | | | 2 | 5 | | | | 5 | | | | |
| L-Glutamine | | 5.84 | | | | | | | | | | | | |
| L-Arginine | | 1.46 | | | | | | | | | | | | |
| MgSO$_4$•7H$_2$O | 1 | 0.5 | 1 | 1 | 0.2 | | 0.5 | | | 0.5 | 1 | | 1 | |
| MgCl$_2$•6H$_2$O | | | | | | | | | | | | | | 10.12 |
| CaCO$_3$ | 2 | | | 2 | 5 | 2 | 3 | 1 | 5 | 3 | 2 | 2 | 2 | |
| NaCl | | 1 | 3 | | | | | | | | 1 | | | |
| KH$_2$PO$_4$ | | 1 | | | | | | | | | | | | |
| K$_2$HPO$_4$ | | | 1 | | | | | | | | | | | |
| Na$_2$HPO$_4$ | | | | | | | | | | | | | 3 | |
| FeSO$_4$•7H$_2$O | | | | | 0.1 | | | | | | 1 mg | | | |
| FeCl$_2$•4H$_2$O | | | | | | | 0.1 | | | 0.1 | | | | |
| KI | | | | | 0.5 | | | | | | | | | |
| NaI | | | | | | | | .5 mg | | | .5 mg | 0.5 | | |
| (NH$_4$)$_2$SO$_4$ | | | | | 2 | | | | | 2 | 2 | | | |

TABLE 1-continued

| Component | | | | | | | | | | | | |
|---|---|---|---|---|---|---|---|---|---|---|---|---|
| $K_2SO_4$ | | | | | | | | | | | | 0.25 |
| $ZnCl_2$ | | | | 0.1 | | 0.1 | | | | | | |
| $ZnSO_4 \cdot 7H_2O$ | | | | | | | 1 mg | | | | | |
| $MnCl_2 \cdot 4H_2O$ | | | | 0.1 | | 0.1 | 1 mg | | | | | |
| $CuSO_4 \cdot 5H_2O$ | | | | | 50 mg | | | | 0.1 | | | |
| Phytic acid | | | | 1 | | | | | | | | |
| Casamino acid | | | | | | | | | | | | 0.1 |
| Trace element solution*[1] ml/L | | 2 | | | | | | | | | | |
| Trace element solution*[2] ml/L | | | 1 | | | | | | | | | |
| Trace element solution*[3] ml/L | | | | | | | | | | | | 2 |

Examples of Growth Media (HA to MU) for Production of Compound 1

| Component | HA | IA | IB | JA | KA | KC | KD | KE | KF | KG | KH | LA | MA | MC | MU |
|---|---|---|---|---|---|---|---|---|---|---|---|---|---|---|---|
| PH*[5] | | 6.2 | | 7.3 | 5.7 | 6 | 7 | | 6.9 | 6.9 | 7 | 7 | 7.5 | 7 | 5 |
| Glucose | 10 | 20 | | | 10 | 2 | | | 1 | 10 | 10 | | | 10 | 5 |
| Sucrose | 340 | | | | | | | | | | | | | | |
| Mannitol | | | 40 | | | | | | | | | | | | 25 |
| Cane molasses | | | | | | | | | | 20 | | | | | |
| Soluble starch | | 30 | | | | | 20 | | 24 | | | 25 | 25 | 10 | |
| Corn starch | | | | 30 | | | | | | | | | | | |
| Potato dextrin | | | | | | | 15 | | | | 20 | | | | |
| Corn steep liq. | | | 15 | | 10 | | | | | | | | | | |
| Distiller's Solub. | | | | | | | | 15 | | | | | | | |
| Dried yeast | | | | | 5 | | | | | | | 5 | 2 | | |
| Yeast extract | 3 | | 10 | | | | | 3 | | 5 | | 5 | | | |
| Malt extract | 3 | | | 35 | | | | | | | | | | | |
| Pharmamedia ™ | | | | 15 | | | | | 10 | | | | | | |
| Glycerol | | | | | | 5 | | | 30 | | | | | | |
| N-Z Amine A | | | 33 | | | | | | | | 5 | | | | |
| Soybean powder | | 40 | | | 10 | | | | | | | 15 | 15 | | 10 |
| Soybean meal | | | | | | | 10 | | | | | | | 15 | |
| Meat extract | | | | | | | | 3 | | | | | | | |
| Beef extract | | | | | | | | | 3 | | | | | | 10 |
| Fish meal | | | | | | | | 10 | | | | | | | |
| Bacto-peptone | 5 | | | | | | 3 | | 3 | 10 | | | | | 5 |
| Tomato paste | | | | | | 40 | | | | | | | | | |
| Oatmeal | | | | | | 15 | | | | | | | | | |
| $MgSO_4 \cdot 7H_2O$ | | | | | | | | | | | | | 1 | | |
| $MgCl_2 \cdot 6H_2O$ | 1 | | | | | | | | | | | | | | |
| $CaCO_3$ | | 1 | | | 2 | 2 | | 3 | 6 | 4 | 1 | | 2 | 4 | 3 |
| NaCl | | | | | | 5 | | 1 | | | | | 5 | 3 | 2 |
| $KH_2PO_4$ | | | 9 | | | | | | | | | | | | |
| $FeSO_4 \cdot 7H_2O$ | | | | | | | | | | | | | 1 mg | | |
| $Fe(NH_4)_3$ citrate | | | | | | | | | | 0.1 | | | | | |
| $(NH_4)_2SO_4$ | | | 5 | | | | | | | | | | 2 | | |
| $NH_4NO_3$ | | 3 | | | | | | | | | | | | | |
| $ZnSO_4 \cdot 5H_2O$ | | | | | | | | | | | | | 2 mg | | |
| $MnCl_2 \cdot 4H_2O$ | | | | | | | | | | | | | 8 mg | | |
| $CuSO_4 \cdot 5H_2O$ | | | | | | | | | | | | | 7 mg | | |
| $CoCl_2 \cdot 2H_2O$ | | | | | | | 50 μg | | | | | | | | |

Examples of Growth Media (MY to SF) for Production of Compound 1

| Component | MY | NA | NE | NF | NG | OA | PA | PB | QB | RA | RB | RC | RM | SF |
|---|---|---|---|---|---|---|---|---|---|---|---|---|---|---|
| PH*[5] | 7 | 7 | 7 | 7.2 | 7.2 | 7 | 7 | 6 | 7.2 | 7.5 | 7 | 7.2 | 6.9 | 7 |
| Glucose | | | 30 | | 40 | 10 | 5 | 22.5 | 12 | | 10 | | 10 | 25 |
| Sucrose | | | | | | | | | | | | | 100 | |
| Maltose | 4 | | | | | | | | | | | | | |
| Cane molasses | | 10 | | | | | | | | | 10 | | | 3.75 |
| Soluble starch | | | | 20 | | | 10 | 7.5 | 10 | 20 | | | | |
| corn starch | | | | | | | | | | | 60 | | | |
| Corn dextrin | | | | | | | | | | | | 10 | | |
| Linseed meal | | | | | | | | | | | 15 | | | |
| Corn steep liq. | | | | | | 3 | | | 5 | | | | | |
| Dry yeast | | | | | | | | 3.5 | | | | | | |
| Yeast extract | | 4 | | 5 | | 3 | 2 | | | 2.5 | 5 | | 5 | |
| Malt extract | | 10 | | | | 3 | | | | | | | | |
| Pharmamedia ™ | | | | | | | | | 10 | 5 | | | | |
| Glycerol | | 20 | | | | 5 | 10 | | | | | | | |
| N-Z Amine A | | | | | | | | | | | | | | 1.25 |
| Soybean powd. | | | | | | | | | | | | | | 18.75 |
| Soybean meal | | | | 20 | | | | 25 | | | | | | |
| Beef extract | | | 5 | | | 3 | 5 | | | | | | | |
| Bacto-peptone | | | 1 | 5 | | | 3 | | | | | | | |
| Bacto-Tryptone | | | | | | | | | | | | 10 | | |
| Casamino acid | | 5 | | | 15 | | 1 | | | | | | 0.1 | |
| Thiamine | | | | | | 0.1 | .01 | | | | | | | |

TABLE 1-continued

| Component | C1 | C2 | C3 | C4 | C5 | C6 | C7 | C8 | C9 | C10 | C11 | C12 |
|---|---|---|---|---|---|---|---|---|---|---|---|---|
| $MgSO_4 \cdot 7H_2O$ | | | | | | | | | | | 1 | |
| $MgSO_4$ | | | 12.5 | | | | | | | | | |
| $MgCl_2 \cdot 6H_2O$ | | | | | | | | | | | 10.13 | |
| $CaCO_3$ | 4 | 2 | 2 | 2 | 2 | 2 | 6 | 3 | 10 | 5 | | 3 |
| NaCl | | 5 | 5 | 5 | | | | 1 | | 2 | | 8 |
| Na acetate | | | | | | | | | | | | |
| $K_2HPO_4$ | | | | | 1 | | | .75 | | | | |
| $K_2SO_4$ | | | | | | | | | | | .25 | |
| $FeSO_4 \cdot 7H_2O$ | | | | | | | | | | | 1 | |
| $(NH_4)_2SO_4$ | | | | | | | | | | | 1 | |
| $NH_4H_2PO_4$ | | | | | | | | | | | 1 | |
| $ZnSO_4 \cdot 5H_2O$ | | | 5 mg | | | | | | | | | |
| $ZnSO_4 \cdot 7H_2O$ | | | | | | | 0.5 | | | | | |
| $MnSO_4$ | | | 5 mg | | | | | | | | | |
| $CuSO_4 \cdot 5H_2O$ | | | 5 mg | | | | | | | | | |
| Proflo oil (ml) | | | | | | | 4 | | | | | |
| MOPS | | | | | | | | | | | 21 | |
| Trace element solution*[3] ml/L | | | | | | | | | | | | 2 |

Examples of Growth Media (SP to WS) for Production of Compound 1

| Component | SP | TA*[4] | VA | VB | WA | XA | YA | ZA | WS |
|---|---|---|---|---|---|---|---|---|---|
| PH*[5] | 7 | | 7 | 7 | 7.3 | 7 | 6.8 | | |
| Glucose | 20 | | 50 | 10 | 0.4 | | 5 | | |
| Sucrose | | 103 | | 20 | | | | 10 | 40 |
| Lactose | | | | | | | 5 | | |
| Cane molasses | | | | 20 | | | | | |
| Soluble starch | | | | | | | | | |
| Corn steep solid | | | | | | | | | |
| Dried yeast | | | | | | | | | 5 |
| Yeast extract | 3 | 5 | | | 0.8 | 10 | 3 | 4 | |
| Pharmamedia ™ | | | | | | | | | |
| N-Z Amine A | | | | | | 10 | | 8 | |
| Soybean flour | | | 30 | | | | | | |
| Beef extract | 5 | | | | | 5 | 8 | | |
| Soytone-peptone | | | | 5 | | | | | |
| Bacto-peptone | 5 | | | | | | 10 | | |
| $MgSO_4 \cdot 7H_2O$ | | | | | | 3 | 0.2 | 0.3 | |
| $MgCl_2 \cdot 6H_2O$ | | 10.1 | | | | | | | |
| $CaCO_3$ | 3 | | 6 | 2.5 | | | | | 2 |
| NaCl | 5 | | 5 | | | | | | 1 |
| $KH_2PO_4$ | | | | | | | 2.5 | | |
| $K_2HPO_4$ | | | | 2 | 1 | | 2.5 | 3 | 1 |
| $(NH_4)_2SO_4$ | | | 3 | | | | | | 2 |
| $K_2SO_4$ | | .25 | | | | | | | |
| $MnSO_4 \cdot H_2O$ | | | | | | | 50 mg | | |
| $MnCl_2 \cdot 4H_2O$ | | | | | | | | | 1 mg |
| $MgSO_4$ | | | | | | | | | 1 |
| $FeSO4 \cdot 7H2O$ | | | | | | | | | 1 mg |
| $ZnSO4 \cdot 7H2O$ | | | | | | | | | 1 mg |
| NaI | | | | | | | | | .5 mg |
| Casamino acid | | 0.1 | | | 0.5 | | | | |
| Proflo oil | | | | | | | | | |
| Trace element solution*[1] ml/L | | 2 | | | | | | | |

Media KC, KD, KF and KG are prepared with tap water
In Table 1: Unless otherwise indicated all the ingredients are in gm/L.
*[1]Solution of trace elements contains: 0.1 g $FeSO_4 \cdot 7H_2O$; 0.01 $MnSO_4 \cdot H_2O$; 0.01 g $CuSO_4 \cdot 5H_2O$; 0.01 $ZnSO_4 \cdot 7H_2O$; one drop concentrated $H_2SO_4$; dissolved in 100 ml dd$H_2O$.
*[2]Solution of trace elements contains: 0.1 g $FeSO_4 \cdot 7H_2O$; 0.8 g $MnCl_2 \cdot 4H2O$; 0.7 g $CuSO_4 \cdot 5H_2O$; 0.2 $ZnSO_4 \cdot 7H_2O$; one drop concentrated $H_2SO_4$; dissolved in 100 ml dd$H_2O$.
*[3]Solution of trace elements contains: $ZnCl_2$ 40 mg; $FeCl_3 6H_2O$ (200 mg); $CuCl_2 2H_2O$ (10 mg); $Na_2B_4O_7 10H_2O$ (10 mg); $(NH_4)_6MO_7O_{24} 4H_2O$ (10 mg) per litre.
*[4]To a liter media GA add: 10 ml $KH_2PO_4$ (0.5% solution); 80 ml $CaCl_2 \cdot 2H_2O$ (3.68% solution); 15 ml L-proline (20% solution); 100 ml TES buffer (5.73% solution, pH 7.2); 5 ml NaOH (1N solution).
*[5]The pH is adjusted as marked prior to the addition of $CaCO_3$.

The culture media inoculated with a cyclic hexadepsipeptide-producing microorganism may be aerated by incubating the inoculated culture media with agitation, for example, shaking on a rotary shaker, a shaking water bath, or in a fermentor. Aeration may also be achieved by the injection of air, oxygen or an appropriate gaseous mixture to the inoculated culture media during incubation. Following cultivation, the cyclic hexadepsipeptide compound can be extracted and isolated from the cultivated culture media by techniques known to a person skilled in the art and/or disclosed herein, including for example centrifugation, chromatography, adsorption, filtration. For example, the cultivated culture media can be optionally acidified and mixed with a suitable organic solvent such as methanol, ethanol, n-butanol, ethyl acetate, n-butyl acetate or 4-methyl-2-pentanone. The organic layer can be separated from the mycelial cake for example, by centrifugation and decantation or filtration. The mycelial cake is further optionally extracted with an organic solvent, and the organic extracts combined. The organic layer is further optionally treated, for example by: aqueous washings, precipitation, filtration and the like, followed by removal of the solvent, for example, by evaporation to dryness under vacuum. The resulting residue can optionally be reconstituted with for example water, ethyl ether, ethanol, ethyl acetate, methanol or a mixture thereof, and re-extracted in a two-phase system with a suitable organic solvent such as hexane, carbon tetrachloride, methylene chloride or a mixture thereof. After removal of the solvent, the compound can be further purified by the use of standard techniques such as normal and reverse-phase liquid chromatography, crystallization, sublimation, adsorption, mass exclusion chromatography, and the like.

B. Chemical Modifications:

The cyclic hexadepsipeptide Compound 1 is biosynthesized by microorganism and isolated as described herein. Compound 1 is subjected to random and/or directed chemical modifications to form compounds that are derivatives or structural analogues. Such derivatives or structural analogues having similar functional activities are within the scope of the present invention. The cyclic hexadepsipeptide may be modified by one or more chemical modification steps, using methods known in the art and described herein. Examples of chemical modifications procedures are also provided in Example 8.

Cyclic hexadepsipeptides that are derivatives of Compound 1, for example those identified herein as the compounds of Formula I and their derivatives, and Compounds 2 to 30, are generated by standard organic chemistry approaches. General principles of organic chemistry required for making and manipulating the compounds described herein, including functional moieties, reactivity and common protocols are described, for example, in "*Advanced Organic Chemistry,*" $4^{th}$ Edition by Jerry March (1992), Wiley-Interscience, USA, incorporated herein by reference in its entirety. In addition, it will be appreciated by one of ordinary skill in the art that the synthetic methods described herein may use a variety of protecting groups, whether or not they are explicitly described. A "protecting group" as used herein means a moiety used to block one or more functional moieties such as reactive groups including oxygen, sulfur or nitrogen, so that a reaction can be carried out selectively at another reactive site in a polyfunctional compound. General principles for the use of protective groups, their applicability to specific functional groups and their uses are described for example in T. H. Greene and P. G. M. Wuts, Protective Groups in Organic Synthesis, $3^{rd}$ Edition, John Wiley & Sons, New York (1999), incorporated herein by reference in its entirety.

Alcohols are protected, if necessary with, for example: silyl ethers (e.g. TMS: trimethylsilyl, TIPS: triisopropylsilyl), acetals (e.g. MOM: methyloxymethyl, BOM: benzyloxymethyl, THP: tetrahydropyranyl), esters (e.g. acetate, benzoyl) and ethers (e.g. Bn: benzyl). Alcohols are deprotected by conditions such as: TBAF (tetrabutylammonium fluoride) for silyl ethers, aqueous acid catalysis for acetals and esters, saponification for esters, and hydrogenolysis for Bn and BOM.

Amine are protected, if necessary, using standard amine protecting groups, for example, carbamates (such as t-butyl (BOC) and benzyl (CBZ)), fluorene derivatives (such as FMOC: N-(9-fluorenylmethoxycarbonyl)-), and the like. Amine is deprotected by conditions such as: acid hydrolysis for BOC, hydrogenolysis for CBZ, or base treatment for FMOC. All protection and deprotection conditions are demonstrated in the Greene et al reference above.

Those skilled in the art will readily appreciate that many synthetic chemical processes may be used to produce derivatives of Compound 1. The following schemes are exemplary of the routine chemical modifications that may be used to produce compounds of the invention. Any chemical synthetic process known to a person skilled in the art providing the structures described herein may be used and are therefore comprised in the present invention.

Scheme 1: Alcohol(s) modifications (O-alkylations and O-acylations)

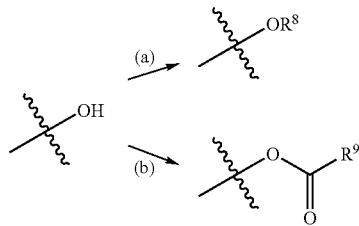

wherein, $R^8$ and $R^9$ are as previously described.

In Scheme 1, alcohols of the 3-OH,MePro residue (β-OH) and the Acyl side chain residue (α-OH and β-OH) (for position numbers, see Example 3) are independently alkylated (to produce an ether) or acylated (to produced an ester). In Scheme 1(a), allylation is accomplished with an alkylating agent such as $R^8X$, wherein X is a suitable leaving group such as Br, I, a sulfate or sulfonate (e.g mesylate, tosylate, etc), in the presence of a base such as triethylamine or diisoprylethylamine, or a stronger base such as DBU (1,8-diazabicyclo [5.4.0]undec-7-ene), and the like. In Scheme 1(b), an alcohol is converted to ester when reacted with an activated carboxylic acid ($R^9C(O)X$) such as an acid halide, anhydride, N-hydroxysuccinimide ester, or a carboxylic acid activated by a coupling agent (e.g.: EDC (1-(3-dimethylaminopropyl)-3-diisopropylethylcarbodiimide hydrochloride); or HATU (O-(7-azabenzotriazol-1-yl)-N,N,N',N'-tetramethyluronium hexafluorophosphate)) with a base (e.g., pyridine or N,N-diisopropylethylamine (DIPEA)) and optional acatalysts such HOBt (1-hydroxybenzotriazole hydrate) and/or DMAP (4-(dimethylamino)pyridine). Esters encompass ester equivalents and are produced by reacting the activated equivalent (e.g. reaction with ethyl chloroformate results in a carbonate). Hydroxamic acids (of N—OHVal and N—OHGly) are also esterified by alkylating the N—OH group using the method described in (a).

Scheme 1 is used to obtain, for example, Compounds 15 to 24 and 28 to 30 from Compound 1; and to produce ethers or esters, or any of the Compounds of Formula I comprising an O-alkyl or O-acyl group.

Scheme 2: Amine modifications (N-alkylations and N-acylations)

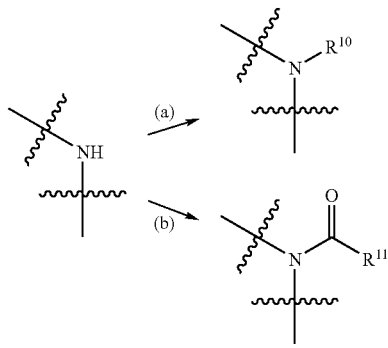

wherein, $R^{10}$ and $R^{11}$ are as previously described.

In Scheme 2, δ-NH amine groups of both Pip1 and Pip2 residues (for position, see Example 3) is optionally alkylated or acylated. In Scheme 2(a), an amine is alkylated using an $R^{10}X$ alkylating agent such as dialkyl sulfates or alkyl sulfonates (e.g., tosylates, mesylates), or alkyl halides, preferably in the presence of a base (e.g., DIPEA, triethylamine, pyridine and the like). In Scheme 2(b), an amine is acylated when reacted with an activated carboxylic acid $R^{11}C(O)X$, such as an acid halide, anhydride, N-hydroxysuccinimide ester, or a carboxylic acid activated by a coupling agent (see Scheme 1) in the presence of a base like DIPEA, and optional use of a catalyst, such as DMAP or HOBt.

Scheme 2 is used to prepare, for example, Compounds 2 to 14, 19, 26 and 27 from Compound 1; and to produce N-alkylated and N-acylated derivatives, or any of the Compounds of Formula I comprising an N-alkyl or N-acyl group.

Prodrugs are prepared by routine chemical modifications such as described in Jerry March, supra, including esterification (Scheme 1) and alkylation reactions, i.e., use of activated acids or mixed anhydrides (acyl halides, use of coupling reagents, etc), and by the use of alkylating agents (R—X, wherein X is a leaving group, such as diazo, and R is the desired group). Phosphate prodrugs are prepared by phosphorylation, for example, with dialkyl phosphites using procedure such as described in Silverberg et al. (1996), *Tet. Lett.*, Vol. 37, 711-774, U.S. Pat. No. 5,561,122 (Pettit et al) and in Hwang and Cole (2004), *Org. Lett.*, vol 6, no 10, 1555-1556 ((POM)$_2$phosphate triester from (POM)$_2$phosphoryl chloride), the content of which is incorporated herein by reference in their entirety.

IV. Pharmaceutical Compositions Comprising the Compounds of the Invention

The invention provides a pharmaceutical composition comprising a therapeutically effective amount of a compound of the invention, or a pharmaceutically acceptable salt, solvate or prodrug thereof, in combination with a pharmaceutically acceptable carrier. The pharmaceutical composition comprising a cyclic hexadepsipeptide is useful for treating diseases and disorders associated with uncontrolled cellular growth and proliferation, such as a neoplastic condition. The pharmaceutical composition is also useful as antibacterial agent, and for treating bacterial infections. The pharmaceutical composition comprising a cyclic hexadepsipeptide may be packaged into a convenient commercial package providing the necessary materials, such as the pharmaceutical composition and written instructions for its use in treating a neoplastic condition or bacterial infection, in a suitable container.

The compounds of the present invention, or pharmaceutically acceptable salts, solvates or prodrugs thereof, can be formulated for oral, sublingual, intranasal, intraocular, rectal, transdermal, mucosal, topical or parenteral administration for the therapeutic or prophylactic treatment of neoplastic and proliferative diseases and disorders. Parenteral modes of administration include without limitation, intradermal, subcutaneous (s.c., s.q., sub-Q, Hypo), intramuscular (i.m.), intravenous (i.v.), intraperitoneal (i.p.), intra-arterial, intramedulary, intracardiac, intra-articular (joint), intrasynovial (joint fluid area), intracerebral or intracranial, intraspinal, intracisternal, and intrathecal (spinal fluids). Any known device useful for parenteral injection or infusion of drug formulations can be used to effect such administration. For oral and/or parental administration, compounds of the present invention can be mixed with conventional pharmaceutical carriers and excipients and used in the form of solutions, emulsions, tablets, capsules, soft gels, elixirs, suspensions, syrups, wafers and the like. The compositions comprising a compound of the present invention will contain from about 0.1% to about 99.9%, about 1% to about 98%, about 5% to about 95%, about 10% to about 80% or about 15% to about 60% by weight of the active compound.

The pharmaceutical preparations disclosed herein are prepared in accordance with standard procedures and are administered at dosages that are selected to reduce, prevent, or eliminate cancer. (See, e.g., *Remington's Pharmaceutical Sciences*, Mack Publishing Company, Easton, Pa.; and Goodman and Gilman, *Pharmaceutical Basis of Therapeutics*, Pergamon Press, New York, N.Y., the contents of which are incorporated herein by reference, for a general description of the methods for administering various agents for human therapy).

As used herein, the term "unit dosage" refers to physically discrete units suitable as unitary dosages for human subjects and other mammals, each unit containing a predetermined quantity of cyclic hexadepsipeptide calculated to produce the desired therapeutic effect, in association with a suitable pharmaceutically acceptable carriers. In one embodiment, the unit dosage contains from 10 to 3000 mg of active ingredient. In another embodiment, the unit dosage contains 20 to 1000 mg of active ingredient. The compositions of the present invention can be delivered using controlled (e.g., capsules) or sustained release delivery systems (e.g., bioerodable matrices). Exemplary delayed release delivery systems for drug delivery that are suitable for administration of the compositions of the invention are described in U.S. Pat. No. 4,452,775 (issued to Kent), U.S. Pat. No. 5,039,660 (issued to Leonard), and U.S. Pat. No. 3,854,480 (issued to Zaffaroni), incorporated herein by reference in their entirety.

The pharmaceutically-acceptable compositions of the present invention comprise one or more compounds of the present invention in association with one or more non-toxic, pharmaceutically-acceptable carriers and/or diluents and/or adjuvants and/or excipients, collectively referred to herein as "carrier" materials, and if desired other active ingredients. Pharmaceutically acceptable carriers include, for example, solvents, vehicles or medium such as saline, buffered saline, dextrose, water, glycerol, ethanol, propylene glycol, polysorbate 80 (Tween-80™), poly(ethylene) glycol 300 and 400 (PEG 300 and 400), PEGylated castor oil (E.g. Cremophor EL), poloxamer 407 and 188, hydrophobic carriers, and combinations thereof. Hydrophobic carriers include, for example, fat emulsions, lipids, PEGylated phopholids, polymer matrices, biocompatible polymers, liposheres, vesicles, particles, and liposomes. The term specifically excludes cell culture medium.

Excipients or additives included in a formulation have different purposes depending, for example on the nature of the drug, and the mode of administration. Examples of generally used excipients include, without limitation: stabilizing agents, solubilizing agents and surfactants, buffers, antioxidants and preservatives, tonicity agents, bulking agents, lubricating agents, emulsifiers, suspending or viscosity agents, inert diluents, fillers, disintegrating agents, binding agents, wetting agents, lubricating agents, antibacterials, chelating agents, sweeteners, perfuming agents, flavouring agents, coloring agents, administration aids, and combinations thereof.

The compositions may contain common carriers and excipients, such as cornstarch or gelatin, lactose, sucrose, microcrystalline cellulose, kaolin, mannitol, dicalcium phosphate, sodium chloride and alginic acid. The compositions may contain croscarmellose sodium, sodium starch glycolate or alginic acid.

Formulations for parenteral administration can be in the form of aqueous or non-aqueous isotonic sterile injection solutions, suspensions or fat emulsions, comprising a compound of this invention, or a pharmaceutically acceptable salt or prodrug thereof. The parenteral form used for injection must be fluid to the extent that easy syringability exists. These solutions or suspensions can be prepared from sterile concentrated liquids, powders or granules. The compounds can be dissolved in a carrier such as a solvent or vehicle, for example, polyethylene glycol, propylene glycol, ethanol, corn oil, benzyl alcohol, glycofurol, N,N-dimethylacetamide, N-methylpyrrolidone, glycerine, saline, dextrose, water, glycerol, hydrophobic carriers, and combinations thereof.

Excipients used in parenteral preparations also include, without limitation, stabilizing agents (e.g. carbohydrates, amino acids and polysorbates), solubilizing agents (e.g. cetrimide, sodium docusate, glyceryl monooleate, polyvinylpyrolidone (PVP) and polyethylene glycol (PEG)) and surfactants (e.g. polysorbates, tocopherol PEG succinate, poloxamer and Cremophor™), buffers (e.g. acetates, citrates, phosphates, tartrates, lactates, succinates, amino acids and the like), antioxidants and preservatives (e.g. BHA, BHT, gentisic acids, vitamin E, ascorbic acid and sulfur containing agents such as sulfites, bisulfites, metabisulfites, thioglycerols, thioglycolates and the like), tonicity agents (for adjusting physiological compatibility), suspending or viscosity agents, antibacterials (e.g. thimersol, benzethonium chloride, benzalkonium chloride, phenol, cresol and chlorobutanol), chelating agents, and administration aids (e.g. local anesthetics, anti-inflammatory agents, anti-clotting agents, vaso-constrictors for prolongation and agents that increase tissue permeability), and combinations thereof.

Parenteral formulations using hydrophobic carriers include, for example, fat emulsions and formulations containing lipids, liposphéres, vesicles, particles and liposomes. Fat emulsions include in addition to the above-mentioned excipients, a lipid and an aqueous phase, and additives such as emulsifiers (e.g. phospholipids, poloxamers, polysorbates, and polyoxyethylene castor oil), and osmotic agents (e.g. sodium chloride, glycerol, sorbitol, xylitol and glucose). Liposomes include natural or derived phospholipids and optionally stabilizing agents such as cholesterol.

In another embodiment, the parenteral unit dosage form of the compound can be a ready-to-use solution of the compound in a suitable carrier in sterile, hermetically sealed ampoules or in sterile pre-loaded syringes. The suitable carrier optionally comprises any of the above-mentioned excipients.

Alternatively, the unit dosage of the compound of the present invention can be in a concentrated liquid, powder or granular form for ex tempore reconstitution in the appropriate pharmaceutically acceptable carrier at the time of delivery. In addition the above-mentioned excipients, powder forms optionally include bulking agents (e.g. mannitol, glycine, lactose, sucrose, trehalose, dextran, hydroxyethyl starch, ficoll and gelatin), and cryo or lyoprotectants.

For example, in intravenous (IV) use, a sterile formulation of the compound of formula I and optionally one or more additives, including solubilizers or surfactants, can be dissolved or suspended in any of the commonly used intravenous fluids and administered by infusion. Intravenous fluids include, without limitation, physiological saline, phosphate buffered saline, 5% glucose or dextrose, or Ringer's™ solution.

In another example, in intramuscular preparations, a sterile formulation of the compound of the present invention or suitable soluble salts or prodrugs forming the compound, can be dissolved and administered in a pharmaceutical diluent such as Water-for-Injection (WFI), physiological saline or 5% glucose or dextrose. A suitable insoluble form of the compound may be prepared and administered as a suspension in an aqueous base or a pharmaceutically acceptable oil base, e.g. an ester of a long chain fatty acid such as ethyl oleate.

For oral use, solid formulations such as tablets and capsules are particularly useful. Sustained released or enterically coated preparations may also be devised. For pediatric and geriatric applications, suspension, syrups and chewable tablets are especially suitable. For oral administration, the pharmaceutical compositions are in the form of, for example, tablets, capsules, suspensions or liquid syrups or elixirs, wafers and the like. For general oral administration, excipient or additives include, but are not limited to inert diluents, fillers, disintegrating agents, binding agents, wetting agents, lubricating agents, sweetening agents, flavoring agents, coloring agents and preservatives.

The oral pharmaceutical composition is preferably made in the form of a unit dosage containing a therapeutically-effective amount of the active ingredient. Examples of such dosage units are tablets and capsules. For therapeutic purposes, the tablets and capsules which can contain, in addition to the active ingredient, conventional carriers such as: inert diluents (e.g., sodium and calcium carbonate, sodium and calcium phosphate, and lactose), binding agents (e.g., acacia gum, starch, gelatin, sucrose, polyvinylpyrrolidone (Povidone), sorbitol, tragacanth gum, methylcellulose, sodium carboxymethylcellulose, hydroxypropyl methylcellulose, and ethylcellulose), fillers (e.g., calcium phosphate, glycine, lactose, maize-starch, sorbitol, or sucrose), lubricants or lubricating agents (e.g., magnesium stearate or other metallic stearates, stearic acid, polyethylene glycol, waxes, oils, silica and colloical silica, silicon fluid or talc), disintegrants or disintegrating agents (e.g., potato starch, corn starch and alginic acid), flavouring, coloring agents, or acceptable wetting agents. Carriers may also include coating excipients such as glyceryl monostearate or glyceryl distearate, to delay absorption in the gastrointestinal tract.

Oral liquid preparations, generally in the form of aqueous or oily solutions, suspensions, emulsions, syrups or elixirs, may contain conventional additives such as suspending agents, emulsifying agents, non-aqueous agents, preservatives, coloring agents and flavoring agents. Examples of additives for liquid preparations include acacia, almond oil, ethyl alcohol, fractionated coconut oil, gelatin, glucose syrup, glycerin, hydrogenated edible fats, lecithin, methyl cellulose, methyl or propyl para-hydroxybenzoate, propylene glycol, sorbitol, or sorbic acid.

For both liquid and solid oral preparations, flavoring agents such as peppermint, oil of wintergreen, cherry, grape, fruit flavoring or the like can also be used. It may also be desirable to add a coloring agent to make the dosage form more aesthetic in appearance or to help identify the product. For topical use the compounds of present invention can also be prepared in suitable forms to be applied to the skin, or mucus membranes of the nose and throat, and can take the form of creams, ointments, liquid sprays or inhalants, lozenges, or throat paints. Such topical formulations further can include chemical compounds such as dimethylsulfoxide (DMSO) to facilitate surface penetration of the active ingredient. For application to the eyes or ears, the compounds of the present invention can be presented in liquid or semi-liquid form formulated in hydrophobic or hydrophilic bases as ointments, creams, lotions, paints or powders. For rectal administration the compounds of the present invention can be administered in the form of suppositories admixed with conventional carriers such as cocoa butter, wax or other glyceride.

Since the compounds of this invention possess antibacterial properties, formulations comprising same may be used for therapeutic and non-therapeutic purposes in antiseptic and disinfectant formulations. One or more compound of this invention can be formulated as, for example, a foaming detergent or solution such as a soap, shampoo, shower gel or shaving cream, as a microemulsion or micellar solution, as a spray or in simple alcoholic solutions, creams or emulsions.

V. Method of Inhibiting Neoplastic Cell Growth

In one aspect, the invention relates to a method for inhibiting growth and/or proliferation of cancer cells in a mammal. In another aspect, the invention provides a method for treating neoplasms in a mammal. Mammals include ungulates (e.g. sheeps, goats, cows, horses, pigs), and non-ungulates, including rodents, felines, canines and primates (i.e. human and non-human primates). In a preferred embodiment, the mammal is a human.

The cyclic hexadepsipeptides of the present invention may bind to or interact with other cancer-associated proteins and polypeptides, including, without limitation, polypeptides encoded by oncogenes, polypeptides that induce angiogenesis, proteins involved in metastasizing and/or invasive processes, and proteases that regulate apoptosis and the cell cycle. Regardless of the mechanism of action, the cyclic hexadepsipeptides of the invention have been demonstrated to exhibit anti-cancer activity both in vitro and in vivo. Based on these discoveries, applicants have developed methods for treating neoplasms.

As used herein, the terms "neoplasm", "neoplastic disorder", "neoplasia" "cancer," "tumor" and "proliferative disorder" refer to cells having the capacity for autonomous growth, i.e., an abnormal state of condition characterized by rapidly proliferating cell growth which generally forms a distinct mass that show partial or total lack of structural organization and functional coordination with normal tissue. The terms are meant to encompass hematopoietic neoplasms (e.g. lymphomas or leukemias) as well as solid neoplasms (e.g. sarcomas or carcinomas), including all types of pre-cancerous and cancerous growths, or oncogenic processes, metastatic tissues or malignantly transformed cells, tissues, or organs, irrespective of histopathologic type or stage of invasiveness. Hematopoietic neoplasms are malignant tumors affecting hematopoietic structures (structures pertaining to the formation of blood cells) and components of the immune system, including leukemias (related to leukocytes (white blood cells) and their precursors in the blood and bone marrow) arising from myeloid, lymphoid or erythroid lineages, and lymphomas (relates to lymphocytes). Solid neoplasms include sarcomas, which are malignant neoplasms that originate from connective tissues such as muscle, cartilage, blood vessels, fibrous tissue, fat or bone. Solid neoplasms also include carcinomas, which are malignant neoplasms arising from epithelial structures (including external epithelia (e.g., skin and linings of the gastrointestinal tract, lungs, and cervix), and internal epithelia that line various glands (e.g., breast, pancreas, thyroid). Examples of neoplasms that are particularly susceptible to treatment by the methods of the invention include leukemia, and hepatocellular cancers, sarcoma, vascular endothelial cancers, breast carcers, central nervous system cancers (e.g. astrocytoma, gliosarcoma, neuroblastoma, oligodendroglioma and glioblastoma), prostate cancers, lung and bronchus cancers, larynx cancers, esophagus cancers, colon cancers, colorectal cancers, gastrointestinal cancers, melanomas, ovarian and endometrial cancer, renal and bladder cancer, liver cancer, endocrine cancer (e.g. thyroid), and pancreatic cancer.

The cyclic hexadepsipeptide is brought into contact with or introduced into a cancerous cell or tissue. In general, the methods of the invention for delivering the compositions of the invention in vivo utilize art-recognized protocols for delivering therapeutic agents with the only substantial procedural modification being the substitution of the cyclic hexadepsipeptide of the present invention for the therapeutic agent in the art-recognized protocols. The route by which the cyclic hexadepsipeptide is administered, as well as the formulation, carrier or vehicle will depend on the location as well as the type of the neoplasm. A wide variety of administration routes can be employed. The cyclic hexadepsipeptide may be administered by intravenous or intraperitoneal infusion or injection. For example, for a solid neoplasm that is accessible, the compound of the invention may be administered by injection directly into the neoplasm. For a hematopoietic neoplasm the compound may be administered intravenously or intravascularly. For neoplasms that are not easily accessible within the body, such as metastases or brain tumors, the compound may be administered in a manner such that it can be transported systemically through the body of the mammal and thereby reach the neoplasm and distant metastases for example intrathecally, intravenously or intramuscularly or orally. Alternatively, the compound can be administered directly to the tumor. The compound can also be administered subcutaneously, intraperitoneally, topically (for example for melanoma), rectally (for example colorectal neoplasm) vaginally (for example for cervical or vaginal neoplasm), nasally or by inhalation spray (for example for lung neoplasm).

The cyclic hexadepsipeptide is administered in an amount that is sufficient to inhibit the growth or proliferation of a neoplastic cell, or to treat a neoplastic disorder. The term "inhibition" refers to suppression, killing, stasis, or destruction of cancer cells. The inhibition of mammalian cancer cell growth according to this method can be monitored in several ways. Cancer cells grown in vitro can be treated with the compound and monitored for growth or death relative to the same cells cultured in the absence of the compound. A cessation of growth or a slowing of the growth rate (i.e., the doubling rate), e.g., by 50% or more at 100 micromolar, is indicative of cancer cell inhibition (see Anticancer Drug Development Guide: preclinical screening, clinical trials and approval; B. A. Teicher and P. A. Andrews, ed., 2004, Humana Press, Totowa, N.J.). Alternatively, cancer cell inhibition can be monitored by administering the compound to an animal model of the cancer of interest. Examples of experimental non-human animal cancer models are known in the art and described below and in the examples herein. A cessation of tumor growth (i.e., no further increase in size) or a reduction in tumor size (i.e., tumor volume by least a 58%) in animals treated with the compound relative to tumors in control animals not treated with the compound is indicative of significant tumor growth inhibition (see Anticancer Drug Development Guide: preclinical screening, clinical trials and approval; B. A. Teicher and P. A. Andrews, ed., 2004, Humana Press, Totowa, N.J.).

The term "treatment" refers to the application or administration of a cyclic hexadepsipeptide to a mammal, or application or administration of a cyclic hexadepsipeptide to an isolated tissue or cell line from a mammal, who has a neoplastic disorder, a symptom of a neoplastic disorder or a predisposition toward a neoplastic disorder, with the purpose to cure, heal, alleviate, relieve, alter, ameliorate, improve, or control the disorder, the symptoms of disorder, or the predisposition toward disorder. The term "treating" is defined as administering, to a mammal, an amount of a cyclic hexadepsipeptide sufficient to result in the prevention, reduction or elimination of neoplastic cells in a mammal ("therapeutically effective amount"). The therapeutically effective amount and timing of dosage will be determined on an individual basis and may be based, at least in part, on consideration of the age, body weight, sex, diet and general health of the recipient subject, on the nature and severity of the disease condition, and on previous treatments and other diseases present. Other factors also include the route and frequency of administration, the activity of the administered compound, the metabolic stability, length of action and excretion of the compound, drug combination, the tolerance of the recipient subject to the compound and the type of neoplasm or proliferative disorder. In one embodiment, a therapeutically effective amount of the compound is in the range of about 0.01 to about 300 mg/kg of body weight of the mammal. In yet another embodiment, the therapeutically effective amount is in the range of 10 to about 50 mg/kg body weight per day. The therapeutically effective doses of the above embodiments may also be expressed in milligrams per square meter (mg/$m^2$) in the case of a human patient. Conversion factors for different mammalian species may be found in: Freireich et al, Quantitative comparison of toxicity of anticancer agents in mouse, rat, dog, monkey and man, *Cancer Chemoth. Report*, 1966, 50(4): 219-244, incorporated herein by reference in its entirety. When special requirements may be needed (e.g. for children patients), the therapeutically effective doses described above may be outside the ranges stated herein. Such higher or lower doses are within the scope of the present invention.

To monitor the efficacy of tumor treatment in a subject, tumor size and/or tumor morphology is evaluated before and after initiation of the treatment, and treatment is considered effective if either the tumor size ceases further growth, or if the tumor is reduced in size, e.g., by at least 10% or more (e.g., 20%, 30%, 40%, 50%, 60%, 70%, 80%, 90% or even 100%, that is, the absence of the tumor). Prolongation of survival, time-to-disease progression, partial response and objective response rate are surrogate measures of clinical activity of the investigational agent. Tumor shrinkage is considered to be one treatment-specific response. This system is limited by the requirement that subjects have visceral masses that are amenable to accurate measurement. Methods of determining the size of a tumor in vivo vary with the type of tumor, and include, for example, various imaging techniques well known to those in the medical imaging or oncology fields (MRI, CAT, PET, etc.), as well as histological techniques and flow cytometry. For certain types of cancer, evaluation of serum tumor markers are also used to evaluate response (eg prostate-specific antigen (PSA) for prostate cancer, and carcino-embryonic antigen (CEA), for colon cancer). Other methods of monitoring cancer growth include cell counts (e.g. in leukemias) in blood or relief in bone pain (e.g. prostate cancer).

The cyclic hexadepsipeptide compound may be administered once daily, or the compound may be administered as two, three, four, or more sub-doses at appropriate intervals throughout the day. In that case, the cyclic hexadepsipeptide compound contained in each sub-dose must be correspondingly smaller in order to achieve the total daily dosage. The dosage unit can also be compounded for delivery over several days, e.g., using a conventional sustained release formulation which provides sustained release of the cyclic hexadepsipeptide compound over a several day period. Sustained release formulations are well known in the art. In this embodiment, the dosage unit contains a corresponding multiple of the daily dose. The effective dose can be administered either as a single administration event (e.g., a bolus injection) or as a slow injection or infusion, e.g. over 30 minutes to about 24 hours. The compound may be administered as a treatment, for up to 30 days. Moreover, treatment of a subject with a therapeutically effective amount of a composition can include a single treatment or a series of treatments (e.g., a four-week treatment repeated 3 times, with a 2 months interval between each treatment). Estimates of effective dosages, toxicities and in vivo half-lives for the cyclic hexadepsipeptide compounds encompassed by the invention can be made using conventional methodologies or on the basis of in vivo testing using an appropriate animal model.

The cyclic hexadepsipeptide compound may be administered in conjunction with or in addition to known other anti-cancer treatments such as radiotherapy, or other known anti-cancer compounds or chemotherapeutic agents. Such agents include, but are not limited to, 5-fluorouracil, mitomycin C, methotrexate, hydroxyurea, cyclophosphamide, dacarbazine, mitoxantrone, anthracyclines (Epirubicin and Doxurubicin), etopside, pregnasome, platinum compounds such as carboplatin and cisplatin, taxanes such as paclitaxel and docetaxel; hormone therapies such as tamoxifen and anti-estrogens; antibodies to receptors, such as herceptin and Iressa; aromatase inhibitors, progestational agents and LHRH analogues; biological response modifiers such as IL2 and interferons; multidrug reversing agents such as the cyclosporin analogue PSC 833.

Toxicity and therapeutic efficacy of cyclic hexadepsipeptide compounds can be determined by standard pharmaceutical procedures in cell cultures or experimental animals. Therapeutic efficacy is determined in animal models as described above and in the examples herein.

The data obtained from cell culture assays and animal studies can be used in formulating a range of dosage for use in humans. The dosage of compositions of the invention will generally be within a range of circulating concentrations that include the MTD. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range of the compound. Such information can be used to more accurately determine useful doses in humans. Levels in plasma may be measured, for example, by HPLC.

Animal models to determine antitumor efficacy of a compound are generally carried out in mice. Either murine tumor cells are inoculated subcutaneously into the hind flank of mice from the same species (syngeneic models) or human tumor cells are inoculated subcutaneously into the hind flank of severe combined immune deficient (SCID) mice or other immune deficient mice (nude mice) (xenograft models).

Advances in mouse genetics have generated a number of mouse models for the study of various human diseases including cancer. The MMHCC (Mouse models of Human Cancer Consortium) web page (emice.nci.nih.gov), sponsored by the National Cancer Institute, provides disease-site-specific compendium of known cancer models, and has links to the searchable Cancer Models Database (cancermodels.nci.nih.gov), as well as the NCI-MMHCC mouse repository. Mouse repositories can also be found at: The Jackson Laboratory, Charles River Laboratories, Taconic, Harlan, Mutant Mouse Regional Resource Centers (MMRRC) National Network and at the European Mouse Mutant Archive. Such models may be used for in vivo testing of cyclic hexadepsipeptide compounds, as well as for determining a therapeutically effective dose.

VI. Method of Inhibiting Bacterial or Fungal Growth

As described herein, the compounds of this invention possess antibacterial and/or antifungal activity. The compounds of this invention can thus be used as antibacterial or antifungal agents, for the suppression of bacterial or fungal infections, as topical antibacterial agents or as general disinfectants. Any of the pharmaceutical compositions described in the above Section IV, are used in the applications described in this section.

According to another embodiment, the invention provides a method of decreasing bacterial or fungal quantity in a biological sample. This method comprises the step of contacting the biological sample with a cyclic hexadepsipeptide of Formula I, or a pharmaceutically acceptable salt or prodrug thereof. This method is effective if the number of fungus or bacteria decreases by at least 10%, and preferably more, e.g., 25%, 50%, 75% or even 100% after contacting the biological sample with a cyclic hexadepsipeptide of Formula I, a compound as described herein, or a pharmaceutically acceptable salt or prodrug thereof.

These pharmaceutical compositions effective to treat or prevent a bacterial or fungal infection, which comprise any one of Compound 1, a compound of Formula I as described herein, or a pharmaceutically acceptable salt or prodrug thereof in an amount sufficient to measurably decrease bacterial or fungal quantity, and a pharmaceutically acceptable carrier, are another embodiment of the present invention. The term "measurably decrease bacterial or fungal quantity", as used herein means a measurable change in the number of bacteria between a treated sample and an untreated sample.

This invention provides a method of treating a bacterial infection in a mammal in need thereof, but further comprising the step of administering to the mammal an agent which increases the susceptibility of bacterial organisms to antibiotics. Agents which increase the susceptibility of bacterial organisms to antibiotics are known. For example, U.S. Pat. Nos. 5,523,288, 5,783,561 and 6,140,306 describe methods of using bactericidal/permeability-increasing protein (BPI) for increasing antibiotic susceptibility of gram-positive and gram-negative bacteria. Agents that increase the permeability of the outer membrane of bacterial organisms have been described by Vaara, M. (1992) in *Microbiological Reviews*, 395-411, and the sensitization of gram-negative bacteria has been described by Tsubery, H., et al. (2000), in *J. Med. Chem.*, 3085-3092.

For the method of the invention related to treatment of subjects with a bacterial or fungal infection, a typical effective unit dose of a cyclic hexadepsipeptide as described herein or a pharmaceutically acceptable salt or prodrug thereof given orally or parenterally would be from about 0.01 to about 100 mg/kg of body weight of the subject with a daily dose ranging from about 0.01 to about 300 mg/kg of body weight of the subject. A typical daily dose for an adult human is from about 50 mg to about 1.0 g. A recipient subject refers to a warm-blooded animal such as mammals, including ungulates (e.g. sheeps, goats, cows, horses, pigs), and non-ungulates, including rodents, felines, canines and primates (i.e. human and non-human primates).

Methods of decreasing bacterial quantity are effective if the number of bacteria decreases at least 10%, and preferably more, e.g., 25%, 50%, 75% or even 100% after contacting the biological sample cyclic hexadepsipeptide as described herein, or a pharmaceutically acceptable derivative, salt or prodrug thereof.

The pharmaceutical compositions and methods of this invention will be useful generally for controlling bacterial infections in vivo. Examples of bacterial organisms that may be controlled by the compositions and methods of this invention include, but are not limited to the following organisms: *Streptococcus* sp. (including *S. pneumoniae*), *Enterococcus* sp. (including *E. faecalis* and *E. faecium*), *Staphylococcus* sp. (including *S. aureus* and *S. epidermidis*), *Bacillus* sp. (including *B. subtilis*), *Micrococcus luteus*, *Clostridium* sp. (including *C. difficile* and *C. perfringens*), and *Corynebacterium* sp. (including *C. diphtheriae*). The compositions and methods will therefore be useful for controlling, treating or reducing the advancement, severity or effects of nosocomial or non-nosocomial infections. Examples of nosocomial uses include, but are not limited to, urinary tract infections, pneumonia, surgical wound infections, infections with *C. difficile*, bacteremia and therapy for febrile neutropenic patients. Examples of non-nosocomial uses include but are not limited to urinary tract infections, pneumonia, prostatitis, skin and soft tissue infections and intra-abdominal infections.

Since the compounds of this invention possess antibacterial and antifungal properties, formulations comprising same may be used for therapeutic and non-therapeutic purposes in antiseptic and disinfectant formulations. Foaming detergents and solutions are used by nursing staff and surgeons for washing their hands, or used for cleaning dermatological lesions such as impetigo, pityriasis, and leg ulcers. Foaming detergents are used to prepare soaps, shampoos (e.g. antidandruff), shower gels or shaving creams. Sprays and solutions are used as antiseptics for postoperative treatments, for the treatment of infections, burns, eczema, gluteal erythema, wounds, or acne, or for deodorants. The compounds are also used in combination with agents that help active ingredients to penetrate the keratinized layers of skin and superficial body growths. Such agents are, for example, Azone (Nelson Research) and Transcutol (Gattefosse). Antiseptic solutions containing such agents are used, for example, on skin before puncture, for the preparation of operative field, as hand antiseptic by nursing staff, or for treating closed infected dermatosis, folliculitis, perionychia or acne. The compounds of this invention are also used as surface disinfectants, especially for use in the medical or veterinary sectors. These surface disinfectants may be in the form of aqueous or non-aqueous foaming detergent, sprays or nebulizers.

Treatment of bacterial infection in a subject, including mammals and humans, may be accomplished by administering a compound of the invention as a single agent, or in combination with other known antibacterial agents. Antibacterial families include, for example, antibiotics (e.g. aminoglycosides, amphenicols, ansamycins, β-lactams, lincosamides, macrolides, polypeptides, tetracyclines, and the like), and synthetic antibacterials (e.g. 2,4-diaminopyrimidines, nitrofurans, quinolones and analogs, sulfonamides, sulfones, and the like), optionally within liposomal formulations. (For more examples, see: *The Merck Index*, 12$^{th}$ edition (1996), Therapeutic Category and Biological Activity Index, lists under "Antibacterial" sections; or the same sections of the more recent version: *The Merck Index*, 13$^{th}$ edition (2001), both incorporated by reference in their entirety). Such agents may be administered together with or separately from the compounds of this invention. In addition, certain patients may suffer from or may be susceptible to simultaneous infections from bacteria and one or more viruses. Those patients may benefit from simultaneous or separate co-administration of a compound or formulation according to this invention and an anti-viral agent, for example, without limitation, an anti-influenza medication such as Relenza™ (zanamivir) and Tamiflu™ (oseltamivir) or an anti-enteric virus drug such as pleconaril. Additional combination therapies may also include a compound of this invention and an anti-fungal agent, such as Cancidas™ (caspofungin acetate), Diflucan™ (fluconazole), and Mycostatin™ (nystatin). Clearly, the combination therapies described herein are merely exemplary and are not meant to limit possibilities for other combination treatments or co-administration regimens.

In addition to the compounds of the invention, pharmaceutically acceptable salts, solvates or prodrugs of said compounds may also be employed in compositions to treat or prevent the above-identified disorders.

EXAMPLES

Unless otherwise noted, all reagents were purchased from Sigma Chemical Co. (St. Louis, Mo.), Aldrich.

All NMR spectra were collected in deuterated solvent on a Varian Unity Inova 500™ Spectrometer ($^1$H NMR at 500 MHz, $^{13}$C NMR at 125 MHz), referenced to TMS. UV and mass spectra were collected by Waters 2690™ HPLC using a photodiode array detector (PDA, 210-400 nm) coupled to a Waters Micromass™ ZQ™ mass detector.

Unless otherwise indicated, all numbers expressing quantities of ingredients, properties such as molecular weight, reaction conditions, molar equivalents (eq), $GI_{50}$, MIC and so forth used in the specification and claims are to be understood as being modified in all instances by the term "about". Accordingly, unless indicated to the contrary, the numerical parameters set forth in the present specification and attached claims are approximations. At the very least, and not as an attempt to limit the application of the doctrine of equivalents to the scope of the claims, each numerical parameter should at least be construed in light of the number of significant figures and by applying ordinary rounding techniques. Notwithstanding that the numerical ranges and parameters setting forth the broad scope of the invention are approximations, the numerical values set in the examples, Tables and Figures are reported as precisely as possible. Any numerical values may inherently contain certain errors resulting from variations in experiments, testing measurements, statistical analyses and such.

In addition, the materials, methods, and examples, including in vitro and in vivo efficacy, and toxicity are illustrative only and not intended to be limiting. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control.

Example 1

Production of Compound 1 by Fermentation

*Streptomyces* sp. Eco180 was isolated from a soil sample. The producing organism is cultivated under aerobic conditions in an aqueous nutrient medium containing assimilable sources of carbon, assimilable sources of nitrogen, inorganic salts and vitamins. Thus, for instance, preferred carbon sources are glucose, potato dextrin, cane molasses, sucrose and the like. Preferred nitrogen sources are N-Z Amine A, yeast extract, Soytone peptone, and the like. Certain media are preferred for production of Compound 1. This strain is preferably grown at temperatures of about 28° C. to 30° C.

*Streptomyces* sp. Eco180 (deposit accession number IDAC 220905-01) was maintained and sporulated on agar plates of ISP2 or ISP4 media (Difco Laboratories, Detroit, Mich.). An inoculum for the production phase was prepared by adding two loopfull of the spores obtained from the surface of the ISP2 agar plate to a 125-ml flask containing 25 ml of ITSB medium composed of: 30 g trypticase soy broth (Bacto), 3 g yeast extract, 2 g $MgSO_4$, 5 g glucose, 4 g maltose, made up to one liter with distilled water. The culture was incubated at about 28° C. for approximately 60 hours on a rotary shaker set at 250 rpm. Following incubation, 10 ml of culture was transferred to 2 L baffled flasks each containing ten glass beads and 500 ml of sterile production medium FA (see Table 1). The medium was adjusted at pH 7.0 before sterilization. The fermentation batches were incubated aerobically under stirring (250 rpm, 2.5 cm throw) at 28° C. for a period of 4 to 7 days.

Compound 1 is produced in other media, such as in table 1, and including media KH and VB.

Example 2

Isolation of Compound 1

The pooled culture broth (500 mL×12) was treated with ethyl acetate (EtOAc, 3.6 L), shaken for 30 minutes and centrifuged at 3000 rpm for 20 minutes. The organic layer was separated, dried over anhydrous magnesium sulfate ($MgSO_4$), filtered and the filtrate was evaporated under reduced pressure leading to a viscous EtOAc extract. The extract was dissolved in methanol (MeOH, 200 mL) and centrifuged at 300 rpm for 10 minutes. The supernatant was drawn off, coated onto Diaion™ HP-20 resin (25 mL; Supelco, USA) and the coated HP-20 resin was used as a solid phase charge for a Strata™ C18-E (5 mm, 70 A, 10 g; Phenomenex) column eluted with a MeOH/water step-wise gradient leading to six 100 mL fractions: MeOH/water (20:80), MeOH/water (40:60), MeOH/water (60:40), MeOH/water (80:20), MeOH and MeOH with 0.1% trifluoroacetic acid. The MeOH fraction was concentrated to approximately 10 mL and the concentrate was subjected to chromatography on a Sephadex™ LH-20 column (100×3.5 cm; Amersham Biosciences, Sweden) eluted with MeOH (10 min/fraction) (15 mL). Fractions 24-26 were pooled and concentrated to provide pure Compound 1 (582.1 mg) as a colorless amorphous powder.

Example 3

Elucidation of the Structure of Compound 1

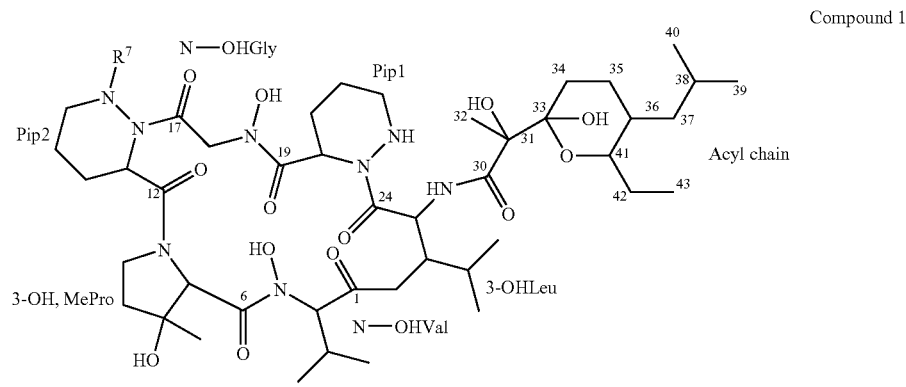

Compound 1 wherein N—OHVal is N-hydroxyvaline; 3-OH,MePro is 3-hydroxy-3-methylproline; Pip is piperazic acid; N—OHGly is N-hydroxyglycine, and the acyl chain is a 2-(6-ethyl-2-hydroxy-5-isobutyl-tetrahydropyran-2-yl)-2-hydroxypropionyl.

The calculated molecular weight of the major isotope (924.52) and formula ($C_{43}H_{72}N_8O_{14}$) of Compound 1 was confirmed by mass spectral analysis: negative ionization gave an $(M-H)^-$ molecular ion of 923.7 and a fragment $(M-H-H_2O)^-$ having a mass of 905.6, and positive ionization gave a fragment $(M+H-H_2O)^+$ having a mass of 907.7 and a fragment $(M+H-2H_2O)^+$ having a mass of 889.7.

Proton and carbon NMR spectral analysis is shown in Table 2. NMR data were collected dissolved in chloroform-D (CDCl$_3$) including proton, carbon and multidimensional pulse sequences gCOSY, gHSQC, gHMBC, and NOESY.

TABLE 2

$^1$H and $^{13}$C NMR ($\delta_H$, ppm) Data of Compound 1 in CDCl$_3$

| No. | Position | $^1$H | $^{13}$C | Group |
|---|---|---|---|---|
| 1 | N-OHVal CO | — | 169.9 | C(O) |
| 2 | α | 5.23 | 62.7 | CH |
| 3 | β | 2.49 | 29.7 | CH |
| 4 | γ | 1.07 | 19.8 | CH$_3$ |
| 5 | γ' | 1.08 | 20.0 | CH$_3$ |
|  | N-OH | 8.29$^a$ | — | OH |
| 6 | 3-OH,MePro CO | — | 166.5 | C(O) |
| 7 | α | 4.82 | 67.7 | CH |
| 8 | β | — | 78.9 | C |
| 9 | β-CH$_3$ | 1.48 | 27.6 | CH$_3$ |
| 10 | γ | 2.39, 1.85 | 37.9 | CH$_2$ |
| 11 | δ | 4.73, 3.21 | 45.5 | CH$_2$ |
|  | β-OH | 5.72$^a$ | — | OH |
| 12 | Pip2 CO | — | 170.4 | C(O) |
| 13 | α | 5.28 | 47.2 | CH |
| 14 | β | 1.98, 1.40 | 23.7 | CH$_2$ |
| 15 | γ | 2.42, 1.40 | 19.6 | CH$_2$ |
| 16 | δ | 3.13, 2.80 | 47.6 | CH$_2$ |
|  | δ-NH | 4.19 | — | NH |
| 17 | N-OHGly CO | — | 176.4 | C(O) |
| 18 | α | 5.81, 3.69 | 47.3 | CH$_2$ |
|  | N-OH | 10.23$^a$ | — | OH |
| 19 | Pip1 CO | — | 169.6 | C(O) |
| 20 | α | 5.09 | 50.5 | CH |
| 21 | β | 2.32, 1.79 | 25.3 | CH$_2$ |
| 22 | γ | 1.61 | 21.1 | CH$_2$ |
| 23 | δ | 3.15, 2.86 | 46.8 | CH$_2$ |
|  | δ-NH | 4.93 | — | NH |
| 24 | 3-OHLeu CO | — | 171.7 | C(O) |
| 25 | α | 4.90 | 56.1 | CH |
| 26 | β | 5.42 | 77.3 | CH |
| 27 | γ | 1.93 | 29.5 | CH |
| 28 | δ | 0.93 | 20.2 | CH$_3$ |
| 29 | δ' | 0.91 | 24.5 | CH$_3$ |
|  | NH | 8.36 | — | NH |
| 30 | Acyl chain CO | — | 177.6 | C(O) |
| 31 | α | — | 77.0 | C |
| 32 | α-CH$_3$ | 1.39 | 20.6 | CH$_3$ |
| 33 | β | — | 99.3 | C |
| 34 | γ | 1.75, 1.69 | 28.1 | CH$_2$ |
| 35 | δ | 1.78, 1.45 | 24.5 | CH$_2$ |
| 36 | ε | 1.27 | 36.3 | CH |
| 37 | ζ | 1.09, 0.95 | 40.9 | CH$_2$ |
| 38 | η | 1.67 | 24.9 | CH |
| 39 | η-CH$_3$ | 0.85 | 21.7 | CH$_3$ |
| 40 | θ | 0.91 | 24.5 | CH$_3$ |
| 41 | ζ' | 3.62 | 76.0 | CH |
| 42 | η' | 1.57, 1.42 | 25.2 | CH$_2$ |
| 43 | θ' | 0.81 | 9.0 | CH$_3$ |
|  | α-OH | 3.05 | — | OH |
|  | β-OH | 6.56 | — | OH |

$^a$These chemical shifts may be exchangeable

Based on the mass, UV and NMR spectroscopy data, the structure of the compound was determined to be the structure of Compound 1 shown above.

Example 4

In Vitro Antimicrobial Activity of Compound 1

A) Antibacterial Activity of Compound 1

Antibacterial activity of Compound 1 (Table 3) was measured by determining the minimal inhibitory concentration (MIC) necessary to obtain a complete inhibition of bacteria growth in twelve indicator strains, namely species of *Staphylococcus aureus* (methicilline resistant and sensitive species), *Staphylococcus epidermidis*, *Enterococcus faecalis* (vancomycin resistant and sensitive species), *Streptococcus pneumoniae* (penicillin resistant and sensitive species), *Bacillus subtilis*, *Micrococcus luteus*, *Corynebacterium diphtheriae* and *Clostridium* sp (difficile and perfringens). Indicator strains preparation and MIC determination were performed according to the National Committee for Clinical Laboratory Standards (NCCLS) guideline M7-A5 *Methods for Dilution Antimicrobial Susceptibility Tests for Bacteria That Grow Aerobically; Approved Standard-Fifth Edition*. (NCCLS document M7-A5, ISBN 1-56238-394-9; NCCLS, 940 West Valley Road, Suite 1400, Wayne, Pa. 19087-1898 USA), the content of which is incorporated herein by reference. MIC determination against *C. difficile* was performed according to National Committee for Clinical Laboratory Standards (NCCLS) guideline M11-A5 Methods for Antimicrobial Susceptibility Testing of Anaerobic Bacteria.

Compound 1 was prepared as 100× stock solutions in DMSO, with concentrations ranging from 3.2 mg/mL to 0.003 mg/mL (a two-fold dilution series over 11 points). An aliquot of each 100× stock solution was diluted 50-fold in test medium described below to give a set of eleven (11) 2× solutions. 50 μL of each of the eleven 2× solutions was aliquoted into the corresponding well of a 12-well row, with the final well reserved for medium alone control.

Vancomycin (Sigma™), used as positive control compound, was prepared as 2× stock solutions in Mueller-Hinton test medium ranging from 64 μg/mL to 0.06 μg/ml (a two-fold dilution series over 11 points). An aliquot of 50 μL corresponding to each concentration (at 2×) was then transferred to 96-well microplates to obtain a series of eleven two-fold dilutions.

An isolated colony of each of the indicator strains was used to inoculate tubes containing 2 mL of test medium. MH (Mueller-Hinton) test medium was used for *Staphylococcus* sp., *Micrococcus luteus*, and *Corynebacterium diphtheriae* indicator strains. BHI+ (Brain Heart Infusion broth supplemented with 5 mM CaCl$_2$) test medium was used for *Enterococcus faecalis*, and *Bacillus subtilis* indicator strains. MH test medium (+2% lysed horse blood) was used for *Streptococcus pneumoniae* indicator strains. *Brucella* medium supplemented with hemin, vitamin K1 and 5% lysed horse blood was used for *Clostridium* sp. Inoculum density for each indicator strain was adjusted to OD$_{600}$=0.1 in 5 ml 0.85% saline, then further diluted 1/100 in appropriate medium. 50 μL of the final dilution (in test medium) of each indicator strain was added to each well of a 12-well row. This brings the final dilution of the test article or control compound in solution to 1×. The final inoculum was approximately $5 \times 10^5$ CFU/mL.

The indicator strains were incubated with 11 concentrations of each of Compound 1, Vancomycin (Sigma™) control compound and one media alone control. For MIC determination, assay plates were incubated at 35° C. for 16 to 20 hours. The MIC for each indicator was assessed as the lowest concentration of compound resulting in total absence of growth and is shown below.

TABLE 3

In vitro Antimicrobial Activities (MIC, µg/mL)

| | Source | Resistance Phenotype | Compound 1 | Vancomycin |
|---|---|---|---|---|
| S. aureus | ATCC ™ 6538P | MSSA | 0.031 | 1 |
| S. aureus MRS3 | ATCC ™ 700699 | MRSA-hVISA | 0.50 | 4 |
| S. epidermidis | ATCC ™ 12228 | — | 0.094 | 2 |
| Enterococcus faecalis | ATCC ™ 29212 | VSE | 0.50 | 4 |
| Enterococcus faecalis | ATCC ™ 51299 | VRE | 1.0 | 32 |
| S. pneumoniae | LSPQ 3412[a] | Penicillin sensitive | 0.156 | 0.25 |
| S. pneumoniae | LSPQ 3349[a] | Penicillin resistant | 0.031 | 0.5 |
| C. difficile | ATCC ™ 9689 | — | <0.008 | 0.25 |
| C. perfringens | HER1390[b] | — | <0.008 | 0.5 |
| C. diphtheriae | HER1356[c] | — | <0.008 | 0.5 |
| B. subtilis | ATCC ™ 23857 | — | 0.004 | 0.25 |
| M. Luteus | ATCC ™ 9341 | — | 0.063 | 2 |

[a]LSPQ: Clinical isolate provided by "Laboratoire de Santé Publique du Québec".
[b]strain WS2895, provided by the "Département de biochimie et de microbiologie, Faculté des sciences et de génie, Université Laval, Québec, Canada"
[c]strain C7, same source as b.

Compound 1, as shown in Table 3, proved to be a very potent antibacterial agent against a wide variety of bacterial strains, including resistant strains. Compound 1 also exhibited very potent antibacterial activity against *C. diphtheriae* and *Clostridium* species.

B) Antifungal Activity of Compound 1

Testing of antifungal activity was performed according to NCCLS method (NCCLS. *Reference Method for Broth Dilution Antifungal Susceptibility Testing of Yeasts; Approved Standard*. NCCLS document M27-A (ISBN 1-56238-328-0). NCCLS, 940 West Valley Road, Suite 1400, Wayne, Pa. 19087-1898 USA). Compound 1 was prepared as 100× stock solutions in DMSO, with concentrations ranging from 3.2 mg/mL to 0.003 mg/mL (a two-fold dilution series over 11 points). An aliquot of each 100× stock solution was diluted 50-fold in test medium described below to give a set of eleven (11) 2× solutions. 50 µL of each of the eleven 2× solutions was aliquoted into the corresponding well of a 12-well row, with the final well reserved for medium alone control. Inoculum density for the *Candida albicans* ATCC™10231 indicator strain was adjusted to $OD_{600}$=0.1 in 5 mL 0.85% saline, then further diluted 1/1000 in RPMI 1640 medium. 50 µL of the final dilution (in test medium) of each indicator strain was added to each well of a 12-well row. This brings the final dilution of the test article or control compound in solution to 1×. The final inoculum was approximately $5 \times 10^4$ CFU/ml.

Compound 1 exhibited antifungal activity (MIC: 8 µg/mL after 48 hours) against *Candida albicans* ATCC™10231.

Example 5

IN Vitro Cytotoxic Activity Compound 1

In vitro Anticancer Activity of Compound 1 Against Four Cell Lines:

Compound 1 was tested in four cell lines: HT-29 (colorectal carcinoma), SF268 (CNS), MDA-MB-231 (mammary gland adenocarcinoma), PC-3 (prostate adenocarcinoma), and in HUVEC (human umbilical vein endothelial cells). In vitro cytotoxic activity are expressed in Table 4 as $GI_{50}$ values in nM. Procedure used for the test is described below.

TABLE 4

In vitro Cytotoxic Activities ($GI_{50}$, nM)

| Cell line | Source | Compound 1 | Daunorubicin |
|---|---|---|---|
| SF-268 | NCI-DCTD | 25 | 19 |
| HT-29 | NCI-DCTD | 37 | 20 |
| MDA-MB-231 | NCI-DCTD | 28 | 9 |
| PC-3 | NCI-DCTD | 66 | 11 |
| HUVEC | BD-Biosciences | 19 | N/T |

N/T: not tested

In vitro cytotoxic activities ($GI_{50}$) of Compound 1 were determined using propidium iodide (PI) as being the concentration of drug resulting in 50% growth inhibition, and by using the following method.

Two 96-well plates were seeded in duplicate with each cell line at the appropriate inoculation density (SF268: 3,000; HT29: 3,000; MDA-MB-231: 7,500; PC-3: 3,000; and HUVEC: 6,000 cells) and according to the technical data sheet of each cell line (rows A-G, 75 µL of media per well). Row H was filled with medium only (150 µL, negative control-medium). The plates were incubated at appropriate temperature and $CO_2$ concentration for 24 hrs.

Test compound and control were prepared as 15× stock solutions in appropriate medium and corresponding to 450, 45, 0.45, 0.045, and 0.0045 µM (prepared the day of the experiment). An aliquot of each was diluted 7.5-fold in appropriate test medium to give a set of six 2× concentration solutions (60, 6, 0.6, 0.06, 0.006, and 0.0006 µM). A 75 µL aliquot of each concentration was added to each corresponding well (rows A to F) of the second plate. Row G was filled with 75 µL of medium/0.6% DMSO (negative control-cells). The second plate was incubated at appropriate temperature and $CO_2$ concentration for 96 hrs, except for HUVEC, which was incubated for 72 hours.

First Plate: PI (30 µL, 50 µg/mL) was added to each well of the first plate without removing the culture medium. The plate was centrifuged (Sorvall Legend-RT, swinging bucket) at 3500 rpm/10 min. Fluorescence intensity (Thermo, Varioskan, $\lambda_{ex}$: 530 nm; $\lambda_{em}$: 620 nm) was measured to give the first measurement, dead cells (DC at $T_0$; before freezing). Two round of Freeze (−80° C.)/Thaw (37° C.) were done. Fluorescence intensity was determined to give the second measure, total cells (TC at $T_0$; after freeze/thaw)

Second plate was processed as the first one, except there were three rounds of freeze/thaw instead of two. First measurement gave the treated dead cells value (TDC), and the second measurement gave the treated total cells value (TTC). Both values were collected for each treated well and control (CTC and CDC).

Each value (DC, TC, TDC, TTC, CTC and CDC) was corrected by removing the background value (medium only) to give the value ($FU_{DC(T=0)}$, $FU_{TC(T=0)}$, $FU_{TDC}$, $FU_{TTC}$, $FU_{CTC}$ and $FU_{CDC}$) used in the calculation of the T/C (%) (Treated/Control) for each concentration. T/C (%) for each concentration is calculated using the following formula:

$$T/C(\%) = \frac{(FU_{TTC} - FU_{TDC}) - (FU_{TC(T=0)} - FU_{DC(T=0)}) \times 100}{(FU_{CTC} - FU_{CDC}) - (FU_{TC(T=0)} - FU_{DC(T=0)})}$$

The $GI_{50}$ value emphasizes the correction for the cell count at time zero for cell survival, which reflects the difference in growth kinetics. The T/C values are transposed in a graph to determine $GI_{50}$ values, the concentration at with the T/C is 50%.

Example 6

In Vivo Anti-Cancer Efficacy of Compound 1

In vivo efficacy of Compound 1 in a human breast cancer xenograft model:

The antitumor activity of Compound 1 was tested in vivo in a human MX-1 breast carcinoma model in mice, formulated in 10% ethanol, 7.5% ethanolic polysorbate 80 (1 g/mL in ethanol), and 82.5% saline. Harlan female athymic nude mice (12 weeks of age on Day 1 (D1)) were used for this study. Human MX-1 carcinoma was maintained in athymic nude mice by serial engraftment. A tumor fragment (1 mm$^3$) was implanted subcutaneously into the right flank of each test mouse. Tumors were monitored twice weekly and then daily as their mean volume approached 80-120 mm$^3$.

On D1, animals were sorted into treatment groups 1 to 4 (groups 1 to 3: 9 mice; group 4:10 mice), with tumor sizes of 63-144 mm$^3$ and group mean tumor sizes of about 99 mm$^3$. Tumor volumes were calculated as (width$^2$×length) divided by 2. Tumor weight was estimated with the assumption that 1 mg is equivalent to 1 mm$^3$ of tumor volume.

Starting on Day 1, each group was treated with dosing volumes of 0.2 mL/20-g mouse in Groups 1 and 2, and 0.1 mL/20-g mouse for Groups 3 and 4, scaled to the body weight of each animal, and according to the following protocol:

TABLE 5

Dosing Schedules of Groups 1 to 4

| Group | Agent | Vehicle | mg/kg | Route | Schedule |
|---|---|---|---|---|---|
| 1 | D5W | — | — | i.p. | qod × 7 |
| 2 | Cyclophosphamide[a] | Saline | 90 | i.p. | qd × 5 |
| 3 | Vehicle[b] | — | — | i.p. | qod × 5, then q4d × 7 |
| 4 | Compound 1 | Vehicle[b] | 1 | i.p. | D1, 3, 5, 9, then q4d × 7 starting on D15 |

[a]Cyclophosphamide: Neosar ®, 2 mg/mL, Pharmacia
[b]Vehicle: 10% ethanol, 7.5% polysorbate 80 in saline Tumor measurements were taken twice weekly using calipers and were converted to tumor weight. Tumor weight was estimated with the assumption that 1 mg is equivalent to 1 mm$^3$ of tumor volume (tumor volume was determined as above). Body weights were also recorded daily for Day 1 to 5, and then twice weekly.

Endpoint:

Each animal was euthanized when its neoplasm reached the predetermined endpoint size (1,500 mm$^3$). The "time to endpoint" (TTE) for each mouse was calculated by the following equation:

$$TTE = \frac{\log_{10}(\text{endpoint volume}) - b}{m}$$

where "TTE" is expressed in days, "endpoint volume" is in mm$^3$, "b" is the intercept, and "m" is the slope of the line obtained by linear regression of a log-transformed tumor growth data set. The data set comprised the first observation that exceeded the study endpoint volume and the three consecutive observations that immediately preceded the attainment of the endpoint volume. Animals that did not reach the endpoint were assigned a TTE value equal to the last day of the study (53 days).

Treatment efficacy was determined from "tumor growth delay" (TGD), which is defined as the increase in "T" the median TTE for a treatment group compared to "C" the median for control group 1: TGD=T–C, expressed in days, or as a percentage of the median TTE of the control group (% TGD=(TGD/C)×100).

The "percentage of tumor growth inhibition" (TGI) is calculated as:

$$TGI = 100 \times \frac{[MTV_{treated}(day_{18}) - MTV_{treated}(day_0)]}{[MTV_{vehicle}(day_{18}) - MTV_{vehicle}(day_0)]}$$

wherein $MTV_{treated}$ and $MTV_{vehicle}$ are respectively the "median tumor volume" for the animals treated with Compound 1 and animals receiving the vehicle, on day 18 and day 0. Two-tailed statistical analyses were done using GraphPad Prism™ software.

The "MTV(n)" is defined as the median tumor volume on Day 53 in the number of animals remaining, n, whose tumors have not attained endpoint volume.

FIG. 3(a) shows antitumor efficacy results of Compound 1 against human breast tumor xenografts compared with negative and positive controls. Compound 1 produced highly significant inhibition of tumor growth (P<0.01), a 82% TGD (when compared with vehicle), and a 51.6% TGI. A MTV(3) of 6 mm$^3$, and two tumor free survivors were documented. FIG. 3(b) shows the mean body weight of each group during treatment, which showed a 13% body weight loss on Day 8, no severe body weight loss was observed during the period Compound 1 was given once every four days.

Example 7

Toxicity of Compound 1

In vitro toxicity: Sheep red blood cells were exposed to Compound 1 for 2 hrs at 37° C. at concentrations ranging from 2 to 64 μg/mL. Hemolytic activity was determined by monitoring the amount of hemoglobin released spectrophotometrically. Compound 1 displayed hemolytic activity at 11.8 μg/mL (12.8 μM) when prepared in dimethyl sulfoxide (DMSO).

In vivo toxicity: The acute toxicity in CD-1 nu/nu mice of Compound 1 was determined in a saline solution comprising 10% EtOH and 7.5% polysorbate 80. When given i.p., the maximum tolerated dose (MTD) was ≧5 mg/kg. The MTD was 2.5 mg/kg when Compound 1 was administered i.v.

Example 8

Post-Biosynthetic Chemical Modifications a) O-Alkylation Reactions (Preparation of Compounds 20-25, 29 and 30)

Selective O-alkylation reactions are performed either directly with isolation of the desired product, or by first protecting amine groups by reaction with, for example, di-tert-butyl dicarbonate (Boc anhydride) or FMOC, under standard conditions used in amino acid protection. Use of slightly acidic conditions during O-alkylation can also prevent N-alkylation by forming the acid salt of the Pip amines.
Preparation:

Compound 1 (or its protected version) is dissolved in tetrahydrofuran and stirred with iodomethane (1 eq.) and diisopropylethylamine (DIPEA, 1 eq) until reaction is complete or no longer progresses. The reaction mixture is diluted with water and extracted with ethyl acetate (3×). The organic layers are separated and combined. The combined fraction is dried under vacuum and submitted to purification as described in Example 2, or by HPLC (reverse phase conditions using water and acetonitrile as eluent) to afford Compounds 20 to 22. These conditions can also produce bis-O-methylated compounds, tri-O-methylated Compound 23, and hydroxamic acid ester Compound 29, which can be isolated if desired. Compound 30 is produced by replacing iodomethane by iodoethane.

Another example, for the preparation of Compound 23, 3.5 equivalents of iodomethane are used with 2 equivalents of DIPEA and the reaction stirred until completion. The product is isolated as described above.

For the preparation of Compound 24, iodomethane in the above procedure is replaced by ethyl chloroacetate. Carboxylic acid Compound 25 is then produced by hydrolysis or saponification of the ester of Compound 24.

b) O-Acylation Reactions (Preparation of Compounds 15-18, 19 and 28):

Selective O-acylation can also be done by protecting amines or not, as described in (a).
Preparation:

Compound 1 (or its protected version) is dissolved in dimethylformamide and stirred with acetyl chloride (1 eq.) and diisopropylethylamine (DIPEA, 1 eq) until reaction no longer progresses. The reaction mixture is diluted with water and extracted with ethyl acetate (3×). The organic layers are separated and combined. The combined fraction is dried under vacuum and submitted to purification as described in Example 2, or by HPLC to afford Compounds 15 to 17. These conditions can also produce bis-O-acetylated compounds, tri-O-acetylated Compound 18, or fully acetylated Compound 19, which can be isolated if desired.

Another example, for the preparation of Compound 18, 3.5 equivalents of acetyl chloride are used with 1.5 equivalent of DIPEA and the reaction stirred until completion. The product is isolated as described above. To prepare Compound 19, a large excess (more than 5 eq) of both acetyl chloride and DIPEA or any other suitable base is used under the same reaction conditions, and the desired product separated as described.

For the preparation of Compound 28, N—BOC-Gly-OH is used in the above procedure in place of acetyl chloride. In any of the above conditions, a catalyst such as dimethylaminopyridine (DMAP) or hydrobenzotriazole (HOBT) can also be used. Esterification is also performed using coupling agents. The final Compound 28 is produced by cleavage of the N—BOC group using 1 euqvalent of 25% trifluoroacetic acid in dichloromethane. Compound 28 is then isolated as described above.

c) N-alkylation Reactions (Preparation of Compounds 6-14):

For selective N-alkylation reactions, the compound is either used directly and desired compound isolated, or the alcohols are previously protected, for example as silyl ethers, by reacting the starting compound with a large excess of a trialkylsilyl chloride (e.g. chlorotrimethylsilane) and a base (e.g. triethylamine) in dichloromethane. The reaction mixture is diluted with diethyl ether, the triethylamine hydrochloride salt is filtered and the solution concentrated in vacuo. Alcohols may also be protected as their tetrahydropyran ether (THP) by reaction with 3,4-dihydro-2H-pyran using pyridinium p-toluenesulfonate as acid catalyst. Deprotection of silyl ethers is accomplished by the addition, at 0° C. in THF, of a tetrabutylammonium fluoride solution, followed by stirring at room temperature. THP is cleaved, for example by stirring in aqueous hydrochloric acid (1 N). The mixture is neutralized prior to its extraction with an organic solvent.
Preparation:

Compound 1 (or its O-protected version) is dissolved in dimethylformamide and stirred with iodomethane (1 eq.) and diisopropylethylamine (DIPEA, 1 eq) until reaction no longer progresses. The reaction mixture is diluted with water and extracted with ethyl acetate (3×). The layers are separated and the organic layers are combined. The combined fraction is dried under vacuum and submitted to purification as described in Example 2, or by HPLC to afford Compounds 9 and 10 (or their protected version, which are further deprotected to afford the final compounds). These conditions can also produce bis-N-methylated compound Compound 11, which can be isolated if desired.

Compound 11 is also prepared, for example, by reacting a fully THP O-protected Compound 1 with an excess of iodomethane and DIPEA. The reaction is quenched and worked up as above and purified to obtain a THP O-protected Compound 11, which is treated with 1N aqueous hydrochloric acid.

Compounds 12 to 14 are prepared accordingly by replacing iodomethane by n-iodopropane.

d) N-acylation Reactions (Preparation of Compounds 2 to 5, 26 and 27):

N-Acylated compounds are prepared using Compound 1 protected or not, as described in (c).
Preparation:

EDC (1-(3-dimethylaminopropyl)-3-diisopropylethylcarbodiimide hydrochloride, 1 eq) is added to a solution of fully THP O-protected Compound 1 in dichloromethane. DIPEA (1 eq), N—BOC-Glycine (1 eq) and a catalytic amount of DMAP (4-(dimethylamino)pyridine, 0.1 eq) are added and the reaction stirred overnight. The reaction mixture is washed 3 times with a 1N hydrochloric acid aqueous solution. Organic layer is separated, dried over magnesium sulfate, filtered and concentrated in vacuo. The crude residue is dissolved in dichloromethane and treated with a 25% (v/v) TFA solution in dichloromethane until completion and the solution concentrated in vacuo. The residue is analyzed and if the THP survived the BOC deprotection, the residue is further treated with aqueous hydrochloric acid until complete deprotection. The solution is neutralized, extracted with dichloromethane, and concentrated in vacuo to give a crude residue is purified as described in Example 2, or by HPLC. Pooling and concentration of the appropriate fractions give pure Compounds 26 and 27.

Compounds 2 to 4 and Compound 5 are produced by replacing N—BOC-Glycine by acetic acid and pivalic acid respectively. They are also produced by reacting protected Compound 1 with acetyl chloride and pivaloyl chloride respectively, and a base, such as DIPEA and DMAP. To prepare Compounds 2 and 3, 1 equivalent of acyl chloride is used. To prepare Compounds 4 and 5, at least 2 equivalents of their corresponding acyl chloride and base is used.

All patents, patent applications, and published references cited herein are hereby incorporated by reference in their entirety. While this invention has been particularly shown and described with references to preferred embodiments thereof, it will be understood by those skilled in the art that various changes in form and details may be made therein without departing from the scope of the invention encompassed by the appended claims.

The invention claimed is:

1. An isolated compound of Formula I:

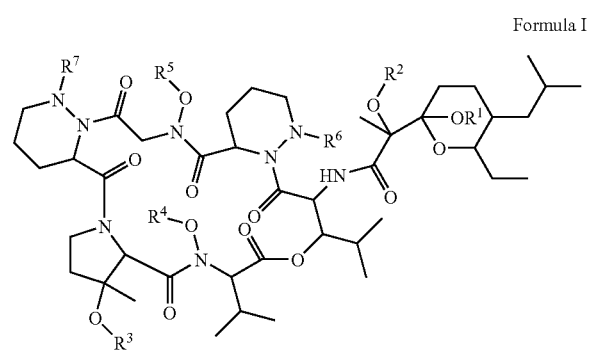

Formula I wherein,
$R^1$, $R^2$ and $R^3$ are each independently selected from H, $R^8$ and $C(O)R^9$;
$R^4$ and $R^5$ are each independently selected from H, $C_{1-6}$alkyl, $C_{1-6}$alkenyl, and $C_{1-6}$alkynyl;
$R^6$ and $R^7$ are each independently selected from H, $R^{10}$ and $C(O)R^{11}$;
$R^8$ and $R^{10}$ are each independently selected form $C_{1-6}$alkyl, $C_{1-6}$alkenyl, $C_{1-6}$alkynyl, $C_{3-10}$cycloalkyl, and $C_{3-10}$heterocycloalkyl;
$R^9$ and $R^{11}$ are each independently selected from H, $C_{1-6}$alkyl, $C_{1-6}$alkenyl, $C_{1-6}$alkynyl, $C_{3-10}$cycloalkyl, $C_{3-10}$heterocycloalkyl, $C_{6-10}$aryl, and $C_{5-10}$heteroaryl, or $C(O)R^9$ and $C(O)R^{11}$ may independently be a C-coupled amino acid;
wherein, when any of $R^1$, $R^2$, $R^3$, $R^4$, $R^5$, $R^6$, $R^7$, $R^8$, $R^9$, $R^{10}$ and $R^{11}$ comprises an alkyl, alkenyl, alkynyl, aryl, heteroaryl, cycloalkyl, or heterocycloalkyl group, then the alkyl, alkenyl, alkynyl, aryl, heteroaryl, cycloalkyl, or heterocycloalkyl group is optionally substituted with substituents selected from the group consisting of acyl, amino, acylamino, acyloxy, carbalkoxy, carboxy, carboxyamido, cyano, halo, hydroxyl, nitro, thio, $C_{1-6}$alkyl, $C_{2-7}$alkenyl, $C_{2-7}$alkynyl, $C_{3-10}$cycloalkyl, $C_{3-10}$heterocycloalkyl, $C_{6-10}$aryl, $C_{5-10}$heteroaryl, alkoxy, aryloxy, sulfinyl, sulfonyl, oxo, guanidino and formyl;
or an ether, an ester, an N-alkylated or N-acylated derivative, or a pharmaceutically acceptable salt thereof.

2. An isolated compound of the formula:

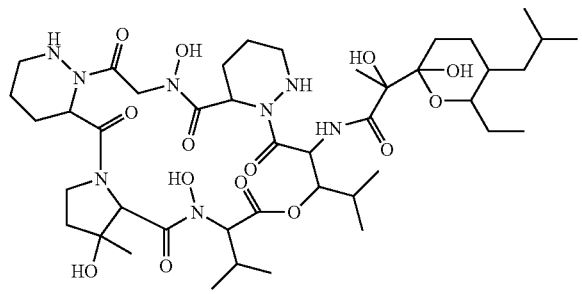

or an ether, an ester, an N-alkylated or N-acylated derivative, or a pharmaceutically acceptable salt thereof.

3. A pharmaceutical composition comprising a compound of claim 1, together with a pharmaceutically acceptable carrier.

4. A process for making a compound of claim 1 comprising
(a) cultivating a *Streptomyces* strain in a nutrient medium comprising at least one source of carbon atoms and at least one source of nitrogen atoms, and
(b) isolating said compound from said nutrient medium.

5. A method of treating a gram positive bacterial infection in a mammal, comprising administering a therapeutically effective amount of a compound of claim 1 to a mammal having a gram positive bacterial infection, thereby treating said gram positive bacterial infection.

6. A method of treating breast cancer, colon cancer or prostate cancer in a mammal, comprising administering a therapeutically effective amount of a compound of claim 1 to a mammal having breast cancer, colon cancer or prostate cancer, thereby treating said breast cancer, colon cancer or prostate cancer.

7. A pharmaceutical composition comprising a compound of claim 2, together with a pharmaceutically acceptable carrier.

8. A process for making a compound of claim 2, comprising:
(a) cultivating a *Streptomyces* strain in a nutrient medium comprising at least one source of carbon atoms and at least one source of nitrogen atoms, and
(b) isolating said compound from said nutrient medium.

9. A method of treating a gram positive bacterial infection in a mammal, comprising administering a therapeutically effective amount of a compound of claim 2 to a mammal having a gram positive bacterial infection, thereby treating said gram positive bacterial infection.

10. A method of treating breast cancer, colon cancer or prostate cancer in a mammal, comprising administering a therapeutically effective amount of a compound of claim 2 to a mammal having breast cancer, colon cancer or prostate cancer, thereby treating said breast cancer, colon cancer or prostate cancer.

* * * * *